United States Patent [19]
Balganesh et al.

[11] Patent Number: 6,027,906
[45] Date of Patent: Feb. 22, 2000

[54] PENICILLIN BINDING PROTEIN DERIVATIVES AND USES THEREOF

[75] Inventors: Tanjore Soundararajan Balganesh, Bangalore, India; Christine Mary Town, Södertälje, Sweden

[73] Assignee: Astra Aktiebolag, Sodertalje, Sweden

[21] Appl. No.: 08/481,435

[22] PCT Filed: Jun. 21, 1995

[86] PCT No.: PCT/SE95/00761

§ 371 Date: Jul. 10, 1995

§ 102(e) Date: Jul. 10, 1995

[87] PCT Pub. No.: WO96/16082

PCT Pub. Date: May 30, 1996

[30] Foreign Application Priority Data

Nov. 24, 1994 [SE] Sweden .................................. 9404072

[51] Int. Cl.[7] .......................... G01N 33/00; C12N 15/03; C07K 14/245
[52] U.S. Cl. ....................... 435/7.37; 435/69.1; 435/69.7; 435/320.1; 435/325; 435/252.33; 435/253.4; 435/7.1; 435/7.2; 435/7.34; 530/350; 536/23.7
[58] Field of Search ........................... 530/350; 435/69.1, 435/69.7, 320.1, 325, 252.33, 253.4, 7.1, 7.2, 7.34, 7.37; 536/23.7, 23.1

[56] References Cited

U.S. PATENT DOCUMENTS 5,508,177 4/1996 Dotzlaf et al. .

FOREIGN PATENT DOCUMENTS 0505151 9/1992 European Pat. Off. .

OTHER PUBLICATIONS

Gittins, Jr. et al., *FEMS Microbiol. Rev.*, 13(1):1–12, Jan. 1994, Abstract only.

Wu, C.Y.E. et al., *J. Bacteriology*, 176(2):443–449, Jan. 1994.

den Blaauwen et al. "Interaction of Monoclonal Antibodies with the Enzymatic Domains of Penicillin–Binding Protein . . . " J. Bacteriol. 172(1): 63–70, 1990.

Nicholas et al. "Penicillin–Binding Protein 1B from *Escherichia coli* contains a membrane associated site . . . " J. Biol. Chem. 268(8): 5632–5641, 1992.

Martin et al. "Nucleotide Sequence of Genes Encoding Penicillin–Binding Proteins from *Streptococcus Pneumoniae* and . . . " J. Bacterial. 174(13): 4517–4523, 1992.

Martin et al. "Relatedness of Penicillin–Binding Protein 1a Genes from Different Clones of Penicillin–Resistant *Streptococcus Pneumoniae* . . . " EMBO J. 11(11): 3831–3836, 1992.

Broome–Smith et al. "The nucleotide sequences of the ponA and ponB genes encoding penicillin–binding proteins 1A and 1B . . . " Eur. J. Biochem. 147:437–446, 1985.

*Primary Examiner*—Marianne P. Allen
*Attorney, Agent, or Firm*—White & Case LLP

[57] ABSTRACT

The present invention relates to variants of Penicillin Binding Proteins (PBP), which proteins are involved in bacterial peptidoglycan biosynthesis. Disclosed are also DNA molecules coding for the said PBP variants, as well as vectors and cells harbouring such DNA molecules. The invention is also related to processes for assaying and designing therapeutically useful compounds which have high affinity to PBP, which processes utilize the said PBP variants.

33 Claims, 14 Drawing Sheets

Panel A      Panel B

Panel A                Panel B

Hydrophobicity plot E.coli PBP 1B (1-150 a.a)

NcoI - NruI fragment from pARC0547 cloned into NcoI-EcoRV sites of pARC0534.

Panel A        Panel B

Hydrophobicity Plot S. pneumoniae PBP1A (1-100 a.a)

```
E.1B  190  DPRLITMISSPNGEQR.LFVPRSGFPDLLVDTLLATEDRHPYEHDGISLYSIGRAVLANLTAGRTVQGASTLTQQLVKNLPLS...
                           *            **   *    **  *           *  **     ***** *
S.1A   55  IYDNKNQLIADLGSERRVNAQANDIPTDLVKATVSIEDHRPFDHRGIDTIRILGAFLRNLQSN.SLQGGSALTQQLIKLTYPSTST
           **    ***    **       **    ***           **  ***       ***    *    ****
E.1A   50  IYSADGELIAQYGEKRRIPVTLDQIPPEMVKAFIATEDSRPFYEHHGVDPVGIFRAASVALFSGHASQGASTITQQLARNFFLS...
           ** ***                                  ***** *                ***************
H.inf  50  IYTADGKLGGEVGEQRRIPVKLADVPQRLIDAFLATEDBRPFYDHHGLDPIGIARALFVFYSNGGASQGASTITQQLARNFFLI...

REGION 1                                    REGION 2

E.1B       SERSYWRKANEAYMALIMDARYSKDRILELYMNEVYLGQSGDNEIRGFPPLASLYYFGRPVEELSLDQQALLVGMVKGASIYNPWR
                *             **  **  **  *     *              **               **    *
S.1A       SDQTISRKAQEAWLAIQLEQKATKQEILTYYINKVYMS....NGNYGMQTAAQNYYGKDLNNLSLPQLALLAGMPQAPNQYDPYS
              *        ***  **  **   *********       **                          **
E.1A       PERTLMRKIKEVELAIRIEQLLTKDEILELYLNKIYLG....YRAYGVGAAAQVYFGKTVDQLTLNEMAVIAGLPKAPSTFNPLY
                      *  *****   *** ****** ***

PENICILLIN BINDING PROTEIN DERIVATIVES AND USES THEREOF

TECHNICAL FIELD

The present invention relates to variants of Penicillin Binding Proteins (PBP), which proteins are involved in bacterial peptidoglycan biosynthesis. Disclosed are also DNA molecules coding for the said PBP variants, as well as vectors and cells harbouring such DNA molecules. The invention is also related to processes for assaying and designing therapeutically useful compounds which have high affinity to PBP, which processes utilize the said PBP variants.

BACKGROUND ART

Bacteria and most other unicellular organisms possess a cell wall, which comprises a cross-linked polysaccharide-peptide complex called peptidoglycan. Peptidoglycan biosynthesis consists of three stages: (1) synthesis of precursors (sugar nucleotides) in the cytosol, (2) precursor transfer across the membrane and formation of the polysaccharide chain, and (3) cross-linking of individual peptidoglycan strands in the cell wall.

In the latter stage of peptidoglycan biosynthesis, new bonds must be made between nascent glycan strands and existing peptidoglycan. The newly synthesized chains are about 10 disaccharides long and are extended by transglycosylase enzymes to a final glycan strand of between 100 and 150 disaccharide units. The peptidoglycan is crosslinked by the action of transpeptidases which link the terminal D-ala of one glycan strand to a free $\epsilon$-amino group on a diaminopimelic acid residue on an adjacent region.

A number of antibiotics inhibit bacterial growth by interfering with the formation of the peptidoglycan layer. The cross-linking reaction is the target for action of two important classes of such antibiotics, the penicillins and the cephalosporins. Penicillin is thought to react irreversibly with the transpeptidase that catalyses cross-linking.

The penicillin interactive proteins fall into three groups: the $\beta$-lactamases, the Low Molecular Weight-Penicillin Binding Proteins (PBPs), which mainly include the carboxypeptidases, and the High Molecular Weight-Penicillin Binding Proteins. Penicillin Binding Proteins are those enzymes which have been shown to bind radiolabelled penicillin G. In *Escherichia coli* such proteins are called e.g. PBP 1A and PBP 1B, both belonging to the class High Molecular Weight-PBPs. PBP 1A and 1B, which are known to be membrane bound proteins, maintain cell integrity and control peptidoglycan side wall extension during growth. Inactivation of either PBP 1A or PBP 1B can be tolerated by the bacteria while the deletion of both the genes, designated ponA and ponB, is lethal (Yousif et al., 1985).

PBP 1B is known to be a bifunctional enzyme possessing both transpeptidase and transglycosylase activity (Ishino et al., 1980). PBP 1A is believed to be bifunctional since it can substitute for PBP 1B. The $\beta$-lactam antibiotics, such as penicillin, inhibit only the transpeptidase activity of these proteins.

The transglycosylase reaction is inhibited by e.g. moenonmycin, which is a phosphoglycolipid used as a growth promoter in animal nutrition and which has been shown to possess broad spectrum bactericidal activity. The enzyme transglycosylase has been shown to be present in *Escherichia coli*, *Staphylococcus aureiis*, *Bacillus megateriium* and *Bacillus subtilis*. This suggests that interference of peptidoglycan biosynthesis by inhibition of transglycosylase could be a lethal event in all clinically important pathogens.

The putative transglycosylase domain of PBP 1B has been assigned to the N-terminal 478 amino acids (Nakagawa et al., 1987). This regions includes three conserved stretches of amino acids between the N-terminal half of both PBP 1A and 1B and could represent residues involved in the transglycosylase activity.

Preparation of Penicillin Binding Protein 2A from *Staphylococcus aureus* is disclosed in EP-A-0505151.

DISCLOSURE OF THE INVENTION

There is a growing number of reports of bacteria which are resistant to antibiotics. There is consequently a need for new compounds which inhibit bacterial growth by means of binding Penicillin Binding Proteins. The present invention provides PBP variants which facilitate processes for assaying and designing therapeutically useful compounds which have high affinity to PBPs.

Accordingly, it is an object of the invention to provide polypeptides which are water-soluble active derivatives of bacterial bifunctional Penicillin Binding Proteins, said Penicillin Binding Proteins being bound to the cell membrane when expressed in a bacterial cell and being capable of exhibiting both transglycosylase and transpeptidase activities and said derivatives lacking a membrane anchoring sequence but retaining the capability to exhibit one or both of said enzymic activities. The "bacterial cell" mentioned above is preferably an *Escherichia coli* cell or a *Streptococcus pneumoniae* cell.

The soluble PBP variants according to the invention retains transglycosylase activity, indicating that soluble variants of PBP, devoid of membrane anchoring sequences, can recognize lipid linked substrate and polymerise the disaccharide into repeating units. It can thus be assumed that other analogues of PBP lacking residues involved in membrane attachment would be enzymatically functional.

Molecules interacting with the penicillin interactive region of soluble PBP variants could be assumed to be capable of interacting identically with wild-type PBPs. Consequently, the soluble PBP variants according to the invention can be used for identifying compounds which are interacting with wild-type Penicillin Binding Proteins.

It is furthermore well known that membrane-bound proteins are very difficult to crystallize. The soluble enzymatically active PBP variants can be used for crystallisation and will thereby facilitate a rational design, based on X-ray crystallography, of therapeutic compounds inhibiting High Molecular Weight-PBPs.

A further object of the invention is to provide polypeptides which are truncated water-soluble derivatives of bacterial bifunctional Penicillin Binding Proteins, said Penicillin Binding Proteins being bound to the cell membrane when expressed in a bacterial cell and being capable of exhibiting both transglycosylase and transpeptidase activities and said derivatives lacking the membrane anchoring sequence but retaining the capability to exhibit the transglycosylase activity. The "bacterial cell" mentioned above is preferably an *Escherichia coli* cell.

Alignment of amino acid sequences of High Molecular Weight-Penicillin Binding Proteins, and the compilation of the motifs involved in the penicillin binding of $\beta$-lactamases and carboxypeptidase, have suggested the C-terminal half of PBP 1A and 1B to be the functional domain of the transpeptidase activity and includes the penicillin binding domain. In addition, Nakagawa et al. (1987) showed that a truncated ponB gene encoding the N-terminal 478 amino acids of PBP 1B is capable of the transglycosylase reaction.

On the basis of these findings, it has been suggested that the high molecular weight PBP 1A and 1B proteins are two domain-proteins, with the N-terminal half forming the transglycosylase domain and the C-terminal half the transpeptidase domain. The two domains have been predicted by computer analysis to be joined by a linker or hinge region which does not structurally or enzymatically contribute to the function of the protein. The linker region of E.coli PBP 1B has been predicted to be from position 545–559 while that for E.coli PBP 1A around position 501.

The monofunctional truncated variants of PBP according to the invention will, when used in x-ray crystallography, facilitate obtaining structural information of the transglycosylase domain of penicillin binding proteins. In addition, the reduced size of the monofunctional variant will facilitate crystallization.

In a preferred form, a water-soluble polypeptide according to the invention has an amino acid sequence which is identical to SEQ ID NO: 2, 4, 6, 12 or 13 in the Sequence Listing.

The observation that deletion of the ponA and ponB genes is lethal (Yousif et al., 1985) does not address the question of essentially of the transglycosylase activity of the encoded PBP 1A proteins, since the deletion results in the loss of both transglycosylation and transpeptidation activities. In addition, this experiment does not address the possibility that the transglycosylase enzyme activity can be contributed by a Penicillin Binding Protein other than PBP 1A or PBP 1B. It is also possible that hitherto undescribed Penicillin Binding Proteins and/or other proteins that contribute to the transglycosylase activity exist.

Alignment of the amino acids forming the putative transglycosylase domain of PBP 1A and 1B reveals three stretches of 9 out of 12 (Region 1), 9/10 (Region 2) and 8/10 (Region 3) amino acids identical within the N-terminal half of these two proteins (Broome-Smith et al., 1985) (FIG. 14). The same 3 regions are identically conserved among two other recently described protein sequences; *Streptococcus pneurnoniae* PBP 1A (Martin et al., 1992) and a 94 kDa protein from *Haemophilus influenzae* (Tomb et al., 1991). The conservation of these residues in such diverse species suggests their critical requirement in either maintaining structural aspects of the protein, or in the transglycosylation reaction itself.

The overlapping functional transglycosylase and transpeptidase activities of PBP 1A and 1B also suggests conservation of the catalytic centers and that molecules designed to interact with the catalytic center of PBP 1A would be reactive also with PBP 1B.

The functional transglycosylase activity of the expressed protein can be studied either in a direct in vitro assay using appropriate substrates, or in an assay measuring the ability of the protein to complement the deletion of the corresponding genes in the chromosome. It has been shown that a plasmid with a gene encoding the wild type product (PBP 1A or PBP 1B) is capable of maintaining the viability of the E.coli cell (Yousif et al., 1985). This trans-complementation technique can be utilized to assess the functional nature of the mutant gene(s) encoding PBPs with mutations inactivating one of the enzymic (transglycosylation or transpeptidation) functions. The ability of such mutant products to complement in trans the deletion of the chromosomal ponA and ponB genes would define the essential requirement of the individual enzymic functions.

There is consequently a need for research tools which will make it possible to study the effects of specific inactivation of the transglycosylase activity of Penicillin Binding Proteins.

Consequently, a further aspect of the invention is a polypeptide which is a transglycosylase deficient derivative of a bacterial bifunctional penicillin binding protein, said penicillin binding protein being bound to the cell membrane when expressed in a bacterial cell and being capable of exhibiting both transglycosylase and transpeptidase activities and said derivative lacking the capability to exhibit transglycosylase activity but retaining the capability to exhibit transpeptidase activity. The "bacterial cell" mentioned above is preferably an *Escherichia coli* cell.

The transglycosylase deficient PBP variants can advantageously be used in X-ray crystallography for the purpose of obtaining structural information of the activity sites of PBPs. Structural analysis of crystal form of soluble transglycosylase deficient PBP variants could allow delineation of the catalytic region and facilitate the design of molecules capable of specifically inhibiting the transglycosylase activity.

In a preferred form, the transglycosylase deficient polypeptide according to invention is a polypeptide which is lacking transglycosylase activity because of a mutation or deletion in the second conserved region of the gene coding for said polypeptide.

In a further preferred form, the transglycosylase deficient polypeptide according to the invention has an amino acid sequence which is identical to SEQ ID NO: 7, 8, 9, or 10 in the Sequence Listing.

The conventional purification procedure employed for the enrichment of penicillin binding proteins has been the use of a "penicillin" affinity. The binding of the protein to penicillin is covalent and requires harsh conditions to elute the bound protein. This may lead to a certain degree of inactivation of the enzymic activity of the protein. There is consequently a need for alternate affinity matrices for the efficient purification of the proteins.

Included in the invention is consequently a polypeptide comprising (a) a first polypeptide which is a PBP variant according to the invention; and (b) an additional polypeptide which allows binding to an affinity matrix; there being a cleavage site between said polypeptides.

The "additional polypeptide" mentioned above can preferably be glutathione-S-transferase or a polypeptide substantially similar to glutathione-S-transferase. Such an additional polypeptide will enable rapid purification of the protein using Glutathione Sepharose® affinity matrix. In another preferred form, the additional polypeptide is a polypeptide rich in histidine residues, which residues will confer on the protein the ability to bind to an Ni affinity column. The additional polypeptide can be fused either to the N-terminus or the C-terminus of the soluble/membrane bound PBP.

The ability of the fusion proteins to bind to an affinity matrix allows immobilization of the protein. Such immobilised proteins can be used for analysis of competitive binding of different ligands to the bound active protein, and thus for screening of compounds binding to the enzymic domain of interest.

The polypeptides according to the invention are not to be limited strictly to any one of the sequences shown in the Sequence Listing. Rather the invention encompasses polypeptides carrying modifications like substitutions, small deletions, insertions or inversions, which polypeptides nevertheless have substantially the biochemical activities of the PBP variants which amino acid sequence is disclosed in the Sequence Listing. Included in the invention are consequently also polypeptides, the amino acid sequence of which is at least 90% homologous, preferably at least 95% homologous, with the amino acid sequence of any of the PBP variants according to the invention.

A further object of the invention is to provide isolated and purified DNA molecules which have nucleotide sequences coding for any one of the PBP variants according to the invention.

In a preferred form of the invention, the said DNA molecules have nucleotide sequences identical to SEQ ID NO: 1, 3 or 5 in the Sequence Listing. However, the DNA molecules according to the invention are not to be limited strictly to any of the sequences shown in the Sequence Listing. Rather the invention encompasses DNA molecules carrying modifications like substitutions, small deletions, insertions or inversions, which nevertheless encode proteins having substantially the biochemical activities of the PBP variants according to the invention.

Included in the invention is also a DNA molecule which nucleotide sequence is degenerate, because of the genetic code, to the said nucleotide sequence coding for a PBP variant according to the invention. The natural degeneracy of the genetic code is well known in the art. It will thus be appreciated that the DNA sequences shown in the Sequence Listing are only examples within a large but definite group of DNA sequences which will encode the PBP variants which amino acid sequences are shown in the Sequence Listing.

A further aspect of the invention is a replicable expression vector which carries and is capable of mediating the expression of a DNA molecule according to the invention. In the present context the term "replicable" means that the vector is able to replicate in a given type of host cell into which is has been introduced. Examples of vectors are viruses such as bacteriophages, cosmids, plasmids and other recombination vectors. Nucleic acid molecules are inserted into vector genomes by methods well known in the art. A vector according to the invention can preferably be one of the plasmids listed in Table 1 below.

Included in the invention is also a host cell harbouring a vector according to the invention. Such a host cell can be a prokaryotic cell, a unicellular eukaryotic cell or a cell derived from a multicellular organism. The host cell can thus e.g. be a bacterial, yeast or mammalian cell. The methods employed to effect introduction of the vector into the host cell are well-known to a person familiar with recombinant DNA methods.

A further aspect of the invention is a process for production of a polypeptide which is a derivative of penicillin binding protein, comprising growing a host cell according to the invention in or on a culture medium for expression of the polypeptide and optionally recovering the polypeptide. An appropriate host cell may be any of the cell types mentioned above, and the medium used to grow the cells may be any conventional medium suitable for the purpose.

The High Molecular Weight-Penicillin Binding Proteins have been shown to be anchored to the membrane, but the majority of the protein is within the periplasmic space of the cell (Edelman et al. 1987). Thus PBP derivatives, devoid of the membrane signal/anchoring sequences, are forced to fold into their native state in a heterologous environment, namely the cytosol. This often leads to misfolding, and the majority of the expressed protein aggregates into an inactive form referred to as inclusion bodies.

It has now surprisingly been found that high yields of an active water-soluble PBP variant can be obtained by regulated transcription of the gene encoding the said PBP variant. Such regulated transcription involves (i) using a suboptimal concentration of the inducer isopropyl thiogalactoside (IPTG); and (ii) culturing the cells expressing the PBP variant at reduced temperature. A cumulative effect of these factors contributes to the overall recovery of the active soluble protein. Consequently, lower rates of expression, achieved through the mentioned combination of (i) suboptimal de-repression of promoter systems and (ii) increased generation time by lowering of the temperature of cultivation, will enhance the solubility of proteins lacking the membrane anchoring segment.

A further important aspect of the invention is a process for the production of a water soluble polypeptide according to the invention which comprises culturing *Escherichia coli* cells harbouring an expression vector wherein a DNA coding sequence for said polypeptide is under the control of an isopropyl thiogalactoside (IPTG)—inducible promoter, said culturing being carried out in the presence of a suboptimal concentration of IPTG for induction of the said promoter and at a temperature in the range of 20 to 24° C., preferably 22° C. The concentration of IPTG can preferably be approximately 0.01 mM.

In the case of expression of ponAdel23, a gene encoding a PBP variant according to the invention, such regulated transcription by (i) controlled de-repression of the T7 promoter by using sub-optimal concentration of the inducer IPTG and (ii) reducing the growth rate by culturing at 22° C., resulted in yields of the active protein which reached nearly 50% of the total induced protein of interest. The growth and induction conditions were critical for the efficient recovery of the soluble protein, as growth at higher temperatures or induction with higher concentrations of IPTG resulted in the majority of the protein becoming inactive and forming inclusion bodies.

It will be appreciated that this method for controlled expression is applicable to other inducible promoter systems, e.g. the tac system, where the inducer is IPTG and the host is a lac Y negative host.

A route to obtain relevant structural information on the active site configuration of an enzyme is the production and characterization of monoclonal antibodies capable of inhibiting the enzymic reaction. The antibodies inhibiting the activity represent molecules which block or compete with the substrate for entry into the active site pocket, or can represent molecules which can prevent structural transitions required for catalytic activity. In either case, these antibodies can be used as a tool to quantitate interaction of the target enzyme with binding of radiolabelled inhibitory compounds to judge the affinity of interaction provided the affinity of the inhibiting antibody is known. A further use of mapping the epitopes recognised by the inhibitory antibodies is the ability to delineate residues forming the active site.

Consequently, a further aspect of the invention is a method of identifying an antibody capable of binding a bacterial bifunctional penicillin binding protein which includes the step of employing a polypeptide according to the invention in an antibody binding assay and selecting antibodies that bind to the polypeptide.

Also included in the invention are monoclonal antibodies directed to a PBP variant according to the invention. Such a monoclonal antibody is prepared using known hybridoma technology by fusing antibody-producing B-cells from immunized animals with myeloma cells and selecting the resulting hybridoma cell line producing the desired antibody.

Another aspect of the invention is a method of assaying for compounds which bind to a penicillin binding protein, said method comprising (a) contacting a polypeptide which is a PBP variant according to the invention with a compound to be investigated; and (b) detecting whether said compound binds to the said PBP variant.

For example, a method of assaying for compounds which bind to a penicillin binding protein can comprise (a) culturing host cells according to the invention; (b) lysing the said cells and isolating the crude cell extract; (c) exposing the said cell extract to potential inhibitors of a penicillin binding protein; (d) introducing an agent, known to bind a penicillin binding protein, to the said cell extract; (e) removing the unbound fraction of said agent; and (f) assaying the presence of said agent remaining in the cell extract.

Another method of assaying for compounds which bind to a penicillin binding protein could comprise (a) exposing a polypeptide which is a PBP variant according to the invention, immobilised on a solid support, to a potential inhibitor of a penicillin binding protein; (b) exposing an agent, known to bind a penicillin binding protein, to the immobilised polypeptide; (c) removing the unbound fraction of said agent; and (d) assaying the presence of said agent bound to the immobilised polypeptide.

In a preferred form, the said method is a method of assaying for compounds which bind to the transglycosylase domain of a penicillin binding protein, said method comprising (a) exposing the transglycosylase domain of a polypeptide according to the invention, with the proviso that the polypeptide is not a transglycosylase deficient PBP variant, said polypeptide being immobilised on a solid support, to a potential inhibitor of the transglycosylase activity of a penicillin binding protein; (b) exposing an agent, known to bind the transglycosylase domain of a penicillin binding protein, to the immobilised polypeptide; (c) removing the unbound fraction of said agent; and (d) assaying the presence of said agent bound to the immobilised polypeptide.

Antibodies specific for transpeptidase can be immobilised on a BIAcore sensor chip surface. The BIAcore system, wherein "BIA" stands for "Biospecific Interaction Analysis", is available from Pharmacia Biosensor, Sweden. Protein binding to the immobilised antibody is detected by the output RU-signal. Screening for TP inhibitors will be possible by a competitive assay wherein soluble protein is preincubated with test compounds. Binding of a test compound to the protein will result in a decrease in protein binding to TP specific antibody. In the same way, monoclonal antibodies specific for transglycosylase can be used in screening for TG inhibitors.

In a similar way, ampicillin or modified moenonmycin can be coupled to the surface and used in an indirect competitive assay whereby protein is preincubated with test ligand prior to introduction in the BIAcore.

Consequently, yet another method of assaying for compounds which bind to a penicillin binding protein could comprise (a) exposing a polypeptide which is a PBP variant according to the invention to a potential inhibitor of a penicillin binding protein; (b) exposing the polypeptide to an agent, known to bind a penicillin binding protein, which agent is immobilised on a solid support; and (c) assaying the presence of polypeptide bound to the immobilised agent.

In a preferred form, the said method is a method of assaying for compounds which bind to the transglycosylase domain of a penicillin binding protein, said method comprising (a) exposing the transglycosylase domain of a polypeptide according to the invention, with the proviso that the polypeptide is not a transglycosylase deficient PBP variant, to a potential inhibitor of a penicillin binding protein; (b) exposing the said polypeptide to an agent, known to bind to the transglycosylase domain of a penicillin binding protein, which agent is immobilised on a solid support; and (c) assaying the presence of polypeptide bound to the immobilised agent.

The "agent known to bind a penicillin binding protein" referred to above can e.g. be a monoclonal antibody or a labelled antibiotic compound such as [$^3$H]ampicillin.

A further aspect of the invention is a method of determining the protein structure of a penicillin binding protein, characterized in that a polypeptide which is a PBP variant according to the invention is utilized in X-ray crystallography.

Some of the features of the preferred PBP variants according to the invention are summarised in Table 1 below. The plasmids listed in the Table have been deposited under the Budapest Treaty at the National Collection of Industrial and Marine Bacteria Limited (NCIMB), Aberdeen, Scotland, UK. The date of deposit is Jun. 28, 1994.

TABLE 1

| Example no. | Features | Plasmid (pARC) | Deposit no. (NCIMB) | FIG. | SEQ ID NO: |
|---|---|---|---|---|---|
| Soluble variants | | | | | |
| 1.1 | E.coli PBP 1A with aa 1–23 deleted | 0558 | 40666 | 3 | 1, 2 |
| 2.1 | E.coli PBP 1B with aa 65–87 deleted | 0559 | 40667 | 9 | 3, 4 |
| 3.1 | S.pneumoniae PBP 1A with aa 1–38 deleted | 0512 | 40665 | 12 | 5, 6 |
| Transglycosylase deficient variants | | | | | |
| 4.1 | E.coli PBP 1B with glutamines 270–271 substituted to alanines | 0438 | 40661 | | 7 |
| | E.coli PBP 1B with glutamines 270–271 substituted to leucines | 0468 | 40662 | | 8 |
| | E.coli PBP 1B with aa 264–271 deleted | 0469 | 40663 | | 9 |
| 4.2 | E.coli PBP 1A with glutamines 123–124 substituted to alanines | 0571 | 40668 | 19 | 10 |
| Truncated variants | | | | | |
| 5.1 | aa 1–553 of E.coli PBP 1B | 0592 | 40669 | 21 | 11 |
| | aa 1–553 of E.coli PBP 1B, with aa 65–87 deleted | 0593 | 40670 | 22 | 12 |
| 5.2 | aa 210–368 of E.coli PBP 1B | 0392 | 40659 | 23 | 13 |
| Fusion proteins | | | | | |
| 6.1 | E.coli PBP 1A with 23 aa deletion, ligated to glutathione-S-transferase | 0499 | 40664 | 24 | |
| 6.2 | E.coli PBP 1A with 23 aa deletion, ligated to histidine stretch | 0400 | 40660 | 25 | |

EXAMPLES OF THE INVENTION

In the following examples, the terms "standard protocols" and "standard procedures" are to be understood as protocols and procedures found in an ordinary laboratory manual such as the one by Sambrook, Fritsch and Maniatis (1989).

Example 1

1.1. Construction of Gene Encoding Soluble Form of *E.coli* PBP 1A

The possible amino acid residues involved in the membrane anchoring region of PBP 1A was deduced following the computer program described by Kyte & Dolittle (1982). The predicted hydrophobicity of the N-terminal 60 amino acid is shown in FIG. 1. Based on this hydrophobicity profile, it was predicted that the N-terminal 23 amino acids were strongly implicated to contribute to the membrane anchoring domain of the protein, but may not entirely encompass the membrane anchoring domain. This region was then putatively designated as the region involved in "membrane anchoring".

The plasmid pBS98, harbouring the native ponA gene (encoding wild type PBP 1A), was obtained from Prof. B. S. Spratt, Microbial Genetics Group, School of Biological Sciences, University of Sussex, Brighton, UK. The construction of pBS98 is described in Broome-Smith et al. (1985). Plasmid DNA from cells harbouring pBS98 was made following standard protocols.

Oligonucleotide primers for use in the polymerase chain reaction (PCR) were synthesized in Applied Biosystems Model 380 A. The 5'-oligonucleotide primer used was TG-82:

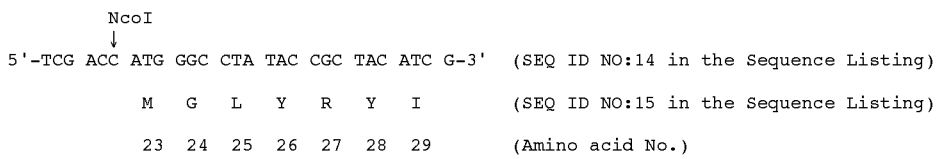

TG-82 incorporates the following characteristics: (1) it allows construction of mutant ponA gene whose encoded product would have the 24th amino acid (glycine) of the wild type PBP 1A as the second amino acid of the expressed mutant protein; and (2) it introduces DNA sequences recognized by the restriction enzyme NcoI. This introduces the codon ATG which corresponds to the first amino acid of the mutant PBP 1A when expressed in suitable systems.

The 3'-oligonucleotide primer used was TG-64:

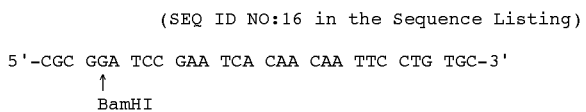

TG-64 has the following characteristics: (1) it introduces a termination codon following the 850th amino acid of the structural protein of PBP 1A; (2) it introduces a site for the restriction enzyme BamHI to facilitate cloning into suitable expression vectors.

Using these primers, PCR was carried out using pBS98 DNA as template following standard protocols. A DNA fragment of approximately 2.5 kb was amplified. The fragment was digested with the restriction enzyme NcoI followed by digestion with BamHI. This 2.5 kb NcoI-BamHI DNA fragment was then ligated to the vector pBR329 (Covarrubias et al., 1982) previously cut with NcoI and BamHI. Ligation of the two DNA fragments were carried out using standard protocols and the ligation mixture transformed into *E.coli* DH 5α. The transformed cells were plated on LB agar plates with 50 µg/ml ampicillin. Following overnight incubation at 37° C., individual ampicillin resistant colonies were tested for their tetracycline sensitivity as insertion into the NcoI - BamHI region renders the plasmid chloramphenicol and tetracycline sensitive. A recombinant plasmid bearing the 2.5 kb insert was designated pARC0488.

The NcoI - BamHI 2.5 kb DNA fragment was released from pARC0488 and ligated to NcoI - BamHI cleaved and purified pARC038 (FIG. 2). The plasmid pARC038 is a derivative of pET11d (Studier et al., 1990) in which the EcoRI and PstI sites were made blunt ended with T4 exonuclease and the EcoRI - PstI 0.75 kb DNA fragment replaced with a blunt ended kanamycin resistance cartridge (Pharmacia Biochemicals). The ligation mixture was transformed into competent cells of *E.coli* BL 26 (DE3). The transformation mix was plated on LB agar with 50 µg/ml kanamycin. Min-prep plasmid DNA was made from several kanamycin resistant colonies and screened by restriction endonuclease mapping using standard procedures.

One of the colonies harbouring plasmid with expected structure (FIG. 3) was labelled pARC0558 (NCIMB 40666). The DNA sequence of the mutant ponA gene labelled as ponAdel23 is shown as SEQ ID NO: 1. The amino acid sequence of the soluble PBP 1Adel23 is shown as SEQ ID NO: 2.

1.2. Expression of ponAdel23

*E.coli* BL 26 (DE3) cells (obtained from Dr. J. J. Dunn, Biology Dept., Brookhaven National Lab., Long Island, N.Y., USA) harbouring pARC0558 were grown in LB with 50 µg/ml kanamycin till an O.D. at 600 nm of 0.6 and induced with 0.01 mM isopropyl thiogalactoside (IPTG) for 6 hours.

Following 6 hours of induction, cells were harvested and broken by passing through a French press. After centrifugation at low speed to remove unbroken cells and debris, the cytosolic (soluble) fraction was obtained by either of the following two methods: (1) following a procedure described Page et al. (1982) in which the pellet, membrane and soluble proteins are separated by sucrose gradient centrifugation; or (2) by spinning the obtained supernatant at 200,000×g for 90 minutes, whereafter the supernatant obtained is taken as the cytosolic/soluble protein fraction.

1.3. Penicillin binding of expressed PBP 1Adel23

The obtained cytosolic fraction was tested for the presence of mutant PBP 1A by following the method of Rojo et al. (1984). This procedure involves using [$^{125}$I]cephradine as the labelled penicillin as it is specific for PBP 1A. Mutant PBP 1Adel23 capable of binding the labelled cephradine could be demonstrated in the cytosolic fraction. Approximately 50% of the expressed mutant protein fractionated as a soluble protein, while the remaining 50% fractionated into the inclusion body and/or into the membrane associated fractions. Consequently, enhanced levels of active mutant PBP 1Adel23 were obtained since the cells were induced with sub-optimal concentration of IPTG and the since cultures were grown at 22° C. The penicillin binding profile of the soluble PBP 1Adel23 is shown in FIG. 4.

1.4. Purification of Soluble PBP 1Adel23

The cell pellet of *E.coli* BL26 (DE3)/pARC0558 obtained following 6 hours of induction at 22° C. was washed twice with buffer A (30 mM Tris-Cl, pH 8.0; 10 mM EDTA; 10 μg/ml leupeptin; 10 μg/ml aprotinin; 5 mM DTT) and resuspended in the same buffer. The cell suspension was passed through a French press at 1200 psi. The lysate was spun at 10,000 rpm for 10 minutes and the obtained supernatant centrifuged at 200,000×g for 45 minutes. The obtained supernatant was then adjusted to 30% saturation with ammonium sulphate. The mixture was centrifuged at 12,000 rpm for 10 min and the pellet resuspended in buffer A containing 1 M NaCl. The dissolved pellet was then treated with Cephradine-Affigel 10 matrix.

Cephradine was conjugated to Affigel 10 following the instructions of the manufacturers (Biorad Laboratories, USA). The soluble PBP 1Adel23 containing fraction, dissolved in buffer A containing 1 M NaCl, was incubated 16 hrs at 4° C. with cephradine-affigel 10 beads. The beads were then washed with Buffer A containing 1 M NaCl until the absorbance at 280 nm was nearly zero. Elution of PBP 1Adel23 was monitored by assaying for penicillin binding activity in the wash. This activity was measured using [$^{125}$I]cephradine prepared as described in Rojo et al. (1984). Bound PBP 1Adel23 was eluted from the beads using 1 M hydroxylamine (pH 8.5) at 25° C. for 120 minutes. This fraction was concentrated by ultrafiltration using YM 30 filters (Amicon, USA) in Buffer A with 0.25 M NaCl. The ultrafiltration also resulted in the removal of hydroxylamine. The purified fraction containing >85% of the protein species corresponding to PBP 1Adel23 showed both penicillin binding and transglycosylase enzyme activities. The protein profile as seen by Coomassie Brilliant Blue staining and the [$^{125}$I]cephradine/penicillin binding profile of the different fractions, obtained during the various stages of purification, are shown in FIG. 5. The N-terminial amino acid sequence of the soluble PBP 1Adel23 was confirmed by sequencing the purified protein.

1.5. Transglycosylase Activity of Soluble PBP 1Adel23

The transglycosylase activity of the soluble PBP 1Adel23 protein was measured using essentially the method described by Isino et al. (1980). The substrate for the detection of the enzymic activity were essentially prepared and purified following the protocols described by Heijenoort et al. (1992). The concentration dependent transglycosylase activity of PBP 1Adel23 measured as the amount of peptidoglycan formed was compared to the amounts of peptidoglycan formed by different concentrations of the membrane bound form of native PBP 1A. As seen in FIG. 6, the peptidoglycan polymerizing efficiency of the mutant soluble PBP 1Adel23 was nearly identical to the enzymic activity of the membrane bound form of the protein.

It has consequently been found that the elimination of the 23 amino acid residue stretch does not interfere with the ability of the protein to assume its native structure capable of both the enzymatic activities, i.e. the transglycosylase and the transpeptidase activities.

Example 2

2.1. Construction of Gene Encoding Soluble Form of *E.coli* PBP 1B

The ponB gene encoding PBP 1B was obtained on a plasmid pBS96 from Prof. B. S. Spratt, Microbial Genetics Group, School of Biological Sciences, University of Sussex, Brighton, UK. The construction of pBS96, as well as the nucleotide sequence of the wild-type ponB gene and the derived amino acid sequence, are described in Broome-Smith et al. (1985).

The hydropathy plot of the N-terminal approximately 150 amino acids as derived using the method of Kyte and Doolittle (1982) is shown in FIG. 7. Analysis of the hydropathicity plot indicated that the amino acids at positions 65 to 87 of the PBP 1B sequence contributed largely to the hydrophobicity of the N-terminus and can be putatively assigned to be the membrane anchoring domain of the protein. In addition, β-lactamase studies of Edelman et al. (1987) had indicated that amino acids C-terminal to amino acid position 87 were present in the periplasmic space of the *E.coli* cell and that amino acids N-terminal to position 65 of PBP 1B were within the cytoplasm of the cell.

The strategy employed to construct a mutant ponB gene encoding a soluble form of PBP 1B is shown in FIG. 8. Initially a DNA fragment of approximately 200 bp of the 5'-end of the ponB gene was amplified by PCR, from the ponB gene on the plasmid pBS96 (Broome-Smith et al., 1985). The oligonucleotide primers used were 5'-primer TG-77 (5'-GAA AAA CCA TGG CCG GGA ATG ACC-3') which includes a NcoI restriction (SEQ ID NO:17 in the Sequence Listing) enzyme site which also coincides with the start ATG codon of the sequence, and 3'-primer TG-84 (5'-AAG TCG CGA GCC GCG TTT GCC AC-3') which includes a site for the restriction enzyme NruI and encodes (SEQ ID NO:18 in the Sequence Listing) for amino acids corresponding to position 64 of the PBP 1B sequence.

Step 1: The PCR amplified fragment following restriction with the enzymes NcoI and NruI was cloned into the NcoI-NruI sites of the cloning vector pBR 329 (Covarrubias et al., 1982). Ligation, transformation and screening were carried out using standard protocols and the recombinant plasmid with the expected structure labelled pARC0547 (FIG. 8) was obtained.

Another DNA fragment of approximately 1.2 kb was amplified by PCR using primer sequences corresponding to amino acid 87 to 480. This DNA fragment encodes the C-terminal half of the TG domain of PBP 1B. The primers used were 5'-primer TG-79 (5'-CGG ATA TCG ATC AAA AAA TTC GTA GCC G-3') which included the nucleotide sequence for the (SEQ ID NO:19 in the Sequence Listing) cleavage site for the restriction enzyme EcoRV, and 3'-primer TG-80 (5'-GCG GAT CCT TAG TCG ACG ACC ACA ATC GCA G-3') which (SEQ ID NO:20 in the Sequence Listing) included the sequence for BamHI cleavage.

Step 2: The PCR amplification of this fragment was done using the ponB gene on pBS96 (Broome-Smith et al., 1985) DNA as template. The amplified fragment was cloned into the EcoRV-BamHI sites of pBR 329 (Covarrubias et al., 1982) using standard protocols. The recombinant plasmid obtained was labelled pARC0534 (FIG. 8).

Step 3: The 200 bp NcoI-NruI fragment cloned in pARC0547 was excised as a NcoI-NruI fragment and cloned into NcoI-EcoRV cleaved pARC0534 to obtain pARC0551 (FIG. 8).

The mutant ponB gene on pARC0551 has DNA sequences coding for the N-terminal 64 amino acids of PBP 1B fused to the nucleotide sequences encoding the amino acids 88 to 480. A 1.3 kb PstI-BamHI DNA fragment of pBS96 was then ligated to PstI-BamHI cleaved pARC0551 and the ligation mixture transformed into *E.coli* DH5α using standard procedures. Individual transformants were then screened and colonies harbouring recombinant plasmid with the expected structure identified. The plasmid was labelled pARC0552. A NcoI-BamHI fragment from pARC0552 encompassing the entire mutant ponB gene was then excised and ligated to the T7 expression vector pARC038' to obtain pARC0559 (NCIMB 40667; FIG. 9).

The 3'-end of the cloned fragment of Step 1 has the nucleotide sequence TCG (partial NruI site sequence) while the 5'-end of the fragment cloned in Step 2 has the sequence ATC (partial EcoRV cleavage sequence). The junction nucleotide sequence which is the outcome of the fusion of TCG and ATC results in the introduction of the codons for serine and isoleucine. Thus the mutant ponB gene encodes a PBP 1B with the amino acid sequence 1 to 64 corresponding to the wild type PBP 1B fused to the sequence 87 to 844. The two stretches are joined by the amino acids serine and isoleucine.

The nucleotide sequence of the mutant ponB gene is shown as SEQ ID NO: 3 and the derived amino acid as SEQ ID NO: 4.

2.2. Expression of Soluble PBP 1B

The plasmid DNA of pARC0559 was transformed into the T7 expression host *E.coli* BL 26 (DE3) and the restriction map profile of the transformed plasmid confirmed using standard procedures. *E.coli* BL26 (DE3)/pARC0559 were grown at 22° C. And induced with 0.01 mnM IPTG and the cells allowed to grow for 6 hours. Cells were then harvested and broken by passage through a french press. The lysate was centrifuged at 10,000 rpm for 10 minutes and the supernatant obtained was centrifuged at 200,000×g for 45 minutes in a Beckman ultracentrifuge.

2.3. Characterization of the Expressed Soluble PBP 1B

The obtained supernatant, i.e. the cytosolic/soluble fraction, was tested for the presence of the mutant PBP 1B using [$^{125}$I]ampicillin as the radio-ligand. The [$^{125}$I] ampicillin was prepared as described by Rojo et al. (1984) for the preparation of [$^{125}$I]cephradine. The mutant PBP 1B was detected in the soluble fraction and bound radioactive ampicillin.

Soluble PBP 1B could also be purified using Ampicillin-Affigel beads by a procedure analogous to the one described in Section 1.4. The protein profile of the different fractions seen by Coomassie Blue staining and the binding of [$^{125}$I] ampicillin of the enriched PBP 1B fraction is shown in FIG. 10.

The purified protein was enzymatically active in the peptidoglycan transglycosylase assay (Heijenoort et al., 1992) and bound penicillin with an affinity comparable to that of the membrane bound native PBP 1B.

Example 3

3.1. Construction of Gene Encoding Soluble Form of *Streptococcus pneumoniae* PBP 1A The molecular architecture of the *S.pneumoniae* PBP 1A is predicted to be similar to that of *E.coli* PBP 1A and PBP 1B protein in the fact that the protein is anchored to the membrane via a N-terminal membrane anchoring sequence. The nucleotide sequence of the gene encoding native membrane bound *S.pneumoniae* PBP 1A and its derived amino acid sequence are described in Martin et al., (1992). The hydropathicity profile of the N-terminal 100 amino acids as derived by the Kyte and Doolittle plot is shown in FIG. 11. A stretch of 38 amino acids contributed significantly to the hydrophobicity of this region and was assumed to be the membrane interacting domain. A mutant gene of *S.pneumoniae PBP* 1A was constructed by deleting the nucleotide sequence coding for the N-terminal 38 amino acids of *S.pneumoniae* PBP 1A.

Using standard PCR protocols, sequences encoding the wild type *S.pneumoniae PBP* 1A gene was amplified as a 2.5 kb DNA fragment from the chromosome of *S.pneumoniae* strain PM1 (obtained from S. A. Lacks, Biology Department, Brookhaven National Laboratory, Upton, N.Y., USA) (Lacks, 1968) using the primers designed based on the sequence reported by Martin et al. (1992) and the amplified fragment cloned into the pneunmococcal vector pLS 101 (Balganesh and Lacks, 1984).

The mutant gene encoding a soluble form of *S.pneumoniae* PBP 1A was constructed by using of plasmid DNA harbouring the wild type gene as template and amplifying a 2.3 kb DNA fragment by using PCR following standard procedures. The sequence of the primers used were 5'-primer TG-24 (5'-TAC GTT ACC ATG GCT CCT AGC CTA TCC-3') and 3'-primer (SEQ ID NO:21 in the sequence Listing) TG-25 (5'-GAC AGG ATC CTG AGA AGA TGT CTT CTC A-3'). (SEQ ID NO:22 in the sequence Listing)

The 5'-primer TG-24 includes the sequence for the restriction enzyme NcoI while the 3'-primer TG-25 includes the site for the restriction enzyme BamHI. The NcoI and BamHI digested PCR amplified DNA fragment was ligated to NcoI-BamHI cleaved pARC039. The plasmid pARC039 is a derivative of pET 8c (Studier et al., 1990) in which the gene coding for the β-lactamase has been replaced by a kanamycin resistance cartridge.

Following ligation and screening using standard protocols, the structure of the recombinant plasmid was confirmed by detailed restriction mapping and transformed into the T7 expression host *E.coli* BL 21 (DE3) (Studier et al., 1990). The recombinant plasmid was labelled pARC0512 (NCIMB 40665) and is schematically represented in FIG. 12.

The nucleotide sequence of the mutant *S.pneumoniae* PBP 1A gene is shown as SEQ ID NO: 5 and the derived amino acid sequence is shown as SEQ ID NO: 6.

3.2. Expression and Characterization of Soluble Form of *Streptococcus pneumoniae* PBP 1A.

The gene coding for soluble *S.pneumoniae* PBP 1A was expressed by a procedure analogous to the one described in Section 1.2. The cytosolic fraction of *E.coli* BL 21 (DE3)/ pARC0512 was isolated and tested for the presence of the soluble form of the *S.pneumoniae* PBP 1Adel38. The radioactive ligand used for the binding studies was [$^3$H]benzyl penicillin (Amersham) which was prepared as described earlier. Approximately 50% of the expressed protein from the mutant gene was found to be in the soluble fraction and bound [$^{125}$I]penicillin (Rojo et al., 1984) or [$^3$H]penicillin (Amersham) when the culture was grown and induced at 22° C. with 0.01 mM IPTG. The growth and induction conditions were critical for the efficient recovery of the soluble protein, as growth at higher temperatures or induction with higher concentrations of IPTG resulted in the majority of the protein becoming inactive and forming inclusion bodies. Optimum levels of soluble active protein was found following induction for 6–8 h. (FIG. 13).

The soluble *S.pneumoniae* PBP 1Adel38 protein could also be efficiently purified essentially following the protocol used for the purification of the soluble *E.coli* PBP 1B protein.

The efficiency of penicillin binding of the soluble PBP 1Adel38 was comparable to that of the native membrane bound *S.pneumoniae* PBP 1A.

Example 4

4.1. Transglycosylase Deficient *E.coli* PBP 1B

The conserved amino acids within Region 2 (FIG. 14) were chosen for site-directed mutagenesis. Within this stretch of 10 amino acids three different mutations were constructed:

(a) the glutamines at position 270 and 271 of the PBP 1B sequence were changed to alanines;

(b) the glutamines at position 270 and 271 of the PBP 1B sequence were changed to leucines; and (c) a deletion of the nucleotide sequence encoding amino acids from position 264 to 271.

Mutants of the ponB gene were constructed essentially following the procedure of Kunkel et al. (1985). A 1.5 kb EcoRI-SalI fragment of the ponB gene of the plasmid pBS96 was excised and cloned into EcoRI-SalI cleaved M13mp19 following standard protocols.

(a) The primer used for mutating the nucleotide sequence coding for glutamine residues 270 and 271 into a sequence coding for alanine residues was TG-21:

(SEQ ID NO:23 in the Sequence Listing)

```
5'-ACG CTG ACG GCC GCT CTG GTG AAA-3'
    T   L   T   A   A   L   V   K
```

(b) The primer used for mutating the sequence coding for the glutamine residues 270 and 271 into leucine residues was TG-23:

```
5'-ACG CTG ACG CTA TTG CTG GTG AAA-3'  (SEQ ID NO:25 in the Sequence Listing)
    T   L   T   L   L   L   V   K      (SEQ ID NO:26 in the Sequence Listing
```

(c) The primer used for creating a deletion of the nucleotides encoding amino acids at position 264 to 271, all of which are within the conserved Region 2, was TG-22:

```
5'-CGC ACG GTA CAG CTG GTG AAA AAC-3'

R   T   V   Q   L   V   K (SEQ ID NO:27 in the Sequence Listing)

260 261 262 263 272 273 274 (amino acid no.)(SEQ ID NO:28 in the Sequence Listing)
```

Following mutagenesis, the nucleotide sequence of the mutagenized EcoRI-SalI fragment was determined following the protocol of Sanger et al. (1977). The sequencing confirmed the nucleotide changes and also ruled out any extraneous changes. This mutated 1.5 kb DNA fragment was ligated back to EcoRI-SalI cleaved pBS96 and the ligated DNA transformed in to *E.coli* DH5α cells following standard protocols. Kanamycin resistant transformants were analyzed for their plasmid profiles and the plasmid with the TG-21 mutation (a) was labelled pARC0438 (NCIMB40661). The mutant protein is referred to as PBP 1B QQ-AA (SEQ ID NO: 7).

The plasmid with the mutation (b) introduced by TG-23 was labelled pARC0468 (NCIMB 40662). The mutant protein is referred to as PBP 1B QQ-LL (SEQ ID NO: 8)

The plasmid with the deletion (c) obtained using TG-22 was labelled pARC0469 (NCIMB 40663). The mutant protein is referred to as PBP 1Bdel8 (SEQ ID NO: 9).

The four plasmid DNAs of pBS96, pARC0438, pARC0468 and pARC0469 were individually transformed into *E.coli* ponB:spc$^r$ cells (Broome-Smith et al., 1985) in which a deleted ponB gene had been marked with spectinomycin resistance marker.

*E.coli* ponB:spc$^r$ cells having the individual plasmids pBS96, pARC0438 or pARC0469 were grown and membrane preparations made following the procedure described by Spratt (1977) and the profile of the penicillin binding proteins analyzed on a 8% SDS-PAGE following labelling with radioactive penicillin. The mutant proteins were initially analyzed for its vivo stability and localization into the membrane using anti-PBP 1B sera raised against purified membrane bound native PBP 1B (FIG. 15).

The mutant proteins were found to be localized to the membrane and no degraded protein fragments reacting with the antibody could be detected indicating no gross instability. In addition the mutant proteins bound penicillin with an affinity comparable to that of the wild type PBP 1B (FIG. 15).

After assaying for transglycosylase activity as described in Heijenoort et al. (1978), no activity could be detected in the membranes expressing the mutant proteins, while the membrane with the wild type PBP 1B showed transglycosylase activity. This defines the amino acids 263 to 271 as being critical for transglycosylase activity.

The ability of the mutant proteins to bind penicillin with an affinity comparable to that of the wild type suggests that the transpeptidase activity of the mutant proteins would also be comparable to that of the wild type. Knowing that the bifunctional protein PBP 1B expressed on a plasmid can in trans complement the deletions of both ponA and ponB (Yousif et al., 1985) the ability of the transglycosylase negative/transpeptidase positive proteins PBP 1B QQ-AA and PBP 1Bdel8 to complement the absence of chromosomally encoded PBP 1A and 1B was tested.

The wild type ponB and the mutant ponB genes were cloned into low copy vector pMAK 705 (Hamilton et al., 1989). The resulting plasmids were designated pARC0462, (wild type ponB, FIG. 16), pARC0463, (ponBdel8, FIG. 17) and pARC0470 (ponB QQ-AA, FIG. 18). The plasmids were individually transformed into *E.coli* del ponA (*E.coli* with a deletion of the ponA gene).

*E.coli* del ponA/pARC0462, *E.coli* del ponA/pARC0463 and *E.coli* del ponA/pARC0470 were used as recipients of the P1 phage for the transduction of the ponB:spc$^r$ marker. The transduction was performed as described by Miller (1972) The phage P1 lysate was made on *E.coli* ponB:spc$^r$ strain (Yousif et al., 1985). Following infection, the infected cells were plated on spectinomycin. Integration of the DNA fragment harbouring and ponB:spc$^r$ transduced into any of the recipients results in the inactivation of the chromosomal ponB gene rendering the chromosome ponA$^-$ and ponB$^-$. This genotype being lethal for the cell, the *E.coli* spectinomycin resistant transductants can remain viable only if the plasmid encoded ponB or the ponB mutant can functionally complement in trans.

The following *E.coli* strains were subject to phage P1 transduction analysis of trans-complementation: (1) *E.coli* AMA 1004 which has chromosomally coded with type ponA and ponB; (2) *E.coli* AMA 1004 which has a chromosomally inactivated ponB and is the host for the plasmid coded mutant ponB genes; (3) *E.coli* AMA 1004 host bearing the plasmid pARC0462 encoding the wild type ponB gene; (4) *E.coli* AMA 1004 host bearing the plasmid pARC0463 encoding PBP 1Bdel8; and (5) *E.coli* AMA 1004 host bearing the plasmid pARC0470 encoding PBP 1B QQ-AA.

| Results | (Number of Km$^r$ transductants / ml) |
|---|---|
| (1) *E.coli* AMA 1004 | 3.0 × 10$^4$ |
| (2) *E.coli* AMA 1004, ponB:spc$^r$ | <1 |
| (3) *E.coli* AMA 1004, ponB:spc$^r$ (PBP 1B wt) | 1.1 × 10$^4$ |
| (4) *E.coli* AMA 1004, ponB:spc$^r$ (PBP 1Bdel8) | <1 |
| (5) *E.coli* AMA 1004, ponB:spc$^r$ (PBP 1B QQ-AA) | <1 |

A comparable number of transductants were obtained for an internal marker: trp transduction using the same P1 phage lysate.

The above results show that viable transductants could be obtained only with wild type PBP 1B, indicating that the TG⁻ TP⁺ product encoded by ponB QQ-AA or ponBdel8 could not complement the loss of chromosomally encoded PBP 1A and 1B. However, as these mutant proteins bind penicillin and thus can be assumed to have transpeptidase activity, the inability to complement must be the absence of the transglycosylase enzymic activity. These results confirm the essential nature of the transglycosylase activity of PBP 1A or 1B for the viability of the E.coli cell.

The mutants described define the Region 2 to be involved in the transglycosylase activity of the protein. As this stretch of amino acids is conserved within the four high molecular weight penicillin binding proteins namely E.coli PBP 1A, 1B and S.pneumoniae 1A and the 94 kDa protein of H.influenzae (FIG. 14) it is reasonable to assume similar catalytic or structural involvement of this region in all the transglycosylase enzymes utilizing substrates similar to that used by PBP 1A and 1B of E.coli.

4.2. Transglycosylase Deficient E.coli PBP 1A

The conserved Region 2 was chosen for site-directed mutagenesis and the nucleotide sequence coding for glutamine at positions 123 and 124 of E.coli PBP 1A was changed to a sequence coding for alanine by PCR mutagenesis as follows. The 5' half of the ponA gene was amplified as 2 fragments, the 5'-fragment corresponding to amino acid 1 to 123 (fragment A) and the 3'-fragment corresponding to amino acid 124 to 434 (fragment B).

The sequence of the 5'-primer used for the amplification of fragment A was TG-93 (5'- GCG CGG ACC ATG GTG AAG TTC GTA AAG TAT-3') (SEQ ID NO:29 in the sequence Listing) while the 3'-primer used for the amplification of fragment A was TG-106 (5'-CAG TGC TGC ACT AAT GGT ACT TGC CCC TTG-3'). (SEQ ID NO:30 in the Sequence Listing).

The 3'-primer for fragment A amplification included the sequence for the restriction enzyme PstI which allowed the conversion of the sequence encoding the glutamine residues in position 123 and 124 into a nucleotide sequence coding for alanine residues.

Fragment B was amplified with the 5'-primer TG-107 (5'-ATT ACT GCA GCA CTG GCG AGA AAC TTC TTC-3') and the 3'-primer TG-108 (5'-TCG (SEQ ID NO:31 in the Sequence Listing). CGA GAT ATC TGG CGG ATT GAT CGA CAC-3'). (SEQ ID NO:32 in the Sequence Listing).

The 5'-primer for amplifying fragment B included the sequence for the restriction enzyme PstI overlapping the sequence with that of 3'-primer for amplifying fragment A. Ligation of the 3'-end of fragment A to the 5'-end of fragment B recreated the site for PstI and resulted in the change of the nucleotide sequence encoding glutamine 123 and 124 into alanine 123 and 124. The amplified fragments A and B were individually cloned into pBR 329, and corresponding clones pARC0565 and pARC0566 were obtained.

Fragment A and B obtained from pARC0565 and pARC0566 were ligated to obtain pARC0567. The ponA sequences were completed by introducing an XhoI-BamHI fragment of pARC0489 (which is identical to pARC0558 (FIG. 3) except for having additional LacI and Lac operator sequences) into pARC0567 to obtain pARC0568. The MluI-BglII fragment of pARC0568 which included the $Q_{123}$–$Q_{124}$ to $A_{123}$–$A_{124}$ mutated region was then used to replace the otherwise identical MluI-BglII fragment of pBS98 to obtain the plasmid pARC0571 (FIG. 19; NCIMB 40668). The mutant protein was labelled PBP 1A QQ-AA (SEQ ID NO: 10).

Expression studies on the mutant indicated that the mutant protein was localised to the membrane (as detected by anti PBP 1A antibodies) and bound penicillin with an affinity comparable to that of the native PBP 1A (FIG. 20).

An in vivo complementation assay, similar to that described in the previous section, was performed by checking the ability of mutant PBP 1A protein to complement in trans. The in vivo complementation was performed using phage P1 transduction and transducing ponB:spc$^r$ into the host E.coli (recipient) del ponA harbouring the plasmid encoding the mutant protein PBP 1A QQ-AA.

In order to carry out the complementation analysis the wild type ponA gene was cloned into the low copy vector pMAK 705 (Hamilton et al, 1989) to obtain pARC0583 and the mutant ponA gene encoding PBP 1A QQ-AA cloned into pMAK 705 to obtain pARC0582.

The following E.coli strains were subject to phage P1 transduction analysis of trans-complementation: (1) E.coli AMA 1004 which has chromosomally coded ponA and ponB; (2) E.coli AMA 1004 ponA which has a chromosomally inactivated ponA and is the host for the plasmid coded mutant ponA genes; (3) host bearing the plasmid pARC0583 encoding the wild type ponA gene; (4) host bearing the plasmid pARC0582 encoding PBP 1A QQ-AA.

| Results | (Number of Spc$^r$ transductants / ml) |
|---|---|
| (1) E.coli AMA 1004 | 2.1 × 10³ |
| (2) E.coli AMA 1004, ponA | <1 |
| (3) E.coli AMA 1004, ponA (PBP 1A wt) | 1.64 × 10³ |
| (4) E.coli AMA 1004, ponA (PBP 1A QQ-AA) | <1 |

A comparable number of transductants were obtained for internal marker: trp transduction using the same P1 phage lysate.

As shown above, no viable transductants could be obtained with E.coli del ponA/pARC0582 as recipient indicating that the mutant PBP 1A QQ-AA could not complement the absence of chromosomally encoded PBP 1A/1B. This indicates that the $Q_{123}$ and $Q_{124}$ of region 2 of PBP 1A also affects transglycosylase activity of the protein as the loss of the complementing function must be a reflection of the loss of transglycosylase activity. The transpeptidase activity of the protein is unaffected as tested by its affinity to bind penicillin.

These results argue in favour of the region 2 as a critical stretch of amino acids involved in the transglycosylase enzymic function and may be the explanation for the strong evolutionary conservation of this stretch of amino acids.

Example 5

5.1. Truncated E.coli PBP 1B

A mutant gene encoding the truncated PBP 1B consisting of the N-terminal 553 amino acids was constructed by PCR amplification using the 5'-primer TG-77 (5'-GAA AAA CCA TGG CCG GGA ATG ACC-3') and the 3'-(SEQ ID NO:33 in the Sequence Listing). Primer TG-116 (5'- ATG GGA TCC TTA ATC ATT CTG CGG TGA-3'). (SEQ ID NO:34 in the Sequence Listing).

The 5' end of the primer corresponded to the amino acid 553 in the wild type followed by the stop codon and a site for the restriction enzyme BamHI. A fragment of 1.7 kb was amplified using pBS96 DNA as template. The PCR amplified fragment was cut with PstI and BamHI and cloned into PstI-BamHI restricted pARC0555 (pARC0555 has the full length ponB gene cloned as NcoI-BamHI fragment into the expression vector pET11d. The NcoI site includes the initiation codon ATG) to obtain pARC0592 (NCIMB 40669; FIG. 21) The expressed protein (SEQ ID NO: 11) was shown to have transglycosylase activity, thus confirming the functional independence of this domain.

```
5'-TCG AGG ATC CCC ATG GGC CTA TAC CGC TAC CGC TAC ATC G-3'  (SEQ ID NO:37 in the Sequence Listing)
    ========  ========
    EcoRI     BamHI
```

The soluble truncated PBP 1B, i.e. PBP 1B with N-terminial 553 amino acids but lacking the membrane anchoring hydrophobic domain from 65–87, was constructed by replacing the PstI-BamHI fragment of pARC0559 (FIG. 9) with the PstI-BamHI fragment of pARC0592 to obtain pARC0593 (NCIMB 40670; FIG. 22). The mutant ponB gene encodes the soluble form of PBP 1B and the expressed protein (SEQ ID NO: 12) was found to have transglycosylase activity.

5.2. Minimum Substrate Binding Domain of Truncated *E.coli* PBP 1B

Detailed computer analysis of the anatomy of the presumptive TG domain (aa 1–553) of PBP 1B indicated that aa 210–368 were probably sufficient for the binding of the lipid linked substrate and the transglycosylase reaction. This stretch of amino acids includes the 3 conserved domains Region I, II and III. The mutant gene encoding the truncated protein stretch 210–368 was constructed as follows.

A fragment of approx size 480 bp was amplified from pBS96 as substrate with the 5'-primer having the sequence TG-154 (5'-CAA TCC ATG GGT GAG CAG CGT CTG TTT G-3') were the initiation ATG codon is (SEQ ID NO:35 in the Sequence Listing). immediately followed by the sequence encoding the 210th amino acid of PBP 1B.

The 3'-primer corresponded to the sequence TG-155 (5'-T CCA GAA TTC CAG TTT TGG GTT ACG-3') were the sequence encoded the amino acid (SEQ ID NO:36 in the Sequence Listing). 368 of PBP 1B followed by the nucleotide sequence that provide the restriction site for EcoRI, enabling fusion to sequences encoding an enterokinase site and a histidine stretch, which allows rapid purification of the protein on an Ni affinity column (cf. section 6.2 below).

A NcoI-EcoRI fragment was cloned into the plasnmid pARC0400 that was restricted with NcoI-EcoRI to obtain the recombinant plasmid pARC0392 (NCIMB 40659; FIG. 23). The recombinant plasmid was transformed into *E.coli* BL26 (DE3) and a protein of approximately 17 kDa was detected largely in the soluble fraction after induction with IPTG.

Along similar lines the minimum substrate binding region of PBP 1A could be predicted to involve the stretch 62–220 in the wild type protein. Production of this protein as a fusion with a histidine stretch allows high efficiency affinity purification of the expressed product using the Ni$^{2+}$ column. That the results will be similar to that obtained with truncated PBP 1B can be anticipated.

Example 6

6.1. N-terminal Fusion of Soluble *E.coli* PBP 1A to Glutathione-S-transferase

Fusion of the ponAdel23 gene at its 5'-end in frame to sequences coding for glutathione-S-transferase was made as described in the following section.

The vector chosen for the fusion gene construction was pGEX-3X obtained from Pharmacia Biochemicals. In order to fuse the 5'-initiation ATG of ponAdel23 in frame with the gene encoding glutathione-S-transferase a BamHI site was introduced using a PCR primer whose sequence included the sequence for the restriction enzyme EcoRI. The 5'-primer used was TG-115:

The 3'-primer used was TG-106, described in Section 4.2. The PCR amplified DNA Fragment A was digested with BamHI and PstI and cloned into the BamHI-PstI sites of the standard cloning vector pUC8 to obtain pARC0496. This Fragment A includes the N-terminal 102 amino acids of the PBP 1Adel23 protein. A BamHI-MluI (site present within the fragment A) 270 bp fragment obtained from Fragment A, a 2.2 kb MluI-EcoRI fragment which includes the rest of the portion of the ponA gene obtained from pARC0490 (pARC0490 has the wild type ponA gene cloned into the XbaI-BamHI sites of the low copy vector pWKS29 (Fu Wang et al., 1991) facilitating the 3'-end of the ponA del 23 gene to be excised as an EcoRI fragment) and a EcoRI-BamHI cleaved pGEX-3X were ligated together and transformed into competent *E.coli* cells. Individual transformants were screened for recombinant plasmid and the plasmid with the expected structure was designated pARC0499 (NCIMB 40664; FIG. 24). The encoded fusion product on pARC0499 has the glutathione-S-transferase sequences at its C-terminus linked to PBP 1Adel23 sequences via a Factor Xa cleavage recognition sequence.

Following induction with 1 mM IPTG, a fusion protein of expected size was found to be induced. The protein bound penicillin and was active in the transglycosylase assay. Following cell lysis by passing the suspension through a French press, the cell free supernatant fraction was prepared as detailed in Section 1.4. for the purification of PBP 1Adel23. The supernatant fraction was passed through a Glutathione Sepharose® matrix (Pharmacia Biochemicals) and the bound GST-PBP 1Adel123 was eluted with glutathione. The eluted protein was found to be 80% homogeneous. Free glutathione was removed by dialysis and the GST-PBP 1Adel 23 was cleaved with factor Xa.

PBP 1Adel23 thus purified was found to be active in both penicillin binding and the transglycosylase reactions.

6.2. C-terminal Fusion of Soluble *E.coli* PBP 1A to Histidine Stretch

Fusion of the ponAdel23 gene at its 3'-end in frame to sequences encoding a stretch of 6 histidines was made as described below.

In the first step the ponAdel23 gene was amplified using pBS98 DNA as template using the 5'-primer TG-115 (5'-TCG AGG ATC CCC ATG GGC CTA TAC CGC TAC ATC G-3') and the 3'-primer TTG-121 (5'-GTT AGA (SEQ ID NO:37 in the Sequence Listing). ATT CGA ACA ATT CCT GTG-3'). (SEQ ID NO:38 in the Sequence Listing).

The 3'-primer introduced an EcoRI site at the 3' end of the ponAdel23 gene while eliminating the translation stop codon. The PCR amplified modified ponAdel23 gene fragment was digested with PstI and EcoRI to release a 930 bp 5'-end fragment and ligated to PstI-EcoRI digested pBR 329 to obtain the recombinant plasmid pARC0467.

In the next step, a double stranded synthetic oligonucleotide with sequences encoding the six histidines and the DNA sequence coding for amino acids recognised as the enterokinase cleavage site was synthesised and ligated to the newly created EcoRI site at the 3'-end of the ponAdel23 gene on pARC0467. The synthetic oligonucleotides used were TG-122:

```
       EcoRI
       ------
5'-AA TTC GAC GAC GAC GAC AAG CAC CAC CAC CAC CAC CAC TGA TAA G-3  (SEQ ID NO:39 in the Sequence Listing)
      ------------------======================
         ENTEROKINASE         HISTIDINES
``` and TG 123 (5'-GAT CCT TAT CAG TGG TGG TGG TGG TGG TGC TTG TCG TCG TCG TCG-3'). (SEQ ID NO: 40 in the Sequence Listing)

The plasmid pARC0467 was linearised with EcoRI and the synthetic double stranded oligonucleotide ligated. Following ligation a PstI-BamHI (Fragment A) was released from the ligation mixture and cloned into the PstI-BamHI sites of pARC0558 (FIG. 3), to obtain pARC0400 (NCIMB 40660; FIG. 25). The mutant ponAdel23 fusion gene thus encoded a protein with the PBP 1Adel23 sequence fused to the amino acid sequence Asp -Asp-Asp-Asp-Lys fused to His-His-His-His-His-His at its C-terminus. The (SEQ ID NO:41 in the Sequence Listing). Asp-Asp-Asp-Asp-Lys sequence is recognised by the protease enterokinase (SEQ ID NO:41 in the Sequence Listing). And cleaves following the lysine residue. The six histidine residues confer on the protein the ability to bind to the metal nickel.

The recombinant plasmid pARC0400 was transformed in *E.coli* BL26(DE3) cells and induced under culture and temperature conditions identical to those used for the purification of PBP 1Adel23. The cells were lysed by passing through a French press. The lysate was centrifuged at 10,000 rpm for 10 min. The supernatant obtained after low speed centrifugation was then spun at 200,000× g for 45 min and the supernatant obtained represented the cytosolic fraction. This fraction contained the protein encoded by the fusion gene and the recombinant fusion protein was labelled PBP 1Adel23EH. This protein PBP 1Adel23EH bound [$^{125}$I] cephradine and was also active in transglycosylase assay. The soluble fraction was passed through a Ni affinity column and bound protein eluted in batches with increasing concentrations of imidazole essentially following the procedure described in "The Qia Expressionist" obtained from QIAGEN Inc. 9259 Eton Avenue, Chateworth, Calif. 91311 USA. The majority of PBP 1Adel23EH eluted with 250 mM imidazole and was approximately 85% homogenous. It was the only cephradine binding protein eluted from the column. Thus the ability of fusion protein to bind to the Ni column can be easily exploited both for efficient purification and immobilization of the active protein.

Example 7

7.1. Use of cell extracts for enzyme assays and in screening

The crude cell extract made according to Example 6 can be analyzed for the ability to bind penicillin by reacting with [$^3$H]ampicillin prepared according to Hackenbeck (1983). To adapt the procedure to large-scale screening, a 96 well microtiter plate is used to contain the reactions and the assay is performed using a Beckman Biomek robot. Crude cell extract is mixed with [$^3$H]ampicillin for 15 min at 37° C. The proteins in the reactionare are precipitated with TCA and collected on a glass filter, unbound ampicillin is washed off and filters counted in a scintillation counter. Alternatively, autoradiography can be used to assay the degree of binding of ampicillin.

Based on the above method, a competitive assay can be used to assess the ability of test compounds to bind to the transpeptidase site of a PBP variant. In this assay, the test compound is exposed to the crude cell extract for 15 min prior to the addition of ampicillin. A positive result is indicated by a reduction in the amount of radioactivity present on the glass filter.

7.2. Use of Soluble Immobilised Protein in Screening

Protein containing a histidine peptide which has been purified as described can be used for screening for compounds which inhibit transpeptidase activity or transglycosylase activity. The purified full length or truncated protein is immobilised onto agarose gel to which Ni(II) has been coupled. Aliquots of the beads containing immobilised protein are then transferred to the wells of a microtiter plate, test compounds are added to the plate and incubated before unbound test substance is washed free. Compounds which bind to the transpeptidase site of the bifunctional protein can be detected by adding [$^3$H]ampicillin to the reaction vessel and continuing essentially as described above. Alternatively monoclonal antibodies known to bind to the transpeptidase region can be used. Compounds which bind to the transglycosylase site can be assessed in a competitive assay by the use of monoclonal antibodies which bind to the transglycosylase region of the protein.

Example 8

8.1. Production of Monoclonal Antibodies to PBP 1A

The protocol for the production of monoclonal antibodies (mAbs) was essentially that described in "Antibodies—a laboratory manual" (ed. Harlow David Lane, Cold Spring Harbor, USA). Purified membrane bound PBP 1A was used as the immunogen. Balb-C mice, 6–8 weeks old were immunised with 50 μg of purified native PBP 1A in Freunds Complete Adjuvant. A booster injection of 20 μg PBP 1A in incomplete Freunds adjuvant was given intraperitoneally. Two weeks later the presence of serum antibodies was checked by ELISA using PBP 1A as the coated antigen. Mice with circulating antibodies were immunised intraperitoneally daily for 4 days with 20 μg of PBP 1A in saline and the mice sacrificed for isolating splenocytes for generating fusions.

The myeloma cell line used in fusion experiments was Sp 2/0-Ag 14 and these cells were fused with splenocytes from immunised mice at an ratio of 10:1. Fusion was carried out using standard protocols and antibody production from the clones was monitored by ELISA against PBP 1A when the cells were >90% confluent.

72 high producing clones were expanded to 24 well plates and the secreted antibody characterised using the following screens: (1) ELISA against membrane bound form of PBP 1A; (2) ELISA against soluble form of PBP 1Adel 23; (3) Dot blot analysis against membrane bound PBP 1A to eliminate monoclonals reacting with the detergent solubilised purified PBP 1A protein only due to changes in the configuration during purification; and (4) ELISA against membrane bound form of PBP 1B.

Based on these screens, a panel of 5 secreting clones were selected and subcloned twice to ensure monoclonality. Ascites with these hybridoma clones were raised following standard procedures and IgG was purified from these ascites fluids, using Protein G-Sepharose® affinity chromatography as recommended by the manufacturers of Protein G-Sepharose® (Pharmacia Biochemicals).

These purified antibodies react specifically with PBP 1A in both the membrane bound and the soluble forms in ELISA, Dot blots and in Western blotting. Clones were obtained by a cloning procedure employing 3 cells/well. To ensure the monoclonality these clones were subcloned into 96 well microtiter plates by limiting dilution at 1 cell/well. The wells receiving one cell were carefully confirmed under the microscope and allowed to grow with macrophage feeder layers so as to obtain progeny from a single hybrid cell. Following sub-cloning the secretion of mAbs to PBP 1A was again assayed in ELISA using full length PBP 1A. Finally two clones from each parent hybridoma were selected and one of them was expanded as ascites in pristine primed Balb/c mice. All the five clones adapted to grow in peritoneal cavities and produced ascetic mAbs.

The ascetic mAbs were titrated against purified PBP 1A in ELISA. All the ascitic mAbs had a titre of >5×10$^5$ in ELISA and recognised full length protein in western immunoblots. The ascitic mAbs were purified by protein-G affinity columns.

The inmunoglobulin isotype of mAbs was determined by mouse Ig-isotype by ELISA using a kit obtained from Sigma chemicals USA. Four of the monoclonals belonged to IgG1 and one belonged to IgG2a immunoglobulin isotype.

Further characterization of mAbs was done by using full length membrane bound PBP 1A/1B in western blots. In addition the transglycosylase (TG) and transpeptidase (TP) domain specificity of mAbs was determined by using various truncated forms of the membrane-bound N-terminal of PBP 1A, N-terminal of PBP 1B and C-terminal of PBP 1B in Western immnunoblots. Various full length acid truncated membrane bound PBPs were expressed and the prepared membrane fractions were resolved on a SDS-PAGE. The proteins were transferred onto nitrocellulose membranes and subjected to western blot analysis using polyclonal E.coli PBP 1A antibodies and monoclonal antibodies.

Assessment of the penicillin binding inhibitory potential of the mAbs was determined essentially following the protocol described by den Blaauwen et al. (1990). The protein-G affinity purified mAbs was preincubated with PBP 1A followed by addition of [$^3$H]benzyl penicillin or [$^{125}$I] cephradine. Two of the mAbs competitively inhibited binding of the radiolabelled penicillin to PBP 1A.

Monoclonal antibodies specific for the TG domain of PBP 1A have been obtained by screening the secreted antibody of the original hybridoma clones to react with the protein representing the N-terminal 434 amino acids of PBP 1A in western blots. Antibody from clone TG-2 reacted with the N-terminal truncated 434 amino acid analogue of PBP 1A but also inhibited (>80% inhibition) the transglycosylase activity of PBP 1A. This indicates that the antibody recognises sequences in the protein which are involved in (a) binding of the substrate; (b) catalysing the enzymic action; or (c) altering conformation of the protein allosterically. In either of the three possibilities, identification of compounds competing for the binding of TG-2 to PBP 1A would represent molecules interacting with identical sequences on PBP 1A. Thus the competitive binding assay could be used as a screening assay for the identification of the TG inhibitory compound.

Figure 1:
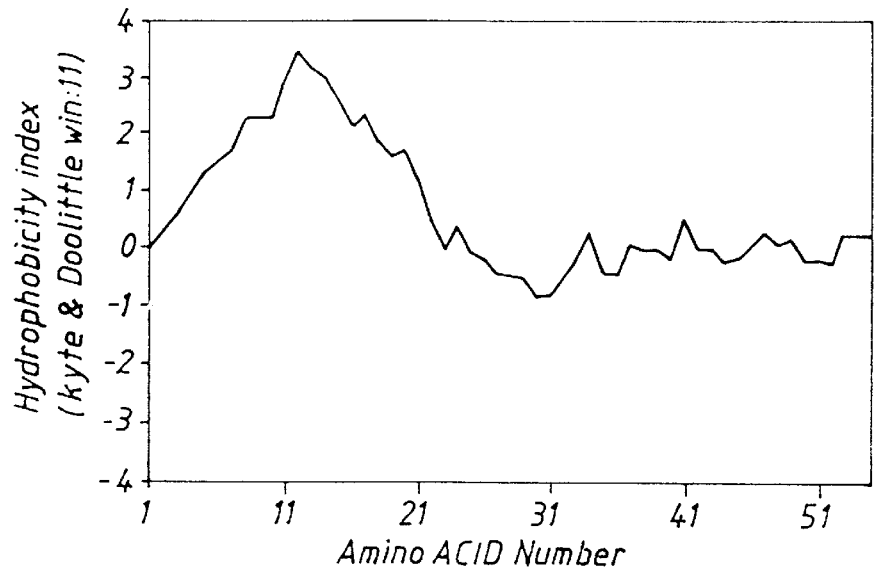
FIG. 1
Figure 2:
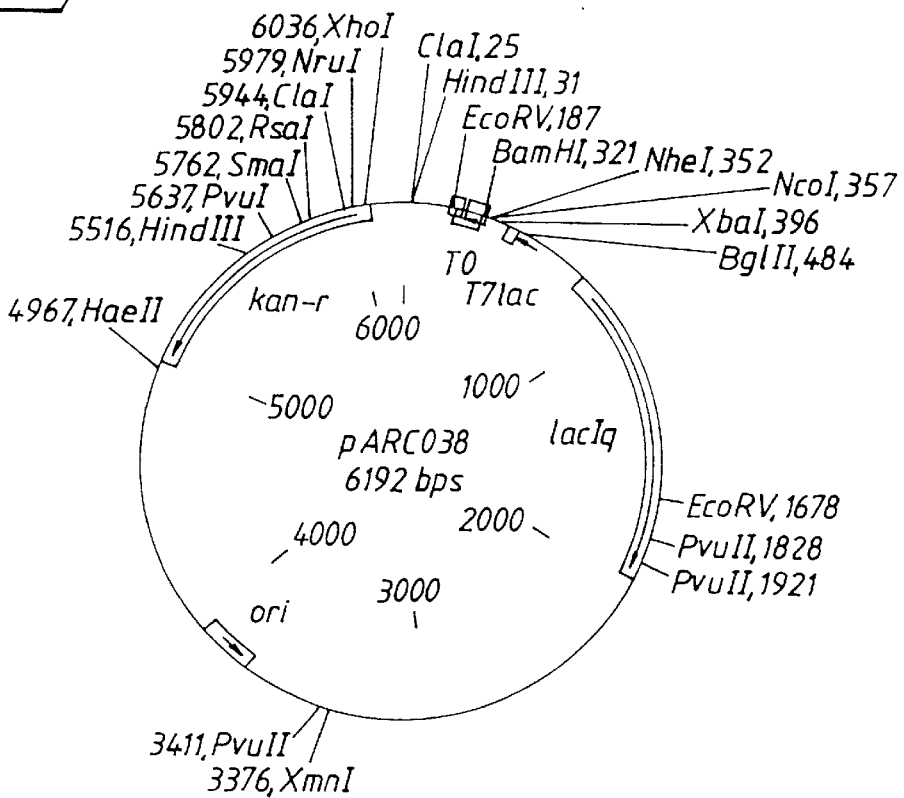
Figure 3:
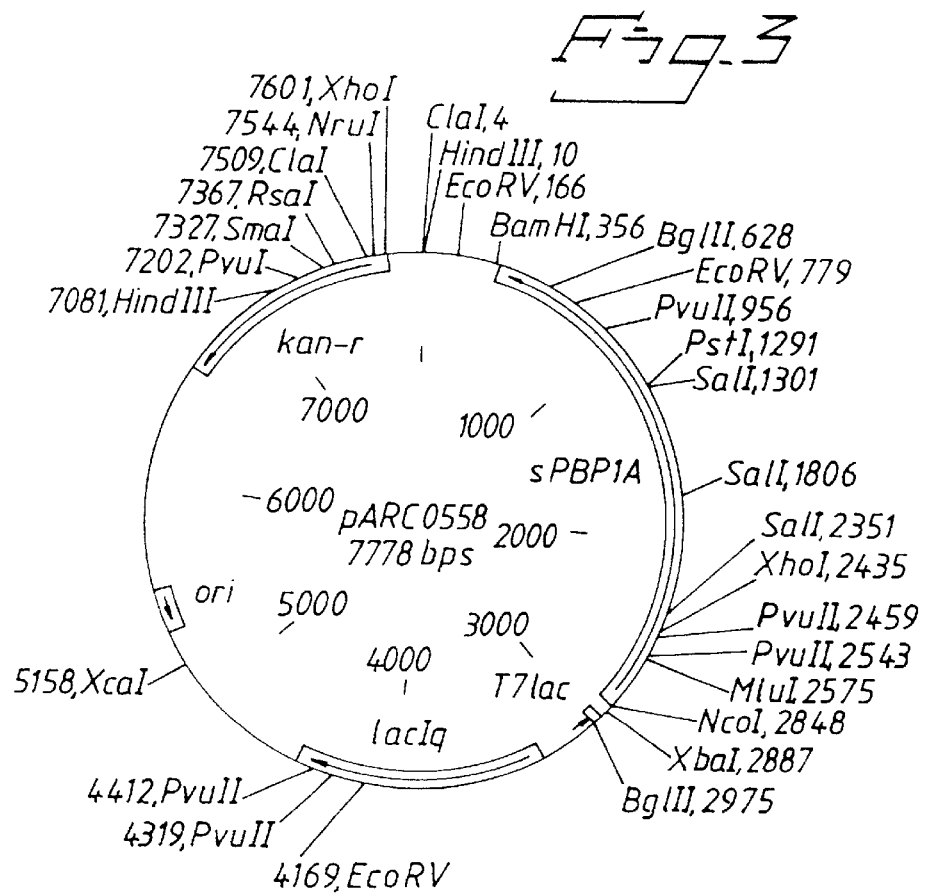
Figure 4:
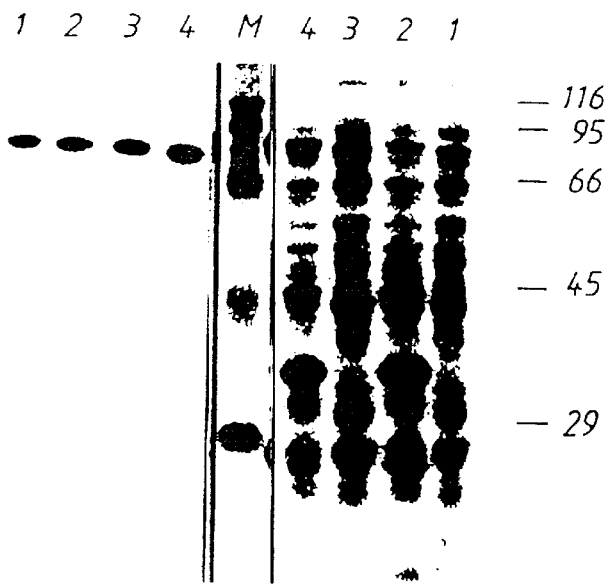
Figure 5:
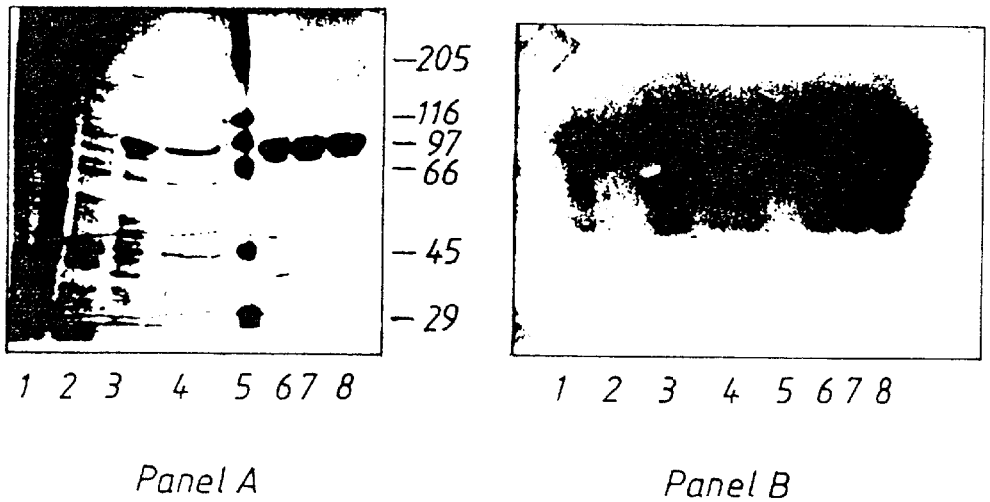
Figure 6:
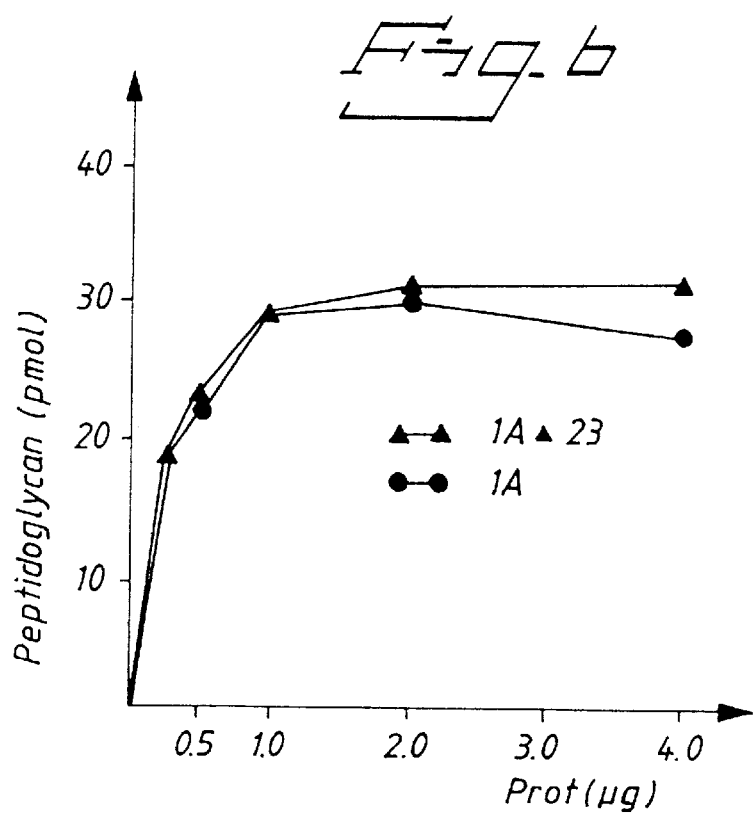
Figure 7:
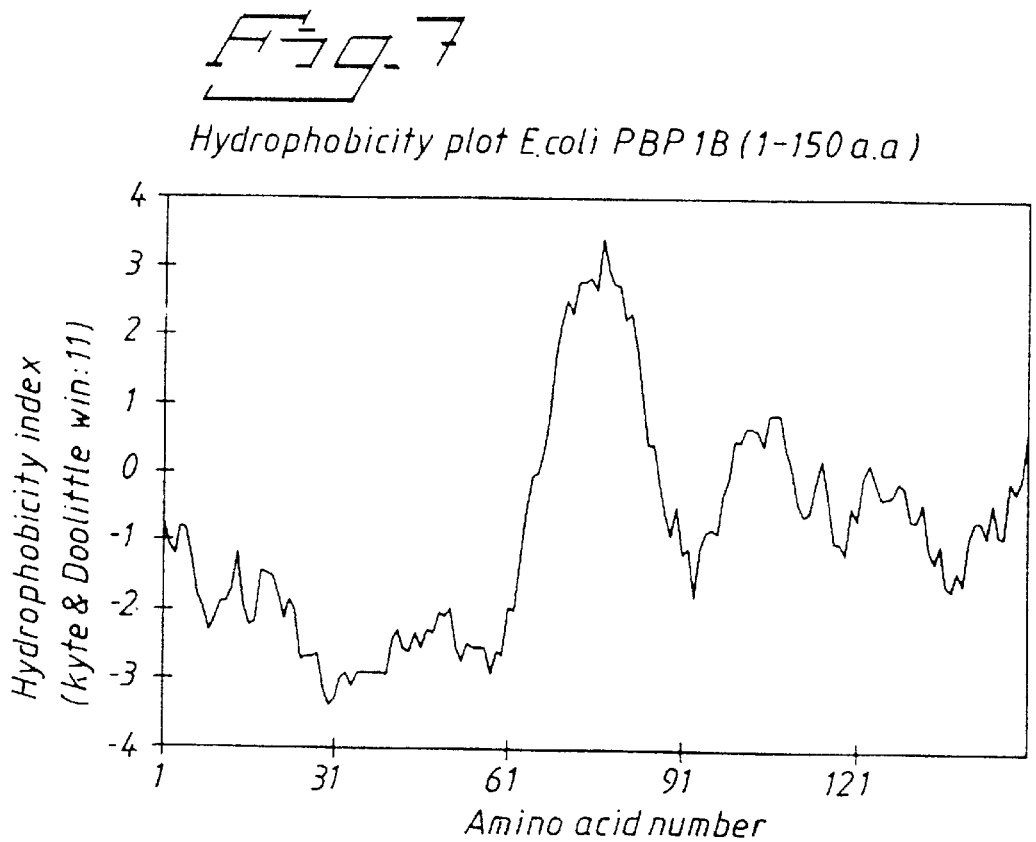
Figure 9:
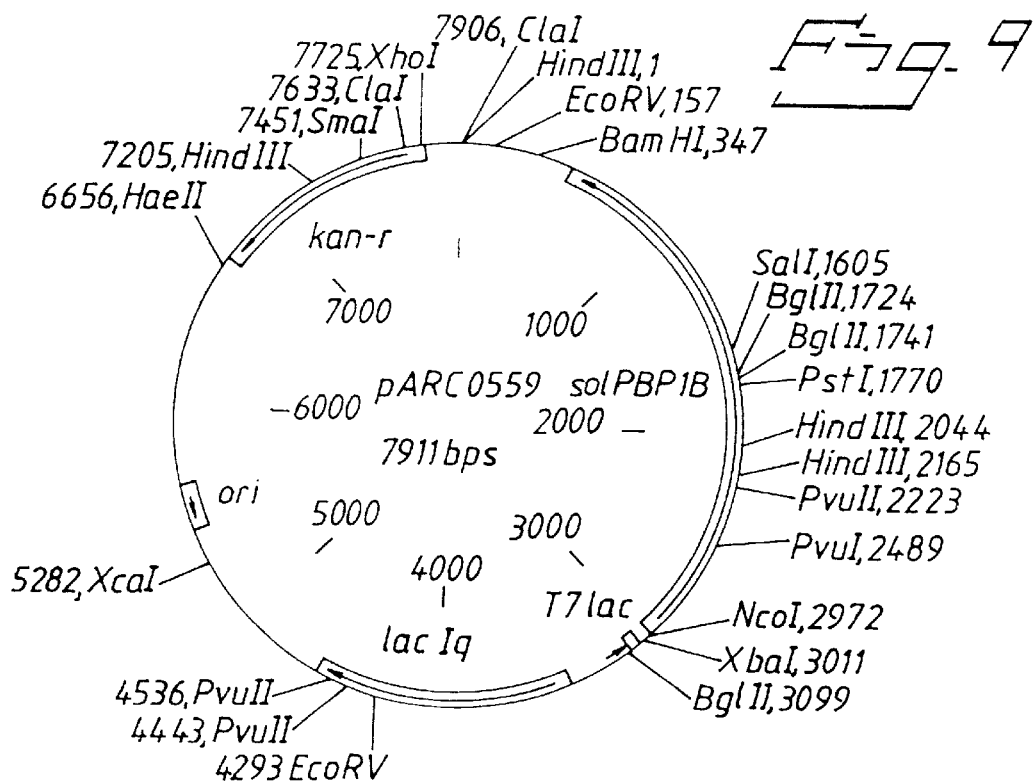
Figure 8:
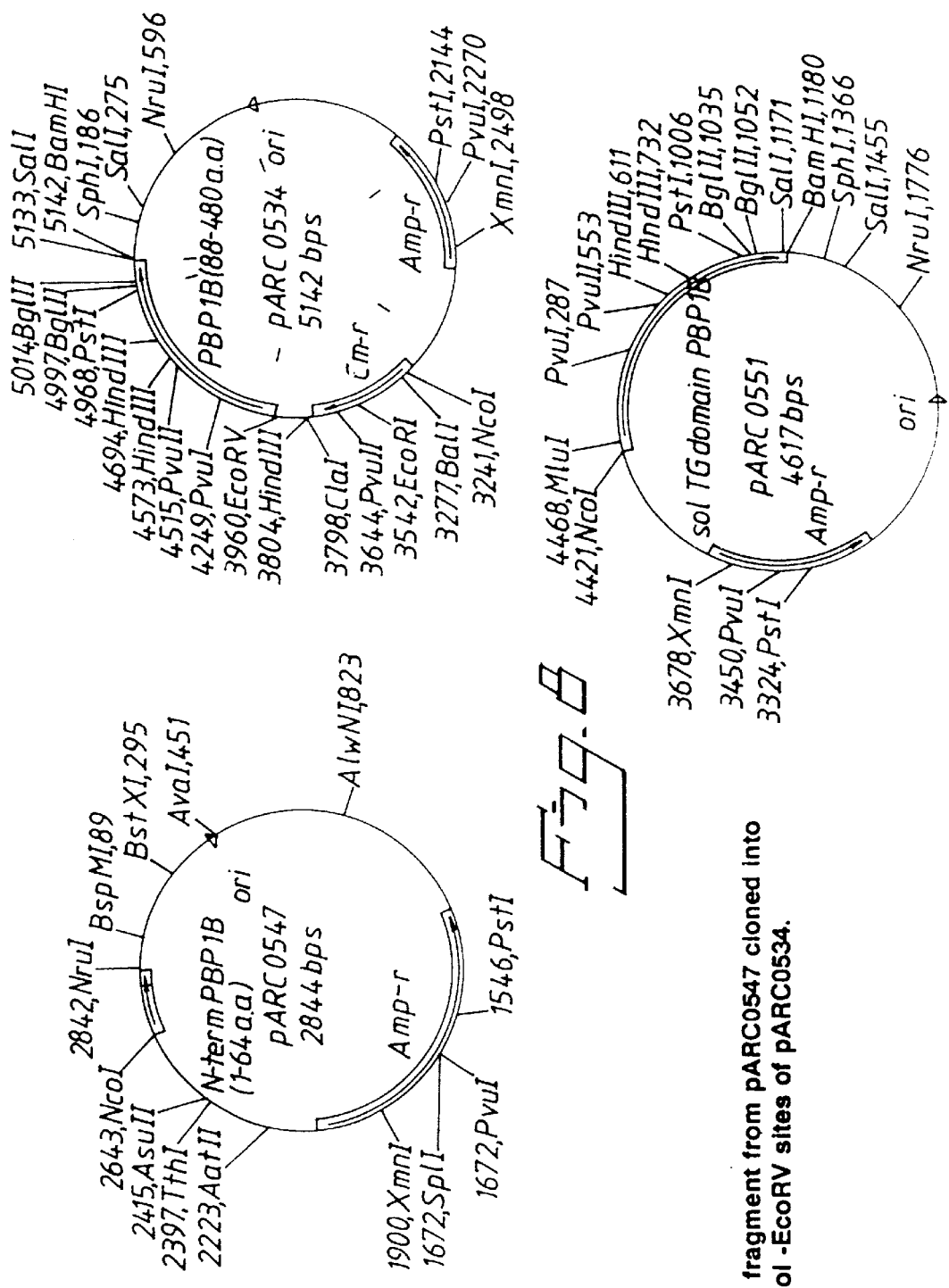
Figure 10:
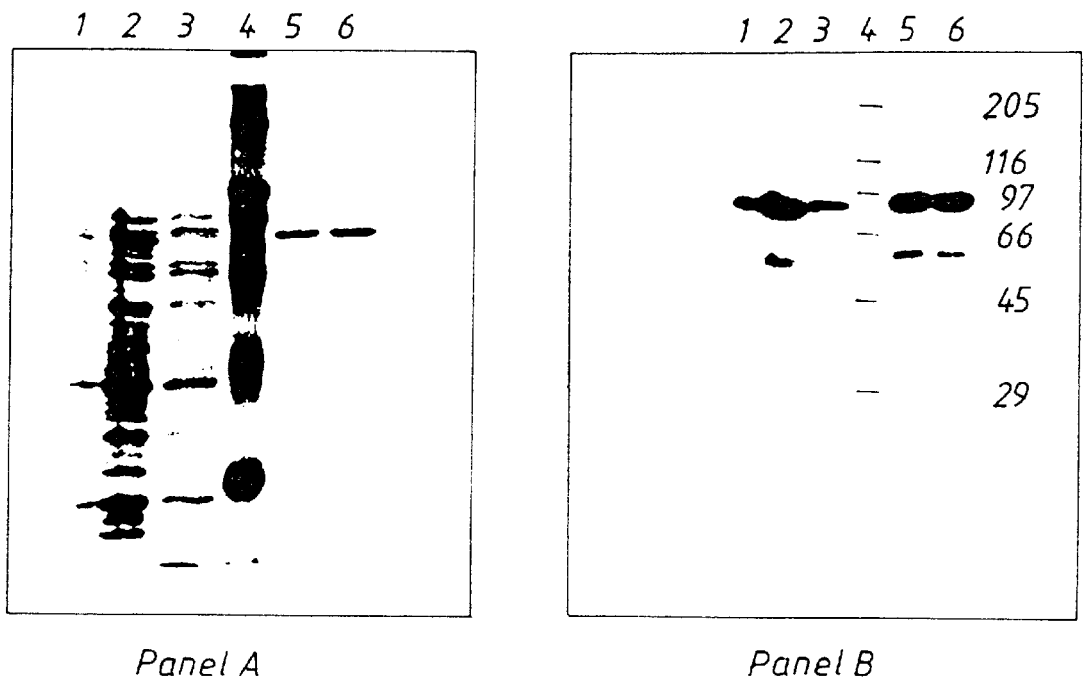
Figure 11:
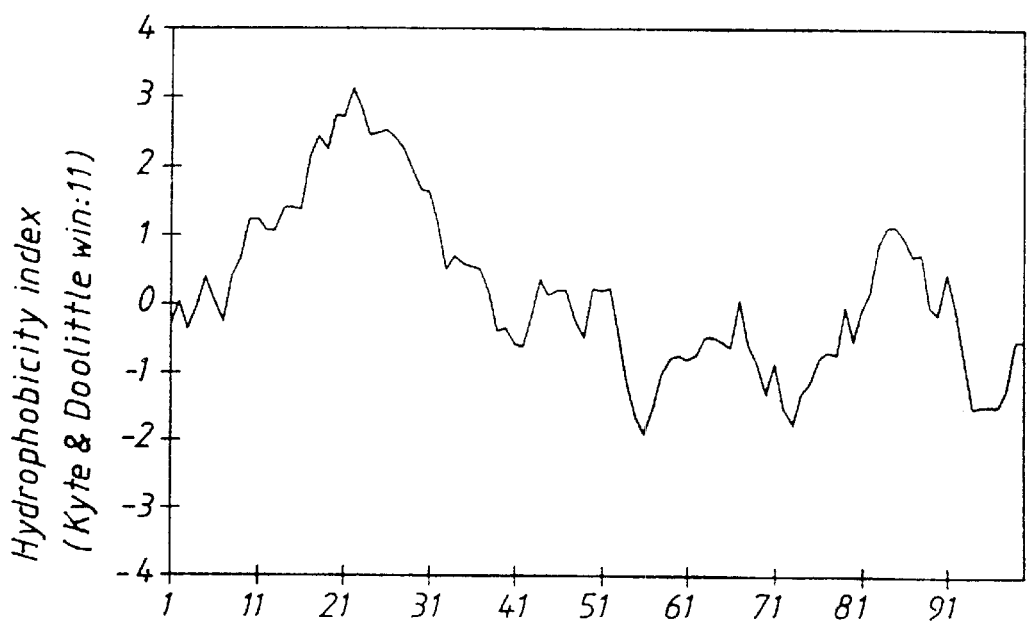
Figure 12:
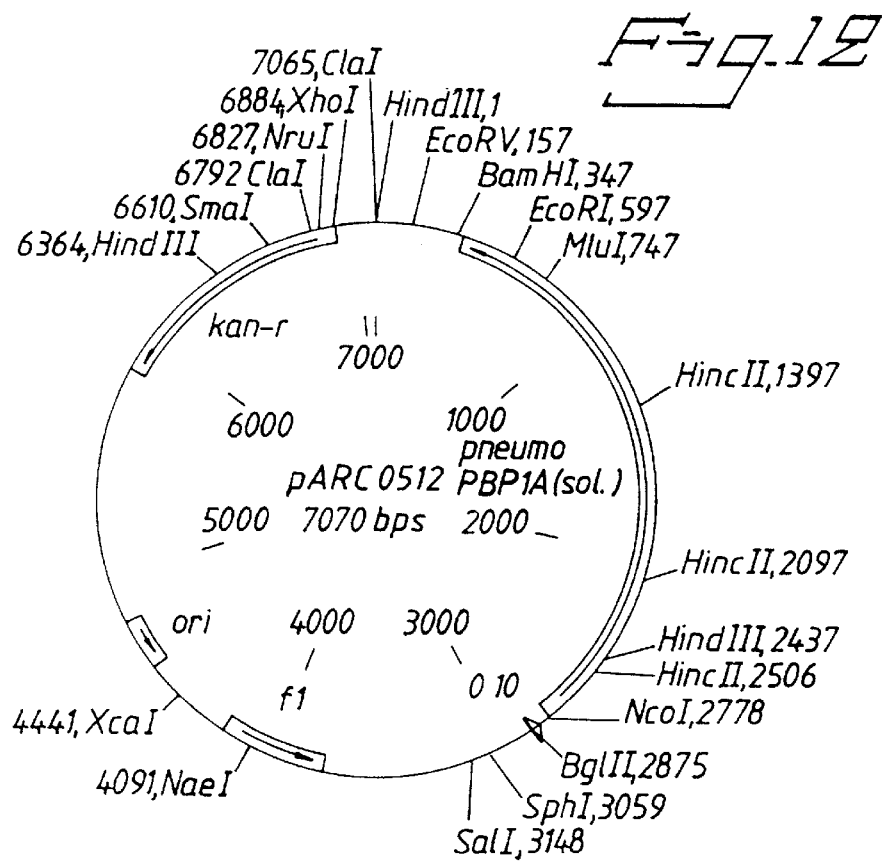
Figure 13:
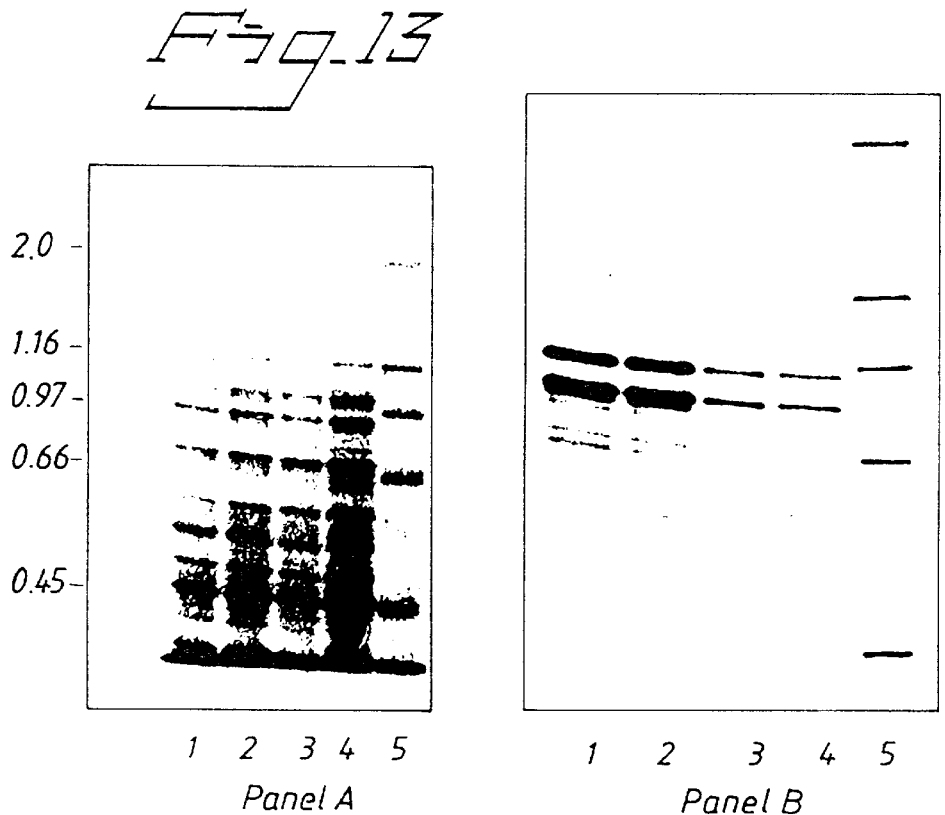
Figure 15:
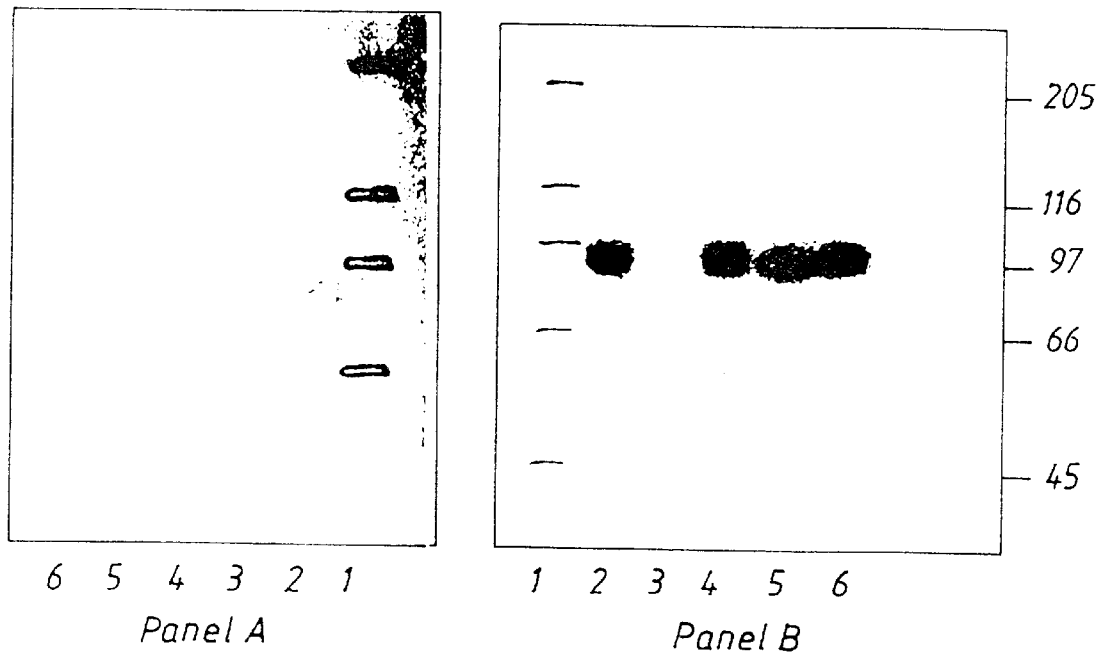
Figure 16:
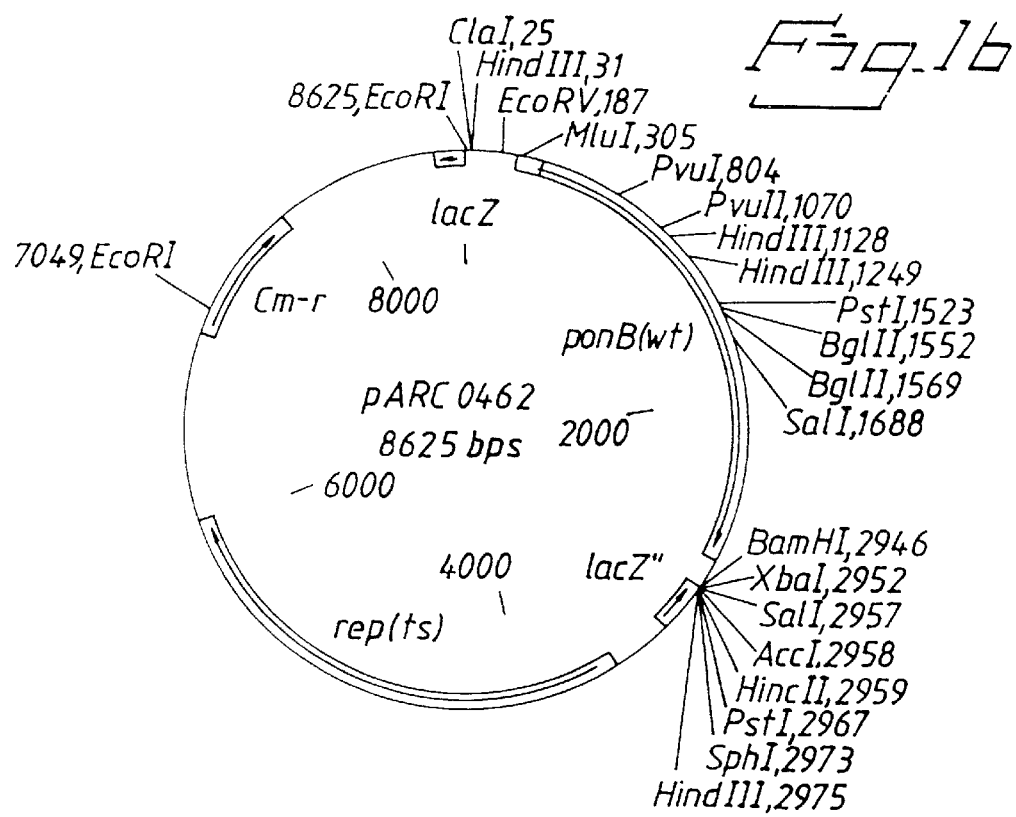
Figure 17:
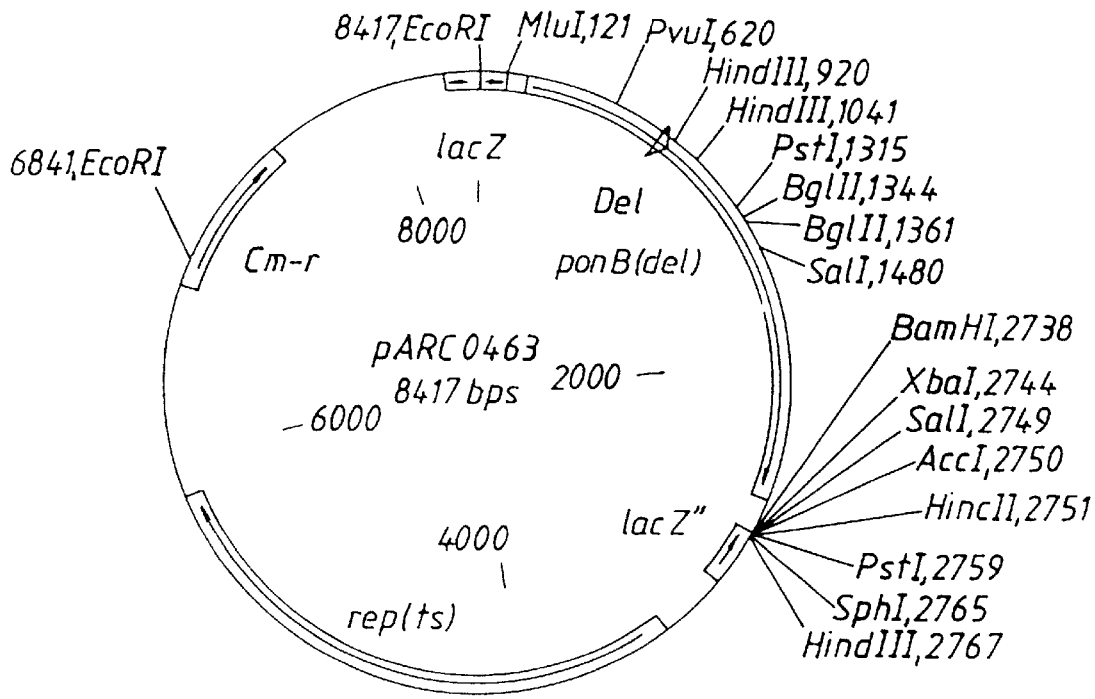
Figure 18:
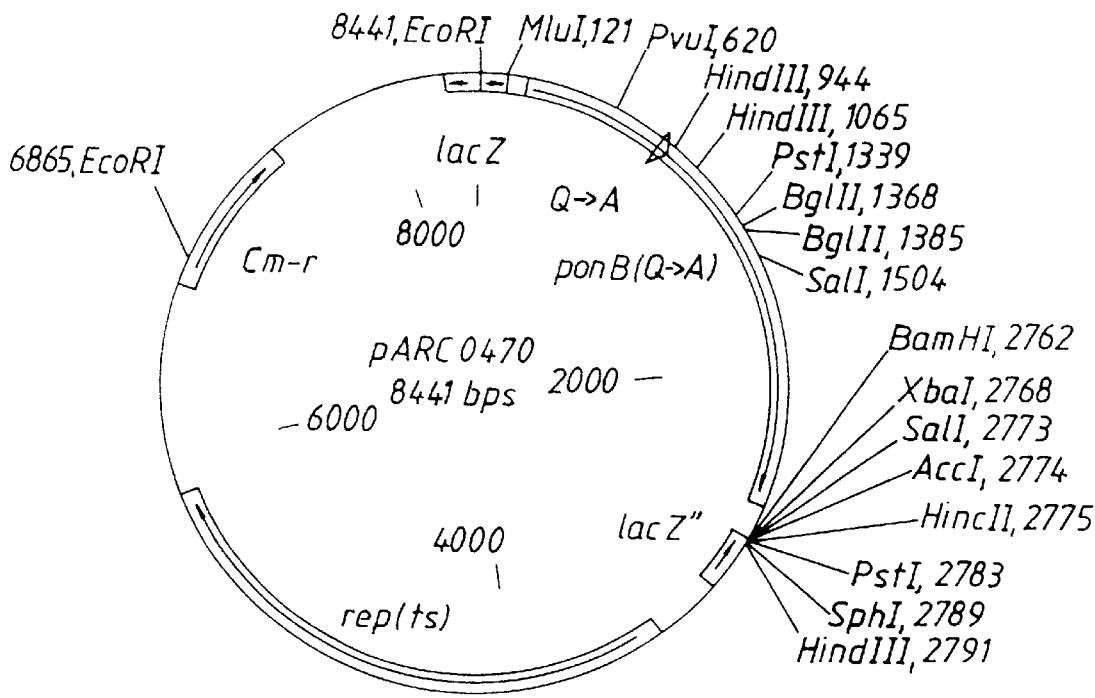
Figure 19:
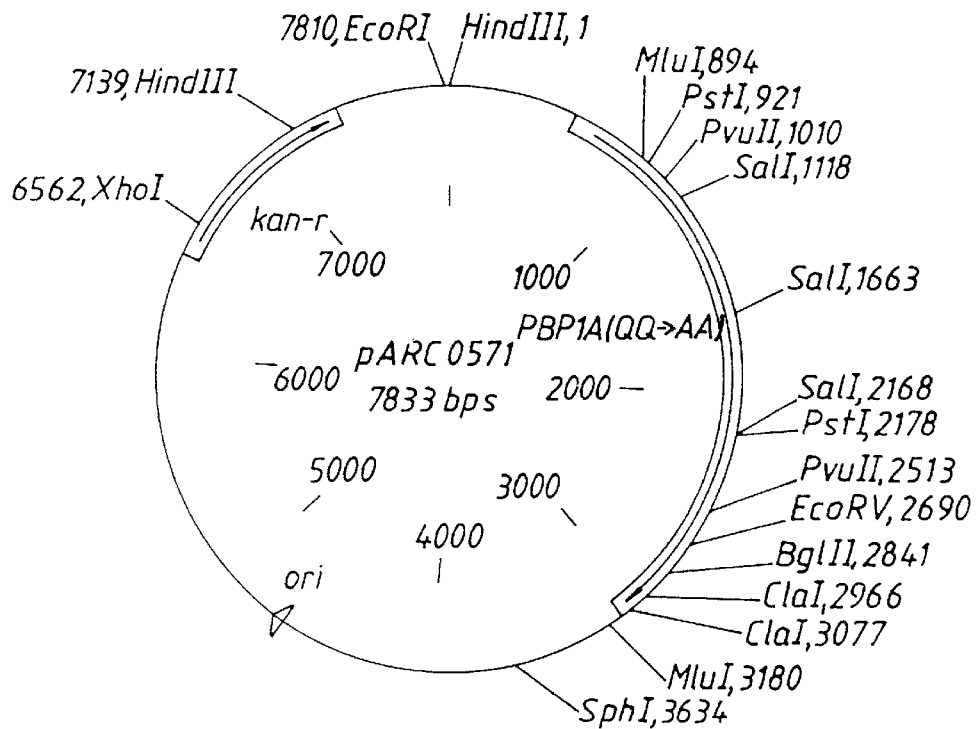
Figure 20:
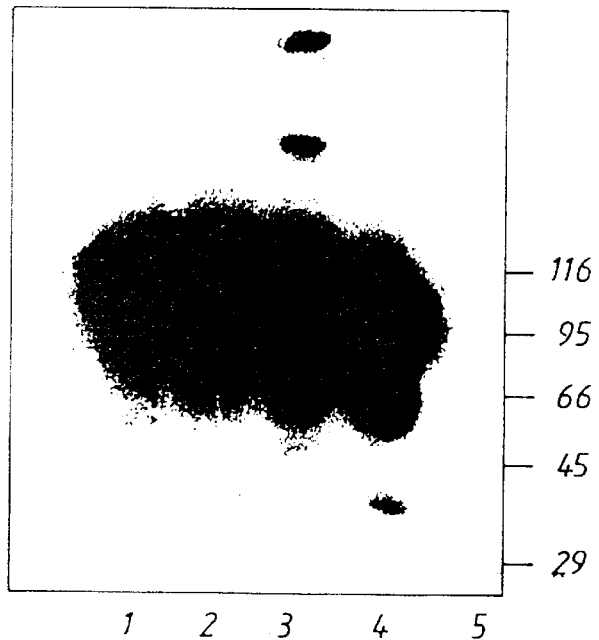
Figure 21:
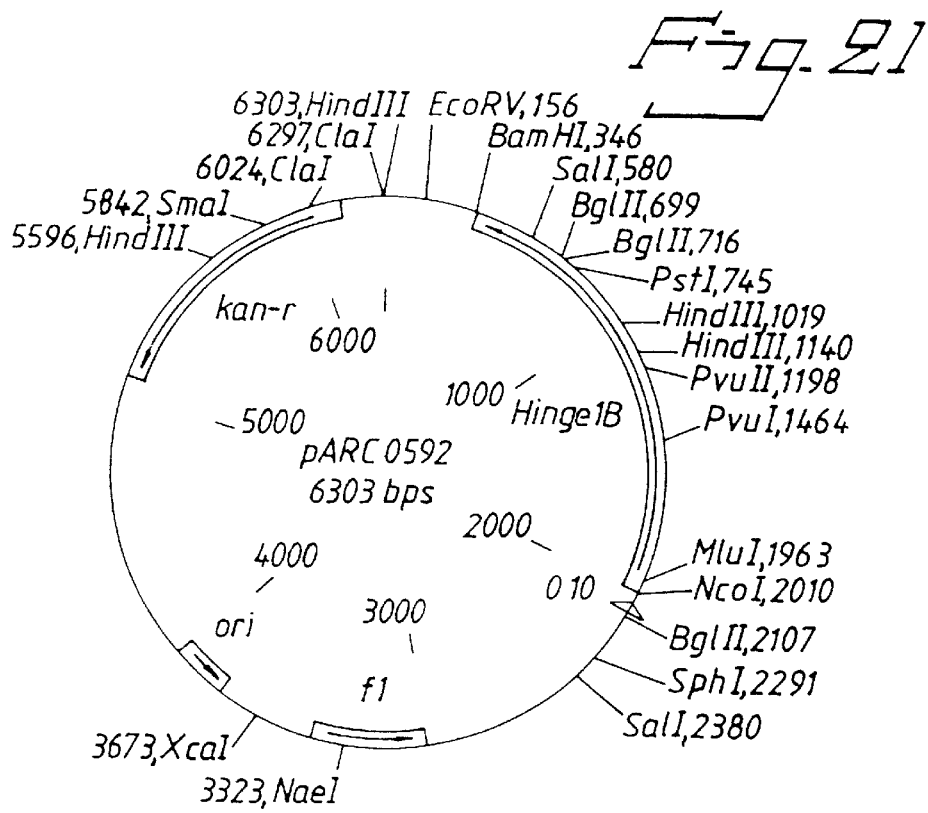
Figure 22:
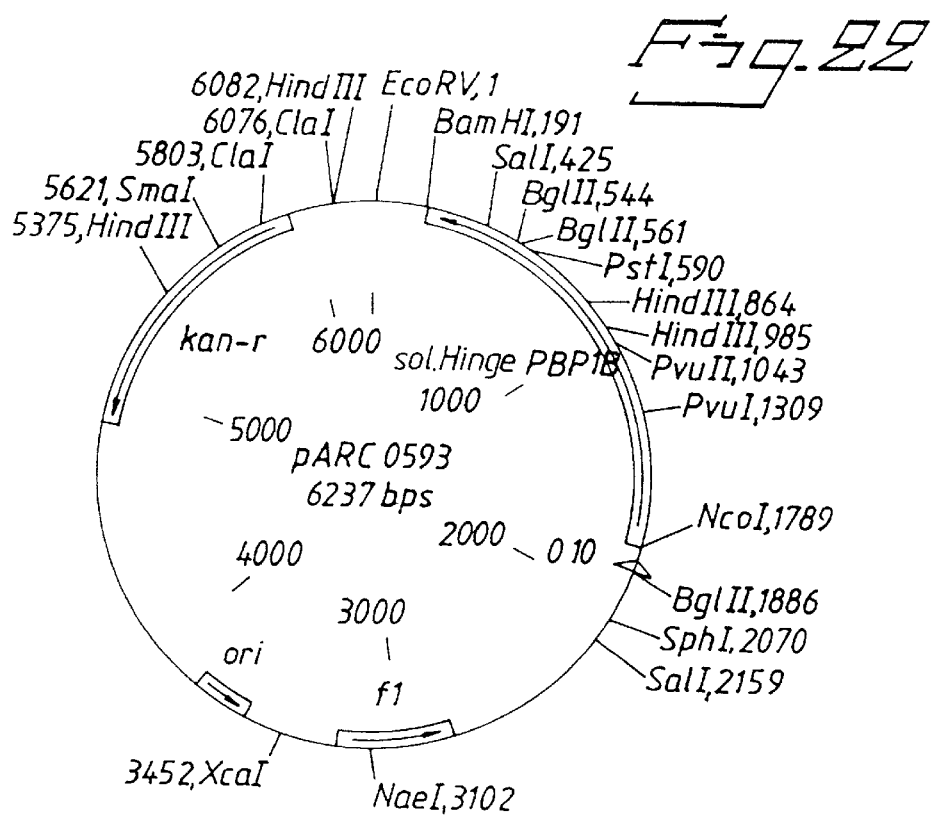
Figure 23:
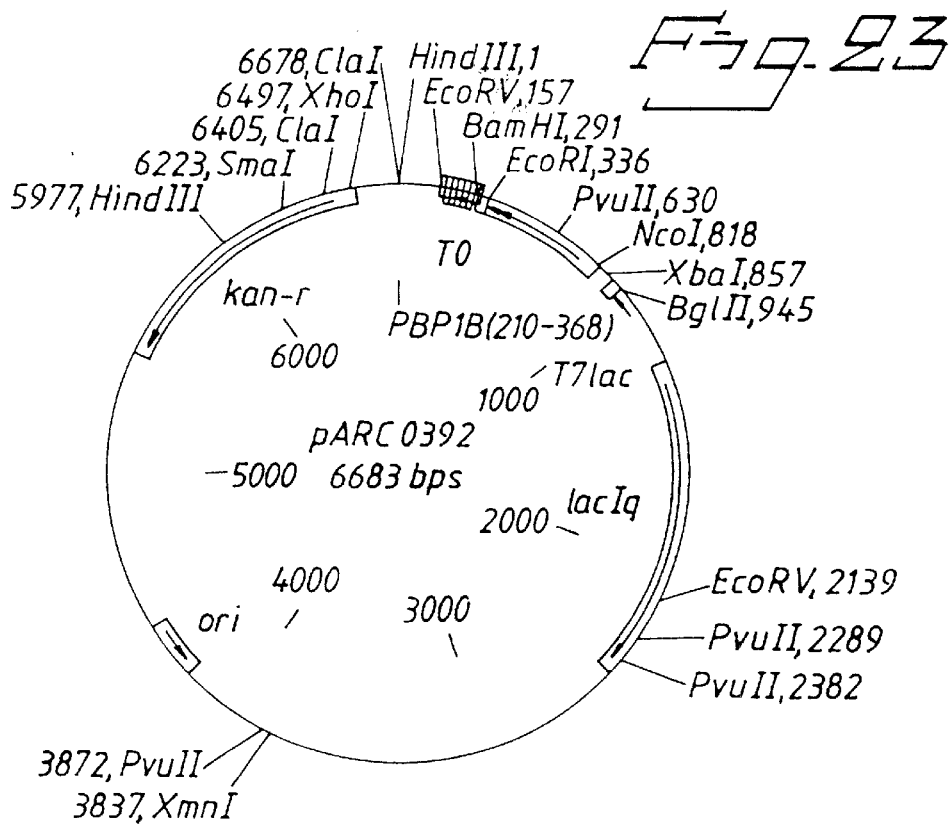
Figure 24:
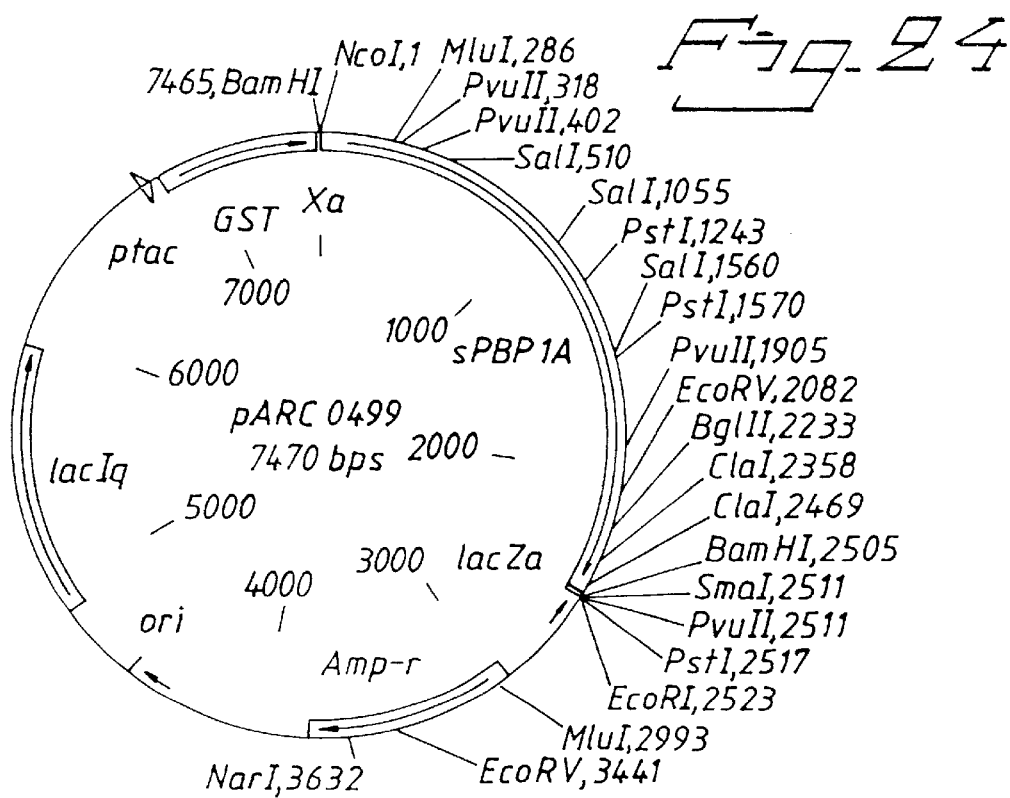
Figure 25:
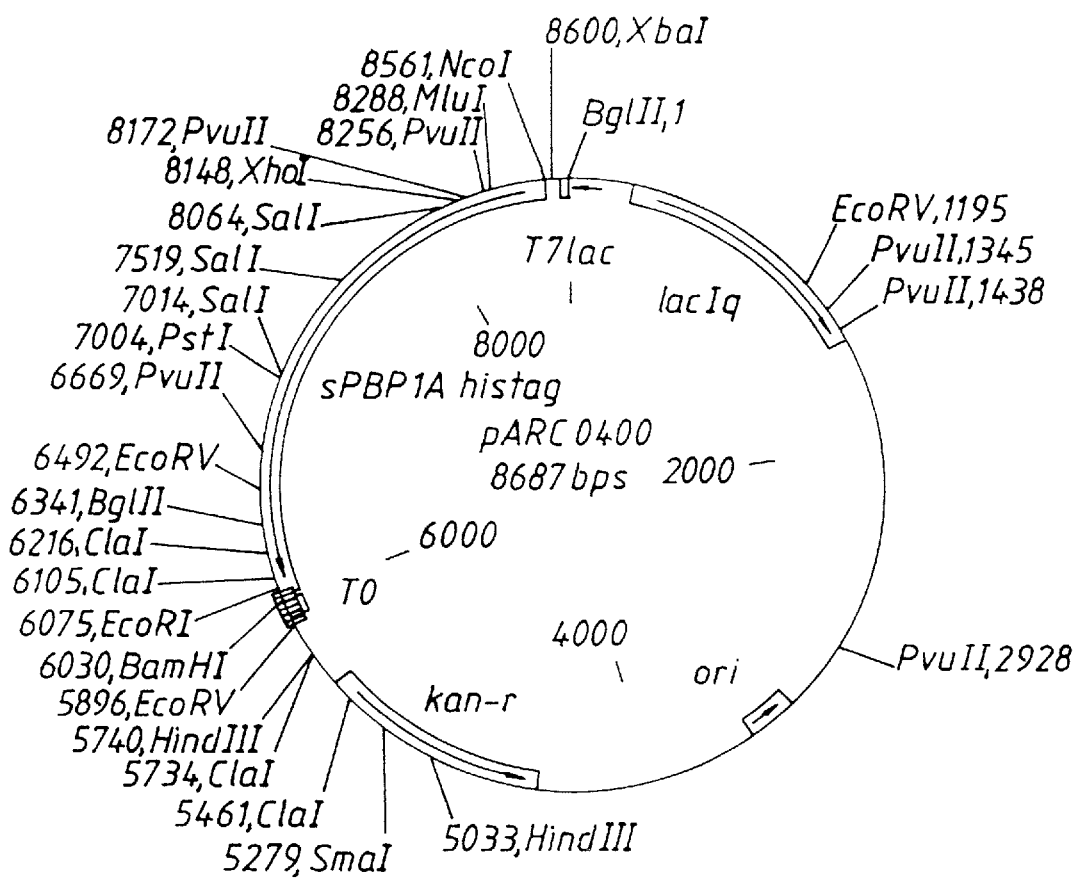

Hydropathicity profile of E.coli PBP 1A. The figure shows in expanded form the hydropathicity pattern of the N-terminal 55 amino acids of PBP 1A.

FIG. 2

Schematic representation of the T7 translation fusion expression vector pARC038.

— vector sequences

═ gene conferring kanamycin resistance Km$^r$, gene encoding the lactose repressor (lac I$_q$), origin of replication (ori), T7 lac operator promoter, T7 phage terminator.

The direction of transcription of the different genes are shown by arrows. Relevant restriction enzyme sites are shown. Numbers next to the restriction site represent the nucleotide position taking the nucleotide at the upper twelve o'clock-position as zero.

FIG. 3

Schematic representation of the vector pARC0558 encoding soluble PBP 1Adel 23 of E.coli.

— vector sequences

═ mutant gene encoding PBP 1Ade123, kanamycin resistance Km$^r$, lactose repressor (lac Iq) and the origin of replication ori.

FIG. 4

Expression of soluble PBP 1Ade123. Panel A represents the autoradiogram of the [$^{125}$I]cephradine binding profile of the uninduced and induced cultures of E.coli BL 26 (DE3) harbouring pARC0558. Panel B represents the Coomassie Brilliant Blue staining protein profile of the same uninduced and induced cells. Lane (1): uninduced cytosol fraction; (2): uninduced membrane fraction; (3): induced cytosol fraction; (4): induced membrane fraction; (M): molecular weight markers.

FIG. 5

SDS-PAGE pattern of purified PBP 1Ade123. Panel A: Coomassie blue staining. Panel B: [$^{125}$I]cephradine binding protein profile. Lanes (1): E.coli BL 26(DE3)/pARC0558 cytosolic fraction (200,000 g supernatant); (2): 30% Ammonium sulphate supernatant fraction; (3): 30% Ammonium sulphate pellet fraction; (4): Cephradine affigel breakthrough fraction; (5): Molecular weight markers; (6–8): Cephradine affigel eluate.

FIG. 6

Transglycosylase activity profile of wild type PBP 1A and mutant PBP 1Ade123 using purified proteins.

(▲—▲) represents activity of soluble PBP 1Ade123;

(●—●) represents activity of membrane bound PBP 1A solubilised with octyl-β-glucoside. X-axis represents the concentration of the proteins used in μg. Y-axis represents the quantities of peptidoglycan formed.

FIG. 7

Hydropathicity profile of E.coli PBP 1B. The figure represents the expanded hydropathicity profile of the N-terminal 150 amino acids of E.coli PBP 1B.

FIG. 8

Schematic representation of the cloning of the soluble transglycosylase domain of E.coli PBP 1B.

— vector sequences

═ sequences encoding ponB gene fragments and β-lactamase

The NcoI-NruI fragment encoding the N-terminal 64 amino acids of PBP 1B was cloned into the NcoI-EcoRV sites of pARC0534 to obtain the plasmid pARC0551. This recombinant plasmid harbours the gene encoding amino acid 1 to 480 of PBP 1B with internal deletion of amino acid 65 to 87.

FIG. 9

Schematic representation of pARC0559 encoding soluble PBP 1B.
— vector sequences
= sequences of the mutant ponB gene encoding the soluble form of PBP 1B (solPBP 1B), lactose repressor (lac $I_q$), kanamycin resistance ($Km^r$) and the origin of replication (ori).

Arrows represent direction of transcription of the genes.

FIG. 10

Purification of soluble PBP 1B. Panel A: SDS-PAGE, Coomassie blue staining of the different fractions. Panel B: [$^{125}$I]ampicillin binding profile of the same fractions. Lanes (1) and (2): Cytosolic fraction of E.coli BL 26(DE3)/pARC0559 induced cells; (3): Breakthrough fraction of Ampicillin-Affigel column; (4): Molecular weight markers; (5) and (6): Eluted fraction from the Ampicillin-Affigel column.

FIG. 11

Hydropathicity profile of S.pneumoniae PBP 1A. The figure shows the expanded profile of the hydropathicity profile of the N-terminal 100 amino acids of S.pneumoniae PBP 1A.

FIG. 12

Schematic representation of the plasmid pARC0512 encoding soluble form of S.pneumoniae PBP 1A.
— represents vector sequences
= represents sequences of the gene encoding soluble PBP 1A of S.pneumoniae (sPBP 1A), kanamycin resistance $Km^r$ and the origin of replication (ori).

FIG. 13

Penicillin binding profile of soluble S.pneumoniae PBP 1A. Host: E.coli BL 21(DE3)/pARC0512. Panel A: Coomassie Blue staining. Panel B: In vivo labelling with [$^3$H] benzyl penicillin followed by SDS-PAGE. Lanes (1) and (2): Cytosolic fraction of cells induced at 22° C. for 2 h and 20 h respectively; (3): Cytosolic fraction of cells induced at 30° C. for 2 h; (4): Cytosolic fraction of cells induced at 37° C. for 2h; (5): Molecular weight markers.

FIG. 14

Amino acid alignment of conserved regions of the transglycosylase domain of high molecular weight penicillin binding proteins. The figure compares the conserved residues of the Regions 1, 2 and 3 among E.1A (E.coli PBP 1A), E.1B (E.coli PBP 1B), S.1A (S.pneumoniae PBP 1A), and H.inf (Haemophilus influenzae PBP 1A). (*) indicates identical amino acid residues.

FIG. 15

Analysis of membrane protein of E.coli cells harbouring plasmids with genes encoding mutant PBP 1B. Panel A: [$^3$H]benzyl penicillin binding profile. Panel B: Western blotting with anti-PBP 1B sera. Lanes (1): Molecular weight markers; (2): Membrane fraction of E.coli JM 101/pBS96 cells; (3): Membrane fraction of E.coli 900521 ponB:Spc$^r$ cells (This host lacks chromosomal encoded PBP 1B); (4): Membrane fraction of E.coli 900521 ponB:spc./pARC0438 cells; (5): Membrane fraction of E.coli 900521 ponB:spc/pARC0469; (6): Membrane fraction of E.coli 900521 ponB:spc/pARC0468.

FIG. 16

Schematic representation of plasmid pARC0462 encoding wild type PBP 1B:
— vector sequences
= sequences of the ponB gene, replication origin (ori), chloramphenicol acetyl transferase ($cm^r$) and portions of the lac Z multiple cloning site.

FIG. 17

Schematic representation of plasmid pARC0463 encoding mutant ponB gene.
— vector sequences
= sequences of mutant the ponB gene encoding PBP 1Bdel8 amino acids, replication origin (ori), chloramphenicol acetyl transferase ($cm^r$) and portions of the lac Z multiple cloning site.

FIG. 18

Schematic representation of plasmid pARC0470 encoding mutant ponB gene.
— vector sequences
= sequences of mutant the ponB gene encoding PBP 1B $Q_{271-272}$-$A_{271-272}$, replication origin (ori), chloramphenicol acetyl transferase ($cm^r$) and portions of the lac Z multiple cloning site.

FIG. 19

Schematic representation of pARC0571 harbouring mutant ponA gene.
— vector sequences
= sequences of mutant ponA gene (PBP 1A QQ-AA), kanamycin resistance $Km^r$ origin of replication (ori).

FIG. 20

[$^{125}$I]Penicillin binding protein profile of wild type and mutant E.coli PBP 1A. Lane (1): E.coli AMA 1004 ponB:spc$^r$/pBS 98 (w.t. ponA); (2): E.coli BL21 (DE3) ponB:spc$^r$/pARC0570 (wt. ponA); (3): E.coli AMA 1004 del ponA/pBS 98 ponA/pARC0571 (QQ-AA ponA); (4): E.coli AMA 1004 del ponA/pBS 98 (w.t. ponA); (5): Molecular weight markers.

FIG. 21

Schematic representation of plasmid pARC0592.
— vector sequences
= sequences of truncated ponB gene encoding for the N-terminal 553 amino acids of PBP 1B (hinge 1B), kanamycin resistance ($Km^r$) and origin of replication (ori)

FIG. 22

Schematic representation of plasmid pARC0593.
— vector sequences
= sequences of mutant truncated ponB gene encoding a soluble form of the truncated N-terminal 553 amino acids of PBP 1B (soluble hinge 1B), kanamycin resistance $Km^r$ and origin of replication (ori).

FIG. 23

Schematic representation of plasmid pARC0392.
— vector sequences
= sequences of mutant gene encoding truncated fragment of PBP 1B protein, representing amino acids 210–368 sequences fused in frame at its 3'-end to sequences encoding a enterokinase site followed by a stretch of 6 histidines, kanamycin resistance $Km^r$ and origin of replication (ori).

FIG. 24

Schematic representation of plasmid pARC0499.
— vector sequences
= sequences of mutant ponAdel23 gene fused at its 5'-end in frame to sequences encoding Glutathione-S-transferase encoding sequences, β-lactamase $amp^r$ and origin of replication (ori).

FIG. 25

Schematic representation of plasmid pARC0400.
— vector sequences
= sequences of mutant ponAdel23 sequences fused in frame at its 3'-end to sequences encoding a enterokinase site followed by a stretch of 6 histidines, kanamycin resistance $Km^r$ and origin of replication (ori).

References

Balganesh, T. S. And Lacks, S. (1984): Gene 29, 221–230 den Blaauwen, T. et al. (1990): J. Bact. 172, 63–70

Broome-Smith, J. K. et al. (1985): Eur. J. Biochem. 147, 437–446

Covarrubias, L. & Bolivar, F. (1982): Gene 17, 79–89

Edelman, A. et al. (1987): Molecular Microbiology 1, 101–106

Fu Wang, R. and Kushner, S. R. (1991): Gene 100, 195–199

Hackenbeck et al. (eds.) The target of penicillin. W. de Gruyter publications, Berlin/New York 1983.

Hamilton, C. A. et al. (1989): J. Bacteriol. 171, 4617–4622

Heijenoort, Y. van, et al. (1978): FEBS Letters 89, 141–144

Heijenoort, Y. van, et al. (1992): J. Bacteriol. 174, 3549–3557

Ishino, F. et al. (1980): Biochem. Biophys. Res. Comm. 97, 287–293

Kunkel, T. A. (1985): Proc. Natl. Acad. Sci. U.S.A. 82, 488–492

Kyte and Doolittle (1982): J. Mol. Biol. 157, 105–132

Lacks, S. A. (1968): Genetics 60, 685–706

Martin, C. et al. (1992): J. Bacteriol. 174, 4517–4523

Miller, J. H. (ed.) (1972): Experiments in Molecular Genetics. Cold Spring Harbor Publications.

Nakagawa, J. S. et al. (1984): J. Biol. Chem. 259, 13937–13946

Page, W. J. et al. (1982): J. Bacteriol. 151, 237–242

Rojo et. al. (1984): J. Antibiotics. 37, 389–393

Sambrook, J., Fritsch, E. F. and Maniatis, T. (1989): Molecular Cloning: A laboratory manual, 2nd Ed., Cold Spring Harbor Laboratory, Cold Spring Harbor, N.Y.

Sanger, et al. (1977): Proc. Natl. Acad. Sci. U.S.A. 74, 5463–5467

Spratt, B. S. (1977): Eur. J. Biochem. 72, 341–352

Studier, F. W. et al. (1990): Methods in Enzymology 185, 61–89

Tomb, F. et al. (1991): Gene 104, 1–10

Yousif, S. Y. et al. (1985): J. Gen. Microbiol. 131, 2839–2845

---

SEQUENCE LISTING

```
(1) GENERAL INFORMATION:

(iii) NUMBER OF SEQUENCES: 42

(2) INFORMATION FOR SEQ ID NO:1:

(i) SEQUENCE CHARACTERISTICS:
        (A) LENGTH: 2487 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: DH5 alpha (vii) IMMEDIATE SOURCE:
        (A) LIBRARY: PCR cloning
        (B) CLONE: pARC 0558 Soluble PBP 1A del 23

(ix) FEATURE:
        (A) NAME/KEY: CDS
        (B) LOCATION: 1..2487

(ix) FEATURE:
        (A) NAME/KEY: mat_peptide
        (B) LOCATION: 1..2484

(xi) SEQUENCE DESCRIPTION: SEQ ID NO:1:

ATG GGC CTA TAC CGC TAC ATC GAG CCA CAA CTG CCG GAT GTG GCG ACA       48
Met Gly Leu Tyr Arg Tyr Ile Glu Pro Gln Leu Pro Asp Val Ala Thr
 1               5                  10                  15

TTA AAA GAT GTT CGC CTG CAA ATT CCG ATG CAG ATT TAC AGC GCC GAT       96
Leu Lys Asp Val Arg Leu Gln Ile Pro Met Gln Ile Tyr Ser Ala Asp
             20                  25                  30

GGC GAG CTG ATT GCT CAA TAC GGT GAG AAA CGT CGT ATT CCG GTT ACG      144
Gly Glu Leu Ile Ala Gln Tyr Gly Glu Lys Arg Arg Ile Pro Val Thr
         35                  40                  45
```

| | | |
|---|---|---|
| TTG GAT CAA ATC CCA CCG GAG ATG GTG AAA GCC TTT ATC GCG ACA GAA<br>Leu Asp Gln Ile Pro Pro Glu Met Val Lys Ala Phe Ile Ala Thr Glu<br>50                  55                  60 | 192 |
| GAC AGC CGC TTC TAC GAG CAT CAC GGC GTT GAC CCG GTG GGG ATC TTC<br>Asp Ser Arg Phe Tyr Glu His His Gly Val Asp Pro Val Gly Ile Phe<br>65                  70                  75                  80 | 240 |
| CGT GCA GCA AGC GTG GCG CTG TTC TCC GGT CAC GCG TCA CAA GGG GCA<br>Arg Ala Ala Ser Val Ala Leu Phe Ser Gly His Ala Ser Gln Gly Ala<br>85                  90                  95 | 288 |
| AGT ACC ATT ACC CAG CAG CTG GCG AGA AAC TTC TTC CTC AGT CCA GAA<br>Ser Thr Ile Thr Gln Gln Leu Ala Arg Asn Phe Phe Leu Ser Pro Glu<br>100                105              110 | 336 |
| CGC ACG CTG ATG CGT AAG ATT AAG GAA GTC TTC CTC GCG ATT CGC ATT<br>Arg Thr Leu Met Arg Lys Ile Lys Glu Val Phe Leu Ala Ile Arg Ile<br>115                120              125 | 384 |
| GAA CAG CTG CTG ACG AAA GAC GAG ATC CTC GAG CTT TAT CTG AAC AAG<br>Glu Gln Leu Leu Thr Lys Asp Glu Ile Leu Glu Leu Tyr Leu Asn Lys<br>130                135              140 | 432 |
| ATT TAC CTT GGT TAC CGC GCC TAT GGT GTC GGT GCT GCG GCA CAA GTC<br>Ile Tyr Leu Gly Tyr Arg Ala Tyr Gly Val Gly Ala Ala Ala Gln Val<br>145                150              155              160 | 480 |
| TAT TTC GGA AAA ACG GTC GAC CAA CTG ACG CTG AAC GAA ATG GCG GTG<br>Tyr Phe Gly Lys Thr Val Asp Gln Leu Thr Leu Asn Glu Met Ala Val<br>165                170              175 | 528 |
| ATA GCC GGG CTG CCG AAA GCG CCT TCC ACC TTC AAC CCG CTC TAC TCG<br>Ile Ala Gly Leu Pro Lys Ala Pro Ser Thr Phe Asn Pro Leu Tyr Ser<br>180                185              190 | 576 |
| ATG GAT CGT GCC GTC GCG CGG CGT AAC GTC GTG CTG TCG CGG ATG CTG<br>Met Asp Arg Ala Val Ala Arg Arg Asn Val Val Leu Ser Arg Met Leu<br>195                200              205 | 624 |
| GAT GAA GGG TAT ATC ACC CAA CAA CAG TTC GAT CAG ACA CGC ACT GAG<br>Asp Glu Gly Tyr Ile Thr Gln Gln Gln Phe Asp Gln Thr Arg Thr Glu<br>210                215              220 | 672 |
| GCG ATT AAC GCT AAC TAT CAC GCG CCG GAG ATT GCT TTC TCT GCG CCG<br>Ala Ile Asn Ala Asn Tyr His Ala Pro Glu Ile Ala Phe Ser Ala Pro<br>225                230              235              240 | 720 |
| TAC CTG AGC GAA ATG GTG CGC CAG GAG ATG TAT AAC CGT TAT GGC GAA<br>Tyr Leu Ser Glu Met Val Arg Gln Glu Met Tyr Asn Arg Tyr Gly Glu<br>245                250              255 | 768 |
| AGT GCC TAT GAA GAC GGT TAT CGC ATT TAC ACC ACC ATC ACC CGC AAA<br>Ser Ala Tyr Glu Asp Gly Tyr Arg Ile Tyr Thr Thr Ile Thr Arg Lys<br>260                265              270 | 816 |
| GTG CAG CAG GCC GCG CAG CAG GCG GTA CGT AAT AAC GTG CTG GAC TAC<br>Val Gln Gln Ala Ala Gln Gln Ala Val Arg Asn Asn Val Leu Asp Tyr<br>275                280              285 | 864 |
| GAC ATG CGC CAC GGC TAT CGC GGC CCG GCA AAT GTG CTG TGG AAA GTG<br>Asp Met Arg His Gly Tyr Arg Gly Pro Ala Asn Val Leu Trp Lys Val<br>290                295              300 | 912 |
| GGC GAG TCG GCG TGG GAT AAC AAC AAG ATT ACC GAT ACG CTG AAG GCG<br>Gly Glu Ser Ala Trp Asp Asn Asn Lys Ile Thr Asp Thr Leu Lys Ala<br>305                310              315              320 | 960 |
| CTG CCA ACC TAT GGT CCG CTG CTG CCT GCC GCA GTC ACC AGC GCC AAT<br>Leu Pro Thr Tyr Gly Pro Leu Leu Pro Ala Ala Val Thr Ser Ala Asn<br>325                330              335 | 1008 |
| CCT CAG CAA GCG ACG GCG ATG CTG GCG GAC GGG TCG ACC GTC GCA TTG<br>Pro Gln Gln Ala Thr Ala Met Leu Ala Asp Gly Ser Thr Val Ala Leu<br>340                345              350 | 1056 |
| AGT ATG GAA GGC GTT CGC TGG GCG CGT CCT TAC CGT TCG GAT ACT CAG<br>Ser Met Glu Gly Val Arg Trp Ala Arg Pro Tyr Arg Ser Asp Thr Gln<br>355                360              365 | 1104 |

-continued

| | |
|---|---|
| CAA GGA CCG ACG CCG CGT AAA GTG ACC GAT GTT CTG CAA ACG GGT CAG<br>Gln Gly Pro Thr Pro Arg Lys Val Thr Asp Val Leu Gln Thr Gly Gln<br>370                              375                          380 | 1152 |
| CAA ATC TGG GTT CGT CAG GTT GGC GAT GCA TGG TGG CTG GCA CAA GTG<br>Gln Ile Trp Val Arg Gln Val Gly Asp Ala Trp Trp Leu Ala Gln Val<br>385                              390                          395                          400 | 1200 |
| CCG GAA GTG AAC TCG GCG CTG GTG TCG ATC AAT CCG CAA AAC GGT GCC<br>Pro Glu Val Asn Ser Ala Leu Val Ser Ile Asn Pro Gln Asn Gly Ala<br>                          405                          410                          415 | 1248 |
| GTT ATG GCG CTG GTC GGT GGC TTT GAT TTC AAT CAG AGC AAG TTT AAC<br>Val Met Ala Leu Val Gly Gly Phe Asp Phe Asn Gln Ser Lys Phe Asn<br>            420                          425                          430 | 1296 |
| CGC GCC ACC CAG GCA CTG CGT CAG GTG GGT TCC AAC ATC AAA CCG TTC<br>Arg Ala Thr Gln Ala Leu Arg Gln Val Gly Ser Asn Ile Lys Pro Phe<br>            435                          440                          445 | 1344 |
| CTC TAC ACC GCG GCG ATG GAT AAA GGT CTG ACG CTG GCA AGT ATG TTG<br>Leu Tyr Thr Ala Ala Met Asp Lys Gly Leu Thr Leu Ala Ser Met Leu<br>450                              455                          460 | 1392 |
| AAC GAT GTG CCA ATT TCT CGC TGG GAT GCA AGT GCC GGT TCT GAC TGG<br>Asn Asp Val Pro Ile Ser Arg Trp Asp Ala Ser Ala Gly Ser Asp Trp<br>465                              470                          475                          480 | 1440 |
| CAG CCG AAG AAC TCA CCA CCG CAG TAT GCT GGT CCA ATT CGC TTA CGT<br>Gln Pro Lys Asn Ser Pro Pro Gln Tyr Ala Gly Pro Ile Arg Leu Arg<br>                          485                          490                          495 | 1488 |
| CAG GGG CTG GGT CAG TCG AAA AAC GTG GTG ATG GTA CGC GCA ATG CGG<br>Gln Gly Leu Gly Gln Ser Lys Asn Val Val Met Val Arg Ala Met Arg<br>            500                          505                          510 | 1536 |
| GCG ATG GGC GTC GAC TAC GCT GCA GAA TAT CTG CAA CGC TTC GGC TTC<br>Ala Met Gly Val Asp Tyr Ala Ala Glu Tyr Leu Gln Arg Phe Gly Phe<br>            515                          520                          525 | 1584 |
| CCG GCA CAA AAC ATT GTC CAC ACC GAA TCG CTG GCG CTG GGT TCA GCG<br>Pro Ala Gln Asn Ile Val His Thr Glu Ser Leu Ala Leu Gly Ser Ala<br>530                              535                          540 | 1632 |
| TCC TTC ACC CCA ATG CAG GTG GCG CGC GGC TAC GCG GTC ATG GCG AAC<br>Ser Phe Thr Pro Met Gln Val Ala Arg Gly Tyr Ala Val Met Ala Asn<br>545                              550                          555                          560 | 1680 |
| GGC GGC TTC CTG GTG GAC CCG TGG TTT ATC AGC AAA ATT GAA AAC GAT<br>Gly Gly Phe Leu Val Asp Pro Trp Phe Ile Ser Lys Ile Glu Asn Asp<br>                          565                          570                          575 | 1728 |
| CAG GGC GGC GTG ATT TTC GAA GCG AAA CCG AAA GTA GCC TGC CCG GAA<br>Gln Gly Gly Val Ile Phe Glu Ala Lys Pro Lys Val Ala Cys Pro Glu<br>            580                          585                          590 | 1776 |
| TGC GAT ATT CCG GTG ATT TAC GGT GAT ACG CAG AAA TCG AAC GTG CTG<br>Cys Asp Ile Pro Val Ile Tyr Gly Asp Thr Gln Lys Ser Asn Val Leu<br>            595                          600                          605 | 1824 |
| GAA AAT AAC GAT GTT GAA GAT GTC GCT ATC TCC CGC GAG CAG CAG AAT<br>Glu Asn Asn Asp Val Glu Asp Val Ala Ile Ser Arg Glu Gln Gln Asn<br>610                              615                          620 | 1872 |
| GTT TCT GTA CCA ATG CCG CAG CTG GAG CAG GCA AAT CAG GCG TTA GTG<br>Val Ser Val Pro Met Pro Gln Leu Glu Gln Ala Asn Gln Ala Leu Val<br>625                              630                          635                          640 | 1920 |
| GCG AAG ACT GGC GCG CAG GAG TAC GCA CCG CAC GTC ATC AAC ACT CCG<br>Ala Lys Thr Gly Ala Gln Glu Tyr Ala Pro His Val Ile Asn Thr Pro<br>                          645                          650                          655 | 1968 |
| CTG GCA TTC CTG ATT AAG AGT GCT TTG AAC ACC AAT ATC TTT GGT GAG<br>Leu Ala Phe Leu Ile Lys Ser Ala Leu Asn Thr Asn Ile Phe Gly Glu<br>660                              665                          670 | 2016 |
| CCA GGC TGG CAG GGT ACT GGC TGG CGT GCA GGT CGT GAT TTG CAG CGT<br>Pro Gly Trp Gln Gly Thr Gly Trp Arg Ala Gly Arg Asp Leu Gln Arg<br>            675                          680                          685 | 2064 |

```
CGC GAT ATC GGC GGG AAA ACC GGG ACC ACT AAC AGT TCG AAA GAT GCG    2112
Arg Asp Ile Gly Gly Lys Thr Gly Thr Thr Asn Ser Ser Lys Asp Ala
        690                 695                 700

TGG TTC TCG GGT TAC GGT CCG GGC GTT GTG ACC TCG GTC TGG ATT GGC    2160
Trp Phe Ser Gly Tyr Gly Pro Gly Val Val Thr Ser Val Trp Ile Gly
705                 710                 715                 720

TTT GAT GAT CAC CGT CGT AAT CTC GGT CAT ACA ACG GCT TCC GGA GCG    2208
Phe Asp Asp His Arg Arg Asn Leu Gly His Thr Thr Ala Ser Gly Ala
                725                 730                 735

ATT AAA GAT CAG ATC TCA GGT TAC GAA GGC GGT GCC AAG AGT GCC CAG    2256
Ile Lys Asp Gln Ile Ser Gly Tyr Glu Gly Gly Ala Lys Ser Ala Gln
            740                 745                 750

CCT GCA TGG GAC GCT TAT ATG AAA GCC GTT CTT GAA GGT GTG CCG GAG    2304
Pro Ala Trp Asp Ala Tyr Met Lys Ala Val Leu Glu Gly Val Pro Glu
        755                 760                 765

CAG CCG CTG ACG CCG CCA CCG GGT ATT GTG ACG GTG AAT ATC GAT CGC    2352
Gln Pro Leu Thr Pro Pro Pro Gly Ile Val Thr Val Asn Ile Asp Arg
    770                 775                 780

AGC ACC GGG CAG TTA GCT AAT GGT GGC AAC AGC CGC GAA GAG TAT TTC    2400
Ser Thr Gly Gln Leu Ala Asn Gly Gly Asn Ser Arg Glu Glu Tyr Phe
785                 790                 795                 800

ATC GAA GGT ACG CAG CCG ACA CAA CAG GCA GTG CAC GAG GTG GGA ACG    2448
Ile Glu Gly Thr Gln Pro Thr Gln Gln Ala Val His Glu Val Gly Thr
                805                 810                 815

ACC ATT ATC GAT AAT GGC GAG GCA CAG GAA TTG TTG TGA                2487
Thr Ile Ile Asp Asn Gly Glu Ala Gln Glu Leu Leu  *
            820                 825
```

(2) INFORMATION FOR SEQ ID NO:2:

(i) SEQUENCE CHARACTERISTICS:
        (A) LENGTH: 828 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Leu Tyr Arg Tyr Ile Glu Pro Gln Leu Pro Asp Val Ala Thr
1               5                   10                  15

Leu Lys Asp Val Arg Leu Gln Ile Pro Met Gln Ile Tyr Ser Ala Asp
                20                  25                  30

Gly Glu Leu Ile Ala Gln Tyr Gly Glu Lys Arg Arg Ile Pro Val Thr
            35                  40                  45

Leu Asp Gln Ile Pro Pro Glu Met Val Lys Ala Phe Ile Ala Thr Glu
        50                  55                  60

Asp Ser Arg Phe Tyr Glu His His Gly Val Asp Pro Val Gly Ile Phe
65                  70                  75                  80

Arg Ala Ala Ser Val Ala Leu Phe Ser Gly His Ala Ser Gln Gly Ala
                85                  90                  95

Ser Thr Ile Thr Gln Gln Leu Ala Arg Asn Phe Phe Leu Ser Pro Glu
            100                 105                 110

Arg Thr Leu Met Arg Lys Ile Lys Glu Val Phe Leu Ala Ile Arg Ile
        115                 120                 125

Glu Gln Leu Leu Thr Lys Asp Glu Ile Leu Glu Leu Tyr Leu Asn Lys
    130                 135                 140

Ile Tyr Leu Gly Tyr Arg Ala Tyr Gly Val Gly Ala Ala Ala Gln Val
145                 150                 155                 160

Tyr Phe Gly Lys Thr Val Asp Gln Leu Thr Leu Asn Glu Met Ala Val
                165                 170                 175
```

-continued

```
Ile Ala Gly Leu Pro Lys Ala Pro Ser Thr Phe Asn Pro Leu Tyr Ser
            180                 185                 190

Met Asp Arg Ala Val Ala Arg Arg Asn Val Val Leu Ser Arg Met Leu
        195                 200                 205

Asp Glu Gly Tyr Ile Thr Gln Gln Phe Asp Gln Thr Arg Thr Glu
    210                 215                 220

Ala Ile Asn Ala Asn Tyr His Ala Pro Glu Ile Ala Phe Ser Ala Pro
225                 230                 235                 240

Tyr Leu Ser Glu Met Val Arg Gln Glu Met Tyr Asn Arg Tyr Gly Glu
                245                 250                 255

Ser Ala Tyr Glu Asp Gly Tyr Arg Ile Tyr Thr Thr Ile Thr Arg Lys
            260                 265                 270

Val Gln Gln Ala Ala Gln Gln Ala Val Arg Asn Asn Val Leu Asp Tyr
        275                 280                 285

Asp Met Arg His Gly Tyr Arg Gly Pro Ala Asn Val Leu Trp Lys Val
    290                 295                 300

Gly Glu Ser Ala Trp Asp Asn Asn Lys Ile Thr Asp Thr Leu Lys Ala
305                 310                 315                 320

Leu Pro Thr Tyr Gly Pro Leu Pro Ala Ala Val Thr Ser Ala Asn
                325                 330                 335

Pro Gln Gln Ala Thr Ala Met Leu Ala Asp Gly Ser Thr Val Ala Leu
            340                 345                 350

Ser Met Glu Gly Val Arg Trp Ala Arg Pro Tyr Arg Ser Asp Thr Gln
        355                 360                 365

Gln Gly Pro Thr Pro Arg Lys Val Thr Asp Val Leu Gln Thr Gly Gln
    370                 375                 380

Gln Ile Trp Val Arg Gln Val Gly Asp Ala Trp Trp Leu Ala Gln Val
385                 390                 395                 400

Pro Glu Val Asn Ser Ala Leu Val Ser Ile Asn Pro Gln Asn Gly Ala
                405                 410                 415

Val Met Ala Leu Val Gly Gly Phe Asp Phe Asn Gln Ser Lys Phe Asn
            420                 425                 430

Arg Ala Thr Gln Ala Leu Arg Gln Val Gly Ser Asn Ile Lys Pro Phe
        435                 440                 445

Leu Tyr Thr Ala Ala Met Asp Lys Gly Leu Thr Leu Ala Ser Met Leu
    450                 455                 460

Asn Asp Val Pro Ile Ser Arg Trp Asp Ala Ser Ala Gly Ser Asp Trp
465                 470                 475                 480

Gln Pro Lys Asn Ser Pro Gln Tyr Ala Gly Pro Ile Arg Leu Arg
                485                 490                 495

Gln Gly Leu Gly Gln Ser Lys Asn Val Val Met Val Arg Ala Met Arg
            500                 505                 510

Ala Met Gly Val Asp Tyr Ala Ala Glu Tyr Leu Gln Arg Phe Gly Phe
        515                 520                 525

Pro Ala Gln Asn Ile Val His Thr Glu Ser Leu Ala Leu Gly Ser Ala
    530                 535                 540

Ser Phe Thr Pro Met Gln Val Ala Arg Gly Tyr Ala Val Met Ala Asn
545                 550                 555                 560

Gly Gly Phe Leu Val Asp Pro Trp Phe Ile Ser Lys Ile Glu Asn Asp
                565                 570                 575

Gln Gly Gly Val Ile Phe Glu Ala Lys Pro Lys Val Ala Cys Pro Glu
            580                 585                 590

Cys Asp Ile Pro Val Ile Tyr Gly Asp Thr Gln Lys Ser Asn Val Leu
```

```
                    595                 600                 605
Glu Asn Asn Asp Val Glu Asp Val Ala Ile Ser Arg Glu Gln Gln Asn
            610                 615                 620

Val Ser Val Pro Met Pro Gln Leu Glu Gln Ala Asn Gln Ala Leu Val
625                 630                 635                 640

Ala Lys Thr Gly Ala Gln Glu Tyr Ala Pro His Val Ile Asn Thr Pro
            645                 650                 655

Leu Ala Phe Leu Ile Lys Ser Ala Leu Asn Thr Asn Ile Phe Gly Glu
            660                 665                 670

Pro Gly Trp Gln Gly Thr Gly Trp Arg Ala Gly Arg Asp Leu Gln Arg
            675                 680                 685

Arg Asp Ile Gly Gly Lys Thr Gly Thr Thr Asn Ser Ser Lys Asp Ala
690                 695                 700

Trp Phe Ser Gly Tyr Gly Pro Gly Val Val Thr Ser Val Trp Ile Gly
705                 710                 715                 720

Phe Asp Asp His Arg Arg Asn Leu Gly His Thr Thr Ala Ser Gly Ala
                725                 730                 735

Ile Lys Asp Gln Ile Ser Gly Tyr Glu Gly Gly Ala Lys Ser Ala Gln
            740                 745                 750

Pro Ala Trp Asp Ala Tyr Met Lys Ala Val Leu Glu Gly Val Pro Glu
            755                 760                 765

Gln Pro Leu Thr Pro Pro Gly Ile Val Thr Val Asn Ile Asp Arg
            770                 775                 780

Ser Thr Gly Gln Leu Ala Asn Gly Gly Asn Ser Arg Glu Glu Tyr Phe
785                 790                 795                 800

Ile Glu Gly Thr Gln Pro Thr Gln Gln Ala Val His Glu Val Gly Thr
            805                 810                 815

Thr Ile Ile Asp Asn Gly Glu Ala Gln Glu Leu Leu
            820                 825

(2) INFORMATION FOR SEQ ID NO:3:

(i) SEQUENCE CHARACTERISTICS:
        (A) LENGTH: 2472 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Escherichia coli
        (B) STRAIN: DH5 alpha (vii) IMMEDIATE SOURCE:
        (A) LIBRARY: PCR cloning
        (B) CLONE: pARC 0556 Soluble PBP 1B (ix) FEATURE:
        (A) NAME/KEY: CDS
        (B) LOCATION: 1..2472

(ix) FEATURE:
        (A) NAME/KEY: mat_peptide
        (B) LOCATION: 1..2469

(xi) SEQUENCE DESCRIPTION: SEQ ID NO:3:

ATG GCC GGG AAT GAC CGC GAG CCA ATT GGA CGC AAA GGG AAA CCG ACG      48
Met Ala Gly Asn Asp Arg Glu Pro Ile Gly Arg Lys Gly Lys Pro Thr
1               5                   10                  15

CGT CCG GTC AAA CAA AAG GTA AGC CGT CGT CGT TAC GAA GAT GAC GAT      96
Arg Pro Val Lys Gln Lys Val Ser Arg Arg Arg Tyr Glu Asp Asp Asp
            20                  25                  30
```

| | | |
|---|---|---|
| GAT TAC GAC GAT TAT GAT GAC TAT GAG GAT GAA GAA CCG ATG CCG CGC<br>Asp Tyr Asp Asp Tyr Asp Asp Tyr Glu Asp Glu Glu Pro Met Pro Arg<br>          35                       40                       45 | | 144 |
| AAA GGT AAG GGC AAA GGC AAA GGG CGT AAG CCT CGT GGC AAA CGC GGC<br>Lys Gly Lys Gly Lys Gly Lys Gly Arg Lys Pro Arg Gly Lys Arg Gly<br>          50                       55                       60 | | 192 |
| TCG ATC GAT CAA AAA ATT CGT AGC CGT ATT GAT GGC AAG GTC TGG CAA<br>Ser Ile Asp Gln Lys Ile Arg Ser Arg Ile Asp Gly Lys Val Trp Gln<br>65                       70                       75                       80 | | 240 |
| CTC GCT GCG GCA GTT TAT GGC CGA ATG GTC AAT CTT GAG CCA GAC ATG<br>Leu Ala Ala Ala Val Tyr Gly Arg Met Val Asn Leu Glu Pro Asp Met<br>                       85                       90                       95 | | 288 |
| ACC ATC AGC AAG AAC GAG ATG GTG AAG CTG CTG GAG GCG ACC CAG TAT<br>Thr Ile Ser Lys Asn Glu Met Val Lys Leu Leu Glu Ala Thr Gln Tyr<br>          100                      105                      110 | | 336 |
| CGT CAG GTG TCG AAA ATG ACC CGT CCT GGC GAA TTT ACC GTG CAG GCC<br>Arg Gln Val Ser Lys Met Thr Arg Pro Gly Glu Phe Thr Val Gln Ala<br>               115                      120                     125 | | 384 |
| AAC AGC ATT GAG ATG ATT CGC CGT CCG TTT GAT TTC CCG GAC AGT AAA<br>Asn Ser Ile Glu Met Ile Arg Arg Pro Phe Asp Phe Pro Asp Ser Lys<br>          130                      135                      140 | | 432 |
| GAA GGA CAG GTG CGC GCG CGT CTG ACC TTT GAT GGC GAT CAT CTG GCG<br>Glu Gly Gln Val Arg Ala Arg Leu Thr Phe Asp Gly Asp His Leu Ala<br>145                      150                      155                     160 | | 480 |
| ACG ATC GTC AAT ATG GAG AAC AAC CGT CAG TTC GGT TTC TTC CGT CTT<br>Thr Ile Val Asn Met Glu Asn Asn Arg Gln Phe Gly Phe Phe Arg Leu<br>               165                      170                     175 | | 528 |
| GAT CCG CGT CTG ATC ACC ATG ATC TCT TCG CCA AAC GGT GAG CAG CGT<br>Asp Pro Arg Leu Ile Thr Met Ile Ser Ser Pro Asn Gly Glu Gln Arg<br>               180                      185                     190 | | 576 |
| CTG TTT GTG CCG CGC AGT GGT TTC CCG GAT TTG CTG GTG GAT ACT TTG<br>Leu Phe Val Pro Arg Ser Gly Phe Pro Asp Leu Leu Val Asp Thr Leu<br>          195                      200                     205 | | 624 |
| CTG GCG ACA GAA GAC CGT CAT TTT TAC GAG CAT GAT GGA ATC AGT CTC<br>Leu Ala Thr Glu Asp Arg His Phe Tyr Glu His Asp Gly Ile Ser Leu<br>          210                      215                     220 | | 672 |
| TAC TCA ATC GGA CGT GCG GTG CTG GCA AAC CTG ACC GCC GGA CGC ACG<br>Tyr Ser Ile Gly Arg Ala Val Leu Ala Asn Leu Thr Ala Gly Arg Thr<br>225                      230                      235                     240 | | 720 |
| GTA CAG GGT GCG AGT ACG CTG ACG CAA CAG CTG GTG AAA AAC CTG TTC<br>Val Gln Gly Ala Ser Thr Leu Thr Gln Gln Leu Val Lys Asn Leu Phe<br>               245                      250                     255 | | 768 |
| CTC TCC AGC GAG CGT TCT TAC TGG CGT AAA GCG AAC GAA GCT TAC ATG<br>Leu Ser Ser Glu Arg Ser Tyr Trp Arg Lys Ala Asn Glu Ala Tyr Met<br>          260                      265                     270 | | 816 |
| GCG CTG ATC ATG GAC GCG CGT TAC AGC AAA GAC CGT ATT CTT GAG CTG<br>Ala Leu Ile Met Asp Ala Arg Tyr Ser Lys Asp Arg Ile Leu Glu Leu<br>               275                      280                     285 | | 864 |
| TAT ATG AAC GAG GTG TAT CTC GGT CAG AGC GGC GAC AAC GAA ATC CGC<br>Tyr Met Asn Glu Val Tyr Leu Gly Gln Ser Gly Asp Asn Glu Ile Arg<br>          290                      295                     300 | | 912 |
| GGC TTC CCG CTG GCA AGC TTG TAT TAC TTT GGT CGC CCG GTA GAA GAG<br>Gly Phe Pro Leu Ala Ser Leu Tyr Tyr Phe Gly Arg Pro Val Glu Glu<br>305                      310                      315                     320 | | 960 |
| CTA AGC CTC GAC CAG CAG GCG CTG TTA GTC GGT ATG GTG AAA GGG GCG<br>Leu Ser Leu Asp Gln Gln Ala Leu Leu Val Gly Met Val Lys Gly Ala<br>               325                      330                     335 | | 1008 |
| TCC ATC TAC AAC CCG TGG CGT AAC CCA AAA CTG GCG CTG GAG CGA CGT<br>Ser Ile Tyr Asn Pro Trp Arg Asn Pro Lys Leu Ala Leu Glu Arg Arg<br>          340                      345                     350 | | 1056 |

```
AAT CTG GTG CTG CGT CTG CTG CAA CAG CAA CAG ATT ATT GAT CAA GAA      1104
Asn Leu Val Leu Arg Leu Leu Gln Gln Gln Gln Ile Ile Asp Gln Glu
        355                 360                 365

CTC TAT GAC ATG TTG AGT GCC CGT CCG CTG GGG GTT CAG CCG CGC GGT      1152
Leu Tyr Asp Met Leu Ser Ala Arg Pro Leu Gly Val Gln Pro Arg Gly
370                 375                 380

GGG GTG ATC TCT CCT CAG CCA GCC TTT ATG CAA CTG GTG CGT CAG GAG      1200
Gly Val Ile Ser Pro Gln Pro Ala Phe Met Gln Leu Val Arg Gln Glu
385                 390                 395                 400

CTG CAG GCA AAA CTG GGC GAT AAG GTA AAA GAT CTC TCC GGC GTG AAG      1248
Leu Gln Ala Lys Leu Gly Asp Lys Val Lys Asp Leu Ser Gly Val Lys
                405                 410                 415

ATC TTC ACT ACC TTT GAC TCG GTG GCC CAG GAC GCG GCA GAA AAA GCC      1296
Ile Phe Thr Thr Phe Asp Ser Val Ala Gln Asp Ala Ala Glu Lys Ala
                420                 425                 430

GCC GTG GAA GGC ATT CCG GCA CTG AAG AAA CAG CGT AAG TTG AGC GAT      1344
Ala Val Glu Gly Ile Pro Ala Leu Lys Lys Gln Arg Lys Leu Ser Asp
        435                 440                 445

CTT GAA ACT GCG ATT GTG GTC GTC GAC CGC TTT AGT GGT GAA GTT CGT      1392
Leu Glu Thr Ala Ile Val Val Val Asp Arg Phe Ser Gly Glu Val Arg
450                 455                 460

GCG ATG GTC GGA GGT TCT GAG CCG CAG TTT GCG GGC TAC AAC CGT GCG      1440
Ala Met Val Gly Gly Ser Glu Pro Gln Phe Ala Gly Tyr Asn Arg Ala
465                 470                 475                 480

ATG CAG GCG CGT CGT TCG ATT GGT TCC CTT GCA AAA CCA GCG ACT TAT      1488
Met Gln Ala Arg Arg Ser Ile Gly Ser Leu Ala Lys Pro Ala Thr Tyr
                485                 490                 495

CTG ACG GCC TTA AGC CAG CCG AAA ATC TAT CGT CTG AAT ACG TGG ATT      1536
Leu Thr Ala Leu Ser Gln Pro Lys Ile Tyr Arg Leu Asn Thr Trp Ile
                500                 505                 510

GCG GAT GCG CCA ATT GCG CTG CGT CAG CCG AAT GGC CAG GTC TGG TCA      1584
Ala Asp Ala Pro Ile Ala Leu Arg Gln Pro Asn Gly Gln Val Trp Ser
        515                 520                 525

CCG CAG AAT GAT GAC CGT CGT TAT AGC GAA AGC GGC AGA GTG ATG CTG      1632
Pro Gln Asn Asp Asp Arg Arg Tyr Ser Glu Ser Gly Arg Val Met Leu
530                 535                 540

GTG GAT GCG TTG ACC CGT TCG ATG AAC GTG CCG ACG GTA AAT CTG GGG      1680
Val Asp Ala Leu Thr Arg Ser Met Asn Val Pro Thr Val Asn Leu Gly
545                 550                 555                 560

ATG GCG CTG GGG CTG CCT GCG GTT ACG GAG ACC TGG ATT AAA CTG GGC      1728
Met Ala Leu Gly Leu Pro Ala Val Thr Glu Thr Trp Ile Lys Leu Gly
                565                 570                 575

GTA CCG AAA GAT CAG TTG CAT CCG GTT CCG GCA ATG CTG CTG GGG GCG      1776
Val Pro Lys Asp Gln Leu His Pro Val Pro Ala Met Leu Leu Gly Ala
                580                 585                 590

TTG AAC TTA ACG CCA ATC GAA GTG GCG CAG GCA TTC CAG ACC ATC GCC      1824
Leu Asn Leu Thr Pro Ile Glu Val Ala Gln Ala Phe Gln Thr Ile Ala
        595                 600                 605

AGC GGT GGT AAC CGT GCA CCG CTT TCT GCG CTG CGT TCG GTA ATC GCG      1872
Ser Gly Gly Asn Arg Ala Pro Leu Ser Ala Leu Arg Ser Val Ile Ala
610                 615                 620

GAA GAT GGC AAA GTG CTG TAT CAG AGC TTC CCG CAG GCG GAA CGC GCT      1920
Glu Asp Gly Lys Val Leu Tyr Gln Ser Phe Pro Gln Ala Glu Arg Ala
625                 630                 635                 640

GTT CCG GCG CAG GCG GCG TAT CTG ACA CTA TGG ACC ATG CAG CAG GTG      1968
Val Pro Ala Gln Ala Ala Tyr Leu Thr Leu Trp Thr Met Gln Gln Val
                645                 650                 655

GTA CAA CGC GGT ACG GGT CGT CAG CTT GGG GCG AAA TAC CCG AAC CTG      2016
Val Gln Arg Gly Thr Gly Arg Gln Leu Gly Ala Lys Tyr Pro Asn Leu
                660                 665                 670
```

```
CAT CTG GCA GGG AAA ACA GGG ACT ACC AAC AAT AAC GTA GAT ACC TGG     2064
His Leu Ala Gly Lys Thr Gly Thr Thr Asn Asn Asn Val Asp Thr Trp
            675                 680                 685

TTT GCG GGC ATT GAC GGC AGC ACG GTG ACC ATC ACC TGG GTC GGC CGT     2112
Phe Ala Gly Ile Asp Gly Ser Thr Val Thr Ile Thr Trp Val Gly Arg
690                 695                 700

GAT AAC AAC CAG CCG ACC AAA CTG TAT GGT GCC AGC GGG GCA ATG TCG     2160
Asp Asn Asn Gln Pro Thr Lys Leu Tyr Gly Ala Ser Gly Ala Met Ser
705                 710                 715                 720

ATT TAT CAG CGT TAT CTG GCT AAC CAG ACG CCA ACG CCG CTG AAT CTT     2208
Ile Tyr Gln Arg Tyr Leu Ala Asn Gln Thr Pro Thr Pro Leu Asn Leu
            725                 730                 735

GTT CCG CCA GAA GAT ATT GCA GAT ATG GGC GTG GAC TAC GAC GGC AAC     2256
Val Pro Pro Glu Asp Ile Ala Asp Met Gly Val Asp Tyr Asp Gly Asn
            740                 745                 750

TTT GTT TGC AGC GGT GGC ATG CGT ATC TTG CCG GTC TGG ACC AGC GAT     2304
Phe Val Cys Ser Gly Gly Met Arg Ile Leu Pro Val Trp Thr Ser Asp
            755                 760                 765

CCG CAA TCG CTG TGC CAG CAG AGC GAG ATG CAG CAG CAG CCG TCA GGC     2352
Pro Gln Ser Leu Cys Gln Gln Ser Glu Met Gln Gln Gln Pro Ser Gly
770                 775                 780

AAT CCG TTT GAT CAG TCT TCT CAG CCG CAG CAA CAG CCG CAA CAG CAA     2400
Asn Pro Phe Asp Gln Ser Ser Gln Pro Gln Gln Gln Pro Gln Gln Gln
785                 790                 795                 800

CCT GCT CAG CAA GAG CAG AAA GAC AGC GAC GGT GTA GCC GGT TGG ATC     2448
Pro Ala Gln Gln Glu Gln Lys Asp Ser Asp Gly Val Ala Gly Trp Ile
            805                 810                 815

AAG GAT ATG TTT GGT AGT AAT TAA                                     2472
Lys Asp Met Phe Gly Ser Asn *
820
```

(2) INFORMATION FOR SEQ ID NO:4:

(i) SEQUENCE CHARACTERISTICS:
        (A) LENGTH: 823 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Gly Asn Asp Arg Glu Pro Ile Gly Arg Lys Gly Lys Pro Thr
1               5                   10                  15

Arg Pro Val Lys Gln Lys Val Ser Arg Arg Tyr Glu Asp Asp
            20                  25                  30

Asp Tyr Asp Asp Tyr Asp Asp Tyr Glu Asp Glu Glu Pro Met Pro Arg
            35                  40                  45

Lys Gly Lys Gly Lys Gly Lys Gly Arg Lys Pro Arg Gly Lys Arg Gly
50                  55                  60

Ser Ile Asp Gln Lys Ile Arg Ser Arg Ile Asp Gly Lys Val Trp Gln
65                  70                  75                  80

Leu Ala Ala Ala Val Tyr Gly Arg Met Val Asn Leu Glu Pro Asp Met
                85                  90                  95

Thr Ile Ser Lys Asn Glu Met Val Lys Leu Leu Glu Ala Thr Gln Tyr
            100                 105                 110

Arg Gln Val Ser Lys Met Thr Arg Pro Gly Glu Phe Thr Val Gln Ala
            115                 120                 125

Asn Ser Ile Glu Met Ile Arg Arg Pro Phe Asp Phe Pro Asp Ser Lys
130                 135                 140
```

-continued

```
Glu Gly Gln Val Arg Ala Arg Leu Thr Phe Asp Gly Asp His Leu Ala
145                 150                 155                 160

Thr Ile Val Asn Met Glu Asn Asn Arg Gln Phe Gly Phe Phe Arg Leu
            165                 170                 175

Asp Pro Arg Leu Ile Thr Met Ile Ser Ser Pro Asn Gly Glu Gln Arg
                180                 185                 190

Leu Phe Val Pro Arg Ser Gly Phe Pro Asp Leu Leu Val Asp Thr Leu
        195                 200                 205

Leu Ala Thr Glu Asp Arg His Phe Tyr Glu His Asp Gly Ile Ser Leu
    210                 215                 220

Tyr Ser Ile Gly Arg Ala Val Leu Ala Asn Leu Thr Ala Gly Arg Thr
225                 230                 235                 240

Val Gln Gly Ala Ser Thr Leu Thr Gln Gln Leu Val Lys Asn Leu Phe
            245                 250                 255

Leu Ser Ser Glu Arg Ser Tyr Trp Arg Lys Ala Asn Glu Ala Tyr Met
            260                 265                 270

Ala Leu Ile Met Asp Ala Arg Tyr Ser Lys Asp Arg Ile Leu Glu Leu
        275                 280                 285

Tyr Met Asn Glu Val Tyr Leu Gly Gln Ser Gly Asp Asn Glu Ile Arg
    290                 295                 300

Gly Phe Pro Leu Ala Ser Leu Tyr Tyr Phe Gly Arg Pro Val Glu Glu
305                 310                 315                 320

Leu Ser Leu Asp Gln Gln Ala Leu Leu Val Gly Met Val Lys Gly Ala
            325                 330                 335

Ser Ile Tyr Asn Pro Trp Arg Asn Pro Lys Leu Ala Leu Glu Arg Arg
            340                 345                 350

Asn Leu Val Leu Arg Leu Leu Gln Gln Gln Ile Ile Asp Gln Glu
        355                 360                 365

Leu Tyr Asp Met Leu Ser Ala Arg Pro Leu Gly Val Gln Pro Arg Gly
    370                 375                 380

Gly Val Ile Ser Pro Gln Pro Ala Phe Met Gln Leu Val Arg Gln Glu
385                 390                 395                 400

Leu Gln Ala Lys Leu Gly Asp Lys Val Lys Asp Leu Ser Gly Val Lys
            405                 410                 415

Ile Phe Thr Thr Phe Asp Ser Val Ala Gln Asp Ala Ala Glu Lys Ala
            420                 425                 430

Ala Val Glu Gly Ile Pro Ala Leu Lys Lys Gln Arg Lys Leu Ser Asp
        435                 440                 445

Leu Glu Thr Ala Ile Val Val Asp Arg Phe Ser Gly Glu Val Arg
    450                 455                 460

Ala Met Val Gly Gly Ser Glu Pro Gln Phe Ala Gly Tyr Asn Arg Ala
465                 470                 475                 480

Met Gln Ala Arg Arg Ser Ile Gly Ser Leu Ala Lys Pro Ala Thr Tyr
            485                 490                 495

Leu Thr Ala Leu Ser Gln Pro Lys Ile Tyr Arg Leu Asn Thr Trp Ile
            500                 505                 510

Ala Asp Ala Pro Ile Ala Leu Arg Gln Pro Asn Gly Gln Val Trp Ser
        515                 520                 525

Pro Gln Asn Asp Asp Arg Arg Tyr Ser Glu Ser Gly Arg Val Met Leu
    530                 535                 540

Val Asp Ala Leu Thr Arg Ser Met Asn Val Pro Thr Val Asn Leu Gly
545                 550                 555                 560

Met Ala Leu Gly Leu Pro Ala Val Thr Glu Thr Trp Ile Lys Leu Gly
            565                 570                 575
```

Val Pro Lys Asp Gln Leu His Pro Val Pro Ala Met Leu Leu Gly Ala
            580                 585                 590

Leu Asn Leu Thr Pro Ile Glu Val Ala Gln Ala Phe Gln Thr Ile Ala
            595                 600                 605

Ser Gly Gly Asn Arg Ala Pro Leu Ser Ala Leu Arg Ser Val Ile Ala
            610                 615                 620

Glu Asp Gly Lys Val Leu Tyr Gln Ser Phe Pro Gln Ala Glu Arg Ala
625                 630                 635                 640

Val Pro Ala Gln Ala Ala Tyr Leu Thr Leu Trp Thr Met Gln Gln Val
            645                 650                 655

Val Gln Arg Gly Thr Gly Arg Gln Leu Gly Ala Lys Tyr Pro Asn Leu
            660                 665                 670

His Leu Ala Gly Lys Thr Gly Thr Thr Asn Asn Val Asp Thr Trp
            675                 680                 685

Phe Ala Gly Ile Asp Gly Ser Thr Val Thr Ile Thr Trp Val Gly Arg
            690                 695                 700

Asp Asn Asn Gln Pro Thr Lys Leu Tyr Gly Ala Ser Gly Ala Met Ser
705                 710                 715                 720

Ile Tyr Gln Arg Tyr Leu Ala Asn Gln Thr Pro Thr Pro Leu Asn Leu
            725                 730                 735

Val Pro Pro Glu Asp Ile Ala Asp Met Gly Val Asp Tyr Asp Gly Asn
            740                 745                 750

Phe Val Cys Ser Gly Gly Met Arg Ile Leu Pro Val Trp Thr Ser Asp
            755                 760                 765

Pro Gln Ser Leu Cys Gln Gln Ser Glu Met Gln Gln Gln Pro Ser Gly
            770                 775                 780

Asn Pro Phe Asp Gln Ser Ser Gln Pro Gln Gln Pro Gln Gln Gln
785                 790                 795                 800

Pro Ala Gln Gln Glu Gln Lys Asp Ser Asp Gly Val Ala Gly Trp Ile
            805                 810                 815

Lys Asp Met Phe Gly Ser Asn
            820

(2) INFORMATION FOR SEQ ID NO:5:

(i) SEQUENCE CHARACTERISTICS:
        (A) LENGTH: 2049 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Streptococcus pneumoniae
        (B) STRAIN: PM 1

(vii) IMMEDIATE SOURCE:
        (A) LIBRARY: PCR cloning
        (B) CLONE: pARC 0512 Soluble PBP 1A del 38

(ix) FEATURE:
        (A) NAME/KEY: CDS
        (B) LOCATION: 1..2049

(ix) FEATURE:
        (A) NAME/KEY: mat_peptide
        (B) LOCATION: 1..2046

(xi) SEQUENCE DESCRIPTION: SEQ ID NO:5:

ATG GCT CCT AGC CTA TCC GAG AGT AAA CTA GTT GCA ACA ACT TCT AGT        48
Met Ala Pro Ser Leu Ser Glu Ser Lys Leu Val Ala Thr Thr Ser Ser

-continued

```
  1                  5                    10                   15
AAA ATC TAC GAC AAT AAA AAT CAA CTC ATT GCT GAC TTG GGT TCT GAA      96
Lys Ile Tyr Asp Asn Lys Asn Gln Leu Ile Ala Asp Leu Gly Ser Glu
                    20                  25                  30

CGC CGC GTC AAT GCC CAA GCT AAT GAT ATT CCC ACA GAT TTG GTT AAG     144
Arg Arg Val Asn Ala Gln Ala Asn Asp Ile Pro Thr Asp Leu Val Lys
                35                  40                  45

GCA ATC GTT TCT ATC GAA GAC CAT CGC TTC TTC GAC CAC AGG GGG ATT     192
Ala Ile Val Ser Ile Glu Asp His Arg Phe Phe Asp His Arg Gly Ile
            50                  55                  60

GAT ACC ATC CGT ATC CTG GGA GCT TTC TTG CGC AAT CTG CAA AGC AAT     240
Asp Thr Ile Arg Ile Leu Gly Ala Phe Leu Arg Asn Leu Gln Ser Asn
65                  70                  75                  80

TCC CTC CAA GGT GGA TCA GCT CTC ACT CAA CAG TTG ATT AAG TTG ACT     288
Ser Leu Gln Gly Gly Ser Ala Leu Thr Gln Gln Leu Ile Lys Leu Thr
                    85                  90                  95

TAC TTT TCA ACT TCG ACT TCC GAC CAG ACT ATT TCT CGT AAG GCT CAG     336
Tyr Phe Ser Thr Ser Thr Ser Asp Gln Thr Ile Ser Arg Lys Ala Gln
                100                 105                 110

GAA GCT TGG TTA GCG ATT CAG TTA GAA CAA AAA GCA ACC AAG CAA GAA     384
Glu Ala Trp Leu Ala Ile Gln Leu Glu Gln Lys Ala Thr Lys Gln Glu
            115                 120                 125

ATC TTG ACC TAC TAT ATA AAT AAG GTC TAC ATG TCT AAT GGG AAC TAT     432
Ile Leu Thr Tyr Tyr Ile Asn Lys Val Tyr Met Ser Asn Gly Asn Tyr
130                 135                 140

GGA ATG CAG ACA GCA GCT CAA AAC TAC TAT GGT AAA GAC CTC AAT AAT     480
Gly Met Gln Thr Ala Ala Gln Asn Tyr Tyr Gly Lys Asp Leu Asn Asn
145                 150                 155                 160

TTA AGT TTA CCT CAG TTA GCC TTG CTG GCT GGA ATG CCT CAG GCA CCA     528
Leu Ser Leu Pro Gln Leu Ala Leu Leu Ala Gly Met Pro Gln Ala Pro
                165                 170                 175

AAC CAA TAT GAC CCC TAT TCA CAT CCA GAA GCA GCC CAA GAC CGC CGA     576
Asn Gln Tyr Asp Pro Tyr Ser His Pro Glu Ala Ala Gln Asp Arg Arg
            180                 185                 190

AAC TTG GTC TTA TCT GAA ATG AAA AAT CAA GGC TAC ATC TCT GCT GAA     624
Asn Leu Val Leu Ser Glu Met Lys Asn Gln Gly Tyr Ile Ser Ala Glu
        195                 200                 205

CAG TAT GAG AAA GCA GTC AAT ACA CCA ATT ACT GAT GGG CTA CAA AGT     672
Gln Tyr Glu Lys Ala Val Asn Thr Pro Ile Thr Asp Gly Leu Gln Ser
210                 215                 220

CTC AAA TCA GCA AGT AAT TAC CCT GCT TAC ATG GAT AAT TAC CTC AAG     720
Leu Lys Ser Ala Ser Asn Tyr Pro Ala Tyr Met Asp Asn Tyr Leu Lys
225                 230                 235                 240

GAA GTC ATC AAT CAA GTT GAA GAA GAA ACA GGC TAT AAC CTA CTC ACA     768
Glu Val Ile Asn Gln Val Glu Glu Glu Thr Gly Tyr Asn Leu Leu Thr
                245                 250                 255

ACT GGG ATG GAT GTC TAC ACA AAT GTA GAC CAA GAA GCT CAA AAA CAT     816
Thr Gly Met Asp Val Tyr Thr Asn Val Asp Gln Glu Ala Gln Lys His
            260                 265                 270

CTG TGG GAT ATT TAC AAT ACA GAC GAA TAC GTT GCC TAT CCA GAC GAT     864
Leu Trp Asp Ile Tyr Asn Thr Asp Glu Tyr Val Ala Tyr Pro Asp Asp
        275                 280                 285

GAA TTG CAA GTC GCT TCT ACC ATT GTT GAT GTT TCT AAC GGT AAA GTC     912
Glu Leu Gln Val Ala Ser Thr Ile Val Asp Val Ser Asn Gly Lys Val
        290                 295                 300

ATT GCC CAG CTA GGA GCA CGC CAT CAG TCA AGT AAT GTT TCC TTC GGA     960
Ile Ala Gln Leu Gly Ala Arg His Gln Ser Ser Asn Val Ser Phe Gly
305                 310                 315                 320

ATT AAC CAA GCA GTA GAA ACA AAC CGC GAC TGG GGA TCA ACT ATG AAA    1008
Ile Asn Gln Ala Val Glu Thr Asn Arg Asp Trp Gly Ser Thr Met Lys
```

```
                  325                 330                 335
CCG ATC ACA GAC TAT GCT CCT GCC TTG GAG TAC GGT GTC TAC GAG TCA       1056
Pro Ile Thr Asp Tyr Ala Pro Ala Leu Glu Tyr Gly Val Tyr Glu Ser
                340                 345                 350

ACT GCC ACT ATC GTT CAC GAT GAG CCC TAT AAC TAC CCT GGG ACA AAT       1104
Thr Ala Thr Ile Val His Asp Glu Pro Tyr Asn Tyr Pro Gly Thr Asn
                355                 360                 365

ACC CCT GTT TAT AAC TGG GAT AGG GGC TAC TTT GGC AAC ATC ACC TTG       1152
Thr Pro Val Tyr Asn Trp Asp Arg Gly Tyr Phe Gly Asn Ile Thr Leu
                370                 375                 380

CAA TAC GCC CTG CAA CAA TCG CGA AAC GTC CCA GCC GTG GAA ACT CTA       1200
Gln Tyr Ala Leu Gln Gln Ser Arg Asn Val Pro Ala Val Glu Thr Leu
385                 390                 395                 400

AAC AAG GTC GGA CTC AAC CGC GCC AAG ACT TTC CTA AAT GGT CTC GGA       1248
Asn Lys Val Gly Leu Asn Arg Ala Lys Thr Phe Leu Asn Gly Leu Gly
                405                 410                 415

ATC GAC TAC CCA AGT ATT CAC TAC TCA AAT GCC ATT TCA AGT AAC ACA       1296
Ile Asp Tyr Pro Ser Ile His Tyr Ser Asn Ala Ile Ser Ser Asn Thr
                420                 425                 430

ACC GAA TCA GAC AAA AAA TAT GGA GCA AGT AGT GAA AAG ATG GCT GCT       1344
Thr Glu Ser Asp Lys Lys Tyr Gly Ala Ser Ser Glu Lys Met Ala Ala
                435                 440                 445

GCT TAC GCT GCC TTT GCA AAT GGT GGA ACT TAC TAT AAA CCA ATG TAT       1392
Ala Tyr Ala Ala Phe Ala Asn Gly Gly Thr Tyr Tyr Lys Pro Met Tyr
450                 455                 460

ATC CAT AAA GTC GTC TTT AGT GAT GGG AGT GAA AAA GAG TTC TCT AAT       1440
Ile His Lys Val Val Phe Ser Asp Gly Ser Glu Lys Glu Phe Ser Asn
465                 470                 475                 480

GTC GGA ACT CGT GCC ATG AAA GAA ACG ACA GCC TAT ATG ATG ACC GAC       1488
Val Gly Thr Arg Ala Met Lys Glu Thr Thr Ala Tyr Met Met Thr Asp
                485                 490                 495

ATG ATG AAA ACA GTC TTG AGT TAT GGA ACT GGA CGA AAT GCC TAT CTT       1536
Met Met Lys Thr Val Leu Ser Tyr Gly Thr Gly Arg Asn Ala Tyr Leu
                500                 505                 510

GCT TGG CTC CCT CAG GCT GGT AAA ACA GGA ACC TCT AAC TAT ACA GAC       1584
Ala Trp Leu Pro Gln Ala Gly Lys Thr Gly Thr Ser Asn Tyr Thr Asp
                515                 520                 525

GAG GAA ATT GAA AAC CAC ATC AAG ACC TCT CAA TTT GTA GCA CCT GAT       1632
Glu Glu Ile Glu Asn His Ile Lys Thr Ser Gln Phe Val Ala Pro Asp
530                 535                 540

GAA CTA TTT GCT GGC TAT ACG CGT AAA TAT TCA ATG GCT GTA TGG ACA       1680
Glu Leu Phe Ala Gly Tyr Thr Arg Lys Tyr Ser Met Ala Val Trp Thr
545                 550                 555                 560

GGC TAT TCT AAC CGT CTG ACA CCA CTT GTA GGC AAT GGC CTT ACG GTC       1728
Gly Tyr Ser Asn Arg Leu Thr Pro Leu Val Gly Asn Gly Leu Thr Val
                565                 570                 575

GCT GCC AAA GTT TAC CGC TCT ATG ATG ACC TAC CTG TCT GAA GGA AGC       1776
Ala Ala Lys Val Tyr Arg Ser Met Met Thr Tyr Leu Ser Glu Gly Ser
                580                 585                 590

AAT CCA GAG GAT TGG AAT ATA CCA GAG GGG CTC TAC AGA AAT GGA GAA       1824
Asn Pro Glu Asp Trp Asn Ile Pro Glu Gly Leu Tyr Arg Asn Gly Glu
                595                 600                 605

TTC GTA TTT AAA AAT GGT GCT CGT TCT ACG TGG AGC TCA CCT GCT CCA       1872
Phe Val Phe Lys Asn Gly Ala Arg Ser Thr Trp Ser Ser Pro Ala Pro
                610                 615                 620

CAA CAA CCC CCA TCA ACT GAA AGT TCA AGC TCA TCA TCA GAT AGT TCA       1920
Gln Gln Pro Pro Ser Thr Glu Ser Ser Ser Ser Ser Ser Asp Ser Ser
625                 630                 635                 640

ACT TCA CAG TCT AGC TCA ACC ACT CCA AGC ACA AAT AAT AGT ACG ACT       1968
Thr Ser Gln Ser Ser Ser Thr Thr Pro Ser Thr Asn Asn Ser Thr Thr
```

```
                       645             650             655
ACC AAT CCT AAC AAT AAT ACG CAA CAA TCA AAT ACA ACC CCT GAT CAA       2016
Thr Asn Pro Asn Asn Asn Thr Gln Gln Ser Asn Thr Thr Pro Asp Gln
                660             665             670

CAA AAT CAG AAT CCT CAA CCA GCA CAA CCA TAA                           2049
Gln Asn Gln Asn Pro Gln Pro Ala Gln Pro *
        675             680
```

(2) INFORMATION FOR SEQ ID NO:6:

(i) SEQUENCE CHARACTERISTICS:
        (A) LENGTH:  682 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Pro Ser Leu Ser Glu Ser Lys Leu Val Ala Thr Thr Ser Ser
 1               5                  10                  15

Lys Ile Tyr Asp Asn Lys Asn Gln Leu Ile Ala Asp Leu Gly Ser Glu
             20                  25                  30

Arg Arg Val Asn Ala Gln Ala Asn Asp Ile Pro Thr Asp Leu Val Lys
         35                  40                  45

Ala Ile Val Ser Ile Glu Asp His Arg Phe Phe Asp His Arg Gly Ile
     50                  55                  60

Asp Thr Ile Arg Ile Leu Gly Ala Phe Leu Arg Asn Leu Gln Ser Asn
 65                  70                  75                  80

Ser Leu Gln Gly Gly Ser Ala Leu Thr Gln Gln Leu Ile Lys Leu Thr
                 85                  90                  95

Tyr Phe Ser Thr Ser Thr Ser Asp Gln Thr Ile Ser Arg Lys Ala Gln
            100                 105                 110

Glu Ala Trp Leu Ala Ile Gln Leu Glu Gln Lys Ala Thr Lys Gln Glu
        115                 120                 125

Ile Leu Thr Tyr Tyr Ile Asn Lys Val Tyr Met Ser Asn Gly Asn Tyr
    130                 135                 140

Gly Met Gln Thr Ala Ala Gln Asn Tyr Tyr Gly Lys Asp Leu Asn Asn
145                 150                 155                 160

Leu Ser Leu Pro Gln Leu Ala Leu Leu Ala Gly Met Pro Gln Ala Pro
                165                 170                 175

Asn Gln Tyr Asp Pro Tyr Ser His Pro Glu Ala Ala Gln Asp Arg Arg
            180                 185                 190

Asn Leu Val Leu Ser Glu Met Lys Asn Gln Gly Tyr Ile Ser Ala Glu
        195                 200                 205

Gln Tyr Glu Lys Ala Val Asn Thr Pro Ile Thr Asp Gly Leu Gln Ser
    210                 215                 220

Leu Lys Ser Ala Ser Asn Tyr Pro Ala Tyr Met Asp Asn Tyr Leu Lys
225                 230                 235                 240

Glu Val Ile Asn Gln Val Glu Glu Thr Gly Tyr Asn Leu Leu Thr
                245                 250                 255

Thr Gly Met Asp Val Tyr Thr Asn Val Asp Gln Glu Ala Gln Lys His
            260                 265                 270

Leu Trp Asp Ile Tyr Asn Thr Asp Glu Tyr Val Ala Tyr Pro Asp Asp
        275                 280                 285

Glu Leu Gln Val Ala Ser Thr Ile Val Asp Val Ser Asn Gly Lys Val
    290                 295                 300

Ile Ala Gln Leu Gly Ala Arg His Gln Ser Ser Asn Val Ser Phe Gly
```

```
              305                 310                 315                 320
        Ile Asn Gln Ala Val Glu Thr Asn Arg Asp Trp Gly Ser Thr Met Lys
                        325                 330                 335

Pro Ile Thr Asp Tyr Ala Pro Ala Leu Glu Tyr Gly Val Tyr Glu Ser
                        340                 345                 350

Thr Ala Thr Ile Val His Asp Glu Pro Tyr Asn Tyr Pro Gly Thr Asn
                        355                 360                 365

Thr Pro Val Tyr Asn Trp Asp Arg Gly Tyr Phe Gly Asn Ile Thr Leu
                        370                 375                 380

Gln Tyr Ala Leu Gln Ser Arg Asn Val Pro Ala Val Glu Thr Leu
        385                 390                 395                 400

Asn Lys Val Gly Leu Asn Arg Ala Lys Thr Phe Leu Asn Gly Leu Gly
                        405                 410                 415

Ile Asp Tyr Pro Ser Ile His Tyr Ser Asn Ala Ile Ser Ser Asn Thr
                        420                 425                 430

Thr Glu Ser Asp Lys Lys Tyr Gly Ala Ser Glu Lys Met Ala Ala
                        435                 440                 445

Ala Tyr Ala Ala Phe Ala Asn Gly Gly Thr Tyr Tyr Lys Pro Met Tyr
                        450                 455                 460

Ile His Lys Val Val Phe Ser Asp Gly Ser Glu Lys Glu Phe Ser Asn
        465                 470                 475                 480

Val Gly Thr Arg Ala Met Lys Glu Thr Thr Ala Tyr Met Met Thr Asp
                        485                 490                 495

Met Met Lys Thr Val Leu Ser Tyr Gly Thr Gly Arg Asn Ala Tyr Leu
                        500                 505                 510

Ala Trp Leu Pro Gln Ala Gly Lys Thr Gly Thr Ser Asn Tyr Thr Asp
                        515                 520                 525

Glu Glu Ile Glu Asn His Ile Lys Thr Ser Gln Phe Val Ala Pro Asp
                        530                 535                 540

Glu Leu Phe Ala Gly Tyr Thr Arg Lys Tyr Ser Met Ala Val Trp Thr
        545                 550                 555                 560

Gly Tyr Ser Asn Arg Leu Thr Pro Leu Val Gly Asn Gly Leu Thr Val
                        565                 570                 575

Ala Ala Lys Val Tyr Arg Ser Met Met Thr Tyr Leu Ser Glu Gly Ser
                        580                 585                 590

Asn Pro Glu Asp Trp Asn Ile Pro Glu Gly Leu Tyr Arg Asn Gly Glu
                        595                 600                 605

Phe Val Phe Lys Asn Gly Ala Arg Ser Thr Trp Ser Ser Pro Ala Pro
                        610                 615                 620

Gln Gln Pro Pro Ser Thr Glu Ser Ser Ser Ser Ser Asp Ser Ser
        625                 630                 635                 640

Thr Ser Gln Ser Ser Ser Thr Thr Pro Ser Thr Asn Asn Ser Thr Thr
                        645                 650                 655

Thr Asn Pro Asn Asn Asn Thr Gln Gln Ser Asn Thr Thr Pro Asp Gln
                        660                 665                 670

Gln Asn Gln Asn Pro Gln Pro Ala Gln Pro
                        675                 680

(2) INFORMATION FOR SEQ ID NO:7:

(i) SEQUENCE CHARACTERISTICS:
            (A) LENGTH: 844 amino acids
            (B) TYPE: amino acid
            (C) STRANDEDNESS:
            (D) TOPOLOGY: linear
```

-continued (ii) MOLECULE TYPE: peptide (vi) ORIGINAL SOURCE:
    (A) ORGANISM: Escherichia coli (vii) IMMEDIATE SOURCE:
    (B) CLONE: pARC0438 PBP 1B QQAA (xi) SEQUENCE DESCRIPTION: SEQ ID NO:7:

```
Met Ala Gly Asn Asp Arg Glu Pro Ile Gly Arg Lys Gly Lys Pro Thr
  1               5                  10                  15

Arg Pro Val Lys Gln Lys Val Ser Arg Arg Tyr Glu Asp Asp Asp
             20                  25                  30

Asp Tyr Asp Asp Tyr Asp Asp Tyr Glu Asp Glu Pro Met Pro Arg
             35                  40                  45

Lys Gly Lys Gly Lys Gly Lys Gly Arg Lys Pro Arg Gly Lys Arg Gly
 50                  55                  60

Trp Leu Trp Leu Leu Lys Leu Ala Ile Val Phe Ala Val Leu Ile
 65                  70                  75                  80

Ala Ile Tyr Gly Val Tyr Leu Asp Gln Lys Ile Arg Ser Arg Ile Asp
                 85                  90                  95

Gly Lys Val Trp Gln Leu Ala Ala Val Tyr Gly Arg Met Val Asn
                100                 105                 110

Leu Glu Pro Asp Met Thr Ile Ser Lys Asn Glu Met Val Lys Leu Leu
                115                 120                 125

Glu Ala Thr Gln Tyr Arg Gln Val Ser Lys Met Thr Arg Pro Gly Glu
130                 135                 140

Phe Thr Val Gln Ala Asn Ser Ile Glu Met Ile Arg Arg Pro Phe Asp
145                 150                 155                 160

Phe Pro Asp Ser Lys Glu Gly Gln Val Arg Ala Arg Leu Thr Phe Asp
                165                 170                 175

Gly Asp His Leu Ala Thr Ile Val Asn Met Glu Asn Asn Arg Gln Phe
                180                 185                 190

Gly Phe Phe Arg Leu Asp Pro Arg Leu Ile Thr Met Ile Ser Ser Pro
                195                 200                 205

Asn Gly Glu Gln Arg Leu Phe Val Pro Arg Ser Gly Phe Pro Asp Leu
210                 215                 220

Leu Val Asp Thr Leu Leu Ala Thr Glu Asp Arg His Phe Tyr Glu His
225                 230                 235                 240

Asp Gly Ile Ser Leu Tyr Ser Ile Gly Arg Ala Val Leu Ala Asn Leu
                245                 250                 255

Thr Ala Gly Arg Thr Val Gln Gly Ala Ser Thr Leu Thr Ala Ala Leu
            260                 265                 270

Val Lys Asn Leu Phe Leu Ser Ser Glu Arg Ser Tyr Trp Arg Lys Ala
275                 280                 285

Asn Glu Ala Tyr Met Ala Leu Ile Met Asp Ala Arg Tyr Ser Lys Asp
290                 295                 300

Arg Ile Leu Glu Leu Tyr Met Asn Glu Val Tyr Leu Gly Gln Ser Gly
305                 310                 315                 320

Asp Asn Glu Ile Arg Gly Phe Pro Leu Ala Ser Leu Tyr Tyr Phe Gly
                325                 330                 335

Arg Pro Val Glu Glu Leu Ser Leu Asp Gln Gln Ala Leu Leu Val Gly
                340                 345                 350

Met Val Lys Gly Ala Ser Ile Tyr Asn Pro Trp Arg Asn Pro Lys Leu
            355                 360                 365

Ala Leu Glu Arg Arg Asn Leu Val Leu Arg Leu Leu Gln Gln Gln Gln
```

```
            370             375             380
Ile Ile Asp Gln Glu Leu Tyr Asp Met Leu Ser Ala Arg Pro Leu Gly
385             390             395             400
Val Gln Pro Arg Gly Gly Val Ile Ser Pro Gln Pro Ala Phe Met Gln
                405             410             415
Leu Val Arg Gln Glu Leu Gln Ala Lys Leu Gly Asp Lys Val Lys Asp
            420             425             430
Leu Ser Gly Val Lys Ile Phe Thr Thr Phe Asp Ser Val Ala Gln Asp
            435             440             445
Ala Ala Glu Lys Ala Ala Val Glu Gly Ile Pro Ala Leu Lys Lys Gln
        450             455             460
Arg Lys Leu Ser Asp Leu Glu Thr Ala Ile Val Val Asp Arg Phe
465             470             475             480
Ser Gly Glu Val Arg Ala Met Val Gly Ser Glu Pro Gln Phe Ala
                485             490             495
Gly Tyr Asn Arg Ala Met Gln Ala Arg Arg Ser Ile Gly Ser Leu Ala
            500             505             510
Lys Pro Ala Thr Tyr Leu Thr Ala Leu Ser Gln Pro Lys Ile Tyr Arg
        515             520             525
Leu Asn Thr Trp Ile Ala Asp Ala Pro Ile Ala Leu Arg Gln Pro Asn
    530             535             540
Gly Gln Val Trp Ser Pro Gln Asn Asp Asp Arg Arg Tyr Ser Glu Ser
545             550             555             560
Gly Arg Val Met Leu Val Asp Ala Leu Thr Arg Ser Met Asn Val Pro
                565             570             575
Thr Val Asn Leu Gly Met Ala Leu Gly Leu Pro Ala Val Thr Glu Thr
            580             585             590
Trp Ile Lys Leu Gly Val Pro Lys Asp Gln Leu His Pro Val Pro Ala
        595             600             605
Met Leu Leu Gly Ala Leu Asn Leu Thr Pro Ile Glu Val Ala Gln Ala
        610             615             620
Phe Gln Thr Ile Ala Ser Gly Gly Asn Arg Ala Pro Leu Ser Ala Leu
625             630             635             640
Arg Ser Val Ile Ala Glu Asp Gly Lys Val Leu Tyr Gln Ser Phe Pro
                645             650             655
Gln Ala Glu Arg Ala Val Pro Ala Gln Ala Ala Tyr Leu Thr Leu Trp
            660             665             670
Thr Met Gln Gln Val Val Gln Arg Gly Thr Gly Arg Gln Leu Gly Ala
            675             680             685
Lys Tyr Pro Asn Leu His Leu Ala Gly Lys Thr Gly Thr Thr Asn Asn
        690             695             700
Asn Val Asp Thr Trp Phe Ala Gly Ile Asp Gly Ser Thr Val Thr Ile
705             710             715             720
Thr Trp Val Gly Arg Asp Asn Asn Gln Pro Thr Lys Leu Tyr Gly Ala
                725             730             735
Ser Gly Ala Met Ser Ile Tyr Gln Arg Tyr Leu Ala Asn Gln Thr Pro
            740             745             750
Thr Pro Leu Asn Leu Val Pro Pro Glu Asp Ile Ala Asp Met Gly Val
        755             760             765
Asp Tyr Asp Gly Asn Phe Val Cys Ser Gly Gly Met Arg Ile Leu Pro
        770             775             780
Val Trp Thr Ser Asp Pro Gln Ser Leu Cys Gln Gln Ser Glu Met Gln
785             790             795             800
```

-continued

```
Gln Gln Pro Ser Gly Asn Pro Phe Asp Gln Ser Ser Gln Pro Gln Gln
            805                 810                 815

Gln Pro Gln Gln Gln Pro Ala Gln Glu Gln Lys Asp Ser Asp Gly
        820                 825                 830

Val Ala Gly Trp Ile Lys Asp Met Phe Gly Ser Asn
        835                 840
```

(2) INFORMATION FOR SEQ ID NO:8:

(i) SEQUENCE CHARACTERISTICS:
        (A) LENGTH: 844 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Escherichia coli (vii) IMMEDIATE SOURCE:
        (B) CLONE: pARC0468 PBP 1B QQLL (xi) SEQUENCE DESCRIPTION: SEQ ID NO:8:

```
Met Ala Gly Asn Asp Arg Glu Pro Ile Gly Arg Lys Gly Lys Pro Thr
1               5                   10                  15

Arg Pro Val Lys Gln Lys Val Ser Arg Arg Tyr Glu Asp Asp Asp
        20                  25                  30

Asp Tyr Asp Asp Tyr Asp Asp Tyr Glu Asp Glu Glu Pro Met Pro Arg
        35                  40                  45

Lys Gly Lys Gly Lys Gly Lys Gly Arg Lys Pro Arg Gly Lys Arg Gly
        50                  55                  60

Trp Leu Trp Leu Leu Leu Lys Leu Ala Ile Val Phe Ala Val Leu Ile
65                  70                  75                  80

Ala Ile Tyr Gly Val Tyr Leu Asp Gln Lys Ile Arg Ser Arg Ile Asp
                85                  90                  95

Gly Lys Val Trp Gln Leu Ala Ala Ala Val Tyr Gly Arg Met Val Asn
                100                 105                 110

Leu Glu Pro Asp Met Thr Ile Ser Lys Asn Glu Met Val Lys Leu Leu
            115                 120                 125

Glu Ala Thr Gln Tyr Arg Gln Val Ser Lys Met Thr Arg Pro Gly Glu
        130                 135                 140

Phe Thr Val Gln Ala Asn Ser Ile Glu Met Ile Arg Arg Pro Phe Asp
145                 150                 155                 160

Phe Pro Asp Ser Lys Glu Gly Gln Val Arg Ala Arg Leu Thr Phe Asp
                165                 170                 175

Gly Asp His Leu Ala Thr Ile Val Asn Met Glu Asn Asn Arg Gln Phe
            180                 185                 190

Gly Phe Phe Arg Leu Asp Pro Arg Leu Ile Thr Met Ile Ser Ser Pro
        195                 200                 205

Asn Gly Glu Gln Arg Leu Phe Val Pro Arg Ser Gly Phe Pro Asp Leu
    210                 215                 220

Leu Val Asp Thr Leu Leu Ala Thr Glu Asp Arg His Phe Tyr Glu His
225                 230                 235                 240

Asp Gly Ile Ser Leu Tyr Ser Ile Gly Arg Ala Val Leu Ala Asn Leu
                245                 250                 255

Thr Ala Gly Arg Thr Val Gln Gly Ala Ser Thr Leu Thr Leu Leu
            260                 265                 270

Val Lys Asn Leu Phe Leu Ser Ser Glu Arg Ser Tyr Trp Arg Lys Ala
```

```
                    275                 280                 285
Asn Glu Ala Tyr Met Ala Leu Ile Met Asp Ala Arg Tyr Ser Lys Asp
    290                 295                 300

Arg Ile Leu Glu Leu Tyr Met Asn Glu Val Tyr Leu Gly Gln Ser Gly
305                 310                 315                 320

Asp Asn Glu Ile Arg Gly Phe Pro Leu Ala Ser Leu Tyr Tyr Phe Gly
                325                 330                 335

Arg Pro Val Glu Glu Leu Ser Leu Asp Gln Gln Ala Leu Leu Val Gly
            340                 345                 350

Met Val Lys Gly Ala Ser Ile Tyr Asn Pro Trp Arg Asn Pro Lys Leu
        355                 360                 365

Ala Leu Glu Arg Arg Asn Leu Val Leu Arg Leu Leu Gln Gln Gln Gln
    370                 375                 380

Ile Ile Asp Gln Glu Leu Tyr Asp Met Leu Ser Ala Arg Pro Leu Gly
385                 390                 395                 400

Val Gln Pro Arg Gly Gly Val Ile Ser Pro Gln Pro Ala Phe Met Gln
                405                 410                 415

Leu Val Arg Gln Glu Leu Gln Ala Lys Leu Gly Asp Lys Val Lys Asp
            420                 425                 430

Leu Ser Gly Val Lys Ile Phe Thr Thr Phe Asp Ser Val Ala Gln Asp
        435                 440                 445

Ala Ala Glu Lys Ala Ala Val Glu Gly Ile Pro Ala Leu Lys Lys Gln
    450                 455                 460

Arg Lys Leu Ser Asp Leu Glu Thr Ala Ile Val Val Asp Arg Phe
465                 470                 475                 480

Ser Gly Glu Val Arg Ala Met Val Gly Gly Ser Glu Pro Gln Phe Ala
                485                 490                 495

Gly Tyr Asn Arg Ala Met Gln Ala Arg Arg Ser Ile Gly Ser Leu Ala
            500                 505                 510

Lys Pro Ala Thr Tyr Leu Thr Ala Leu Ser Gln Pro Lys Ile Tyr Arg
        515                 520                 525

Leu Asn Thr Trp Ile Ala Asp Ala Pro Ile Ala Leu Arg Gln Pro Asn
    530                 535                 540

Gly Gln Val Trp Ser Pro Gln Asn Asp Asp Arg Arg Tyr Ser Glu Ser
545                 550                 555                 560

Gly Arg Val Met Leu Val Asp Ala Leu Thr Arg Ser Met Asn Val Pro
                565                 570                 575

Thr Val Asn Leu Gly Met Ala Leu Gly Leu Pro Ala Val Thr Glu Thr
            580                 585                 590

Trp Ile Lys Leu Gly Val Pro Lys Asp Gln Leu His Pro Val Pro Ala
        595                 600                 605

Met Leu Leu Gly Ala Leu Asn Leu Thr Pro Ile Glu Val Ala Gln Ala
    610                 615                 620

Phe Gln Thr Ile Ala Ser Gly Gly Asn Arg Ala Pro Leu Ser Ala Leu
625                 630                 635                 640

Arg Ser Val Ile Ala Glu Asp Gly Lys Val Leu Tyr Gln Ser Phe Pro
                645                 650                 655

Gln Ala Glu Arg Ala Val Pro Ala Gln Ala Ala Tyr Leu Thr Leu Trp
            660                 665                 670

Thr Met Gln Gln Val Val Gln Arg Gly Thr Gly Arg Gln Leu Gly Ala
        675                 680                 685

Lys Tyr Pro Asn Leu His Leu Ala Gly Lys Thr Gly Thr Thr Asn Asn
    690                 695                 700
```

-continued

```
Asn Val Asp Thr Trp Phe Ala Gly Ile Asp Gly Ser Thr Val Thr Ile
705                 710                 715                 720

Thr Trp Val Gly Arg Asp Asn Asn Gln Pro Thr Lys Leu Tyr Gly Ala
            725                 730                 735

Ser Gly Ala Met Ser Ile Tyr Gln Arg Tyr Leu Ala Asn Gln Thr Pro
        740                 745                 750

Thr Pro Leu Asn Leu Val Pro Pro Glu Asp Ile Ala Asp Met Gly Val
        755                 760                 765

Asp Tyr Asp Gly Asn Phe Val Cys Ser Gly Gly Met Arg Ile Leu Pro
    770                 775                 780

Val Trp Thr Ser Asp Pro Gln Ser Leu Cys Gln Gln Ser Glu Met Gln
785                 790                 795                 800

Gln Gln Pro Ser Gly Asn Pro Phe Asp Gln Ser Ser Gln Pro Gln Gln
                805                 810                 815

Gln Pro Gln Gln Gln Pro Ala Gln Gln Glu Gln Lys Asp Ser Asp Gly
            820                 825                 830

Val Ala Gly Trp Ile Lys Asp Met Phe Gly Ser Asn
            835                 840
```

(2) INFORMATION FOR SEQ ID NO:9:

(i) SEQUENCE CHARACTERISTICS:
        (A) LENGTH: 836 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Escherichia coli (vii) IMMEDIATE SOURCE:
        (B) CLONE: pARC0469 PBP 1B del 8

(xi) SEQUENCE DESCRIPTION: SEQ ID NO:9:

```
Met Ala Gly Asn Asp Arg Glu Pro Ile Gly Arg Lys Gly Lys Pro Thr
1               5                   10                  15

Arg Pro Val Lys Gln Lys Val Ser Arg Arg Tyr Glu Asp Asp Asp Asp
            20                  25                  30

Asp Tyr Asp Tyr Asp Asp Tyr Glu Asp Glu Pro Met Pro Arg
        35                  40                  45

Lys Gly Lys Gly Lys Gly Lys Gly Arg Lys Pro Arg Gly Lys Arg Gly
        50                  55                  60

Trp Leu Trp Leu Leu Leu Lys Leu Ala Ile Val Phe Ala Val Leu Ile
65                  70                  75                  80

Ala Ile Tyr Gly Val Tyr Leu Asp Gln Lys Ile Arg Ser Arg Ile Asp
            85                  90                  95

Gly Lys Val Trp Gln Leu Ala Ala Val Tyr Gly Arg Met Val Asn
            100                 105                 110

Leu Glu Pro Asp Met Thr Ile Ser Lys Asn Glu Met Val Lys Leu Leu
        115                 120                 125

Glu Ala Thr Gln Tyr Arg Gln Val Ser Lys Met Thr Arg Pro Gly Glu
    130                 135                 140

Phe Thr Val Gln Ala Asn Ser Ile Glu Met Ile Arg Arg Pro Phe Asp
145                 150                 155                 160

Phe Pro Asp Ser Lys Glu Gly Val Arg Ala Arg Leu Thr Phe Asp
            165                 170                 175

Gly Asp His Leu Ala Thr Ile Val Asn Met Glu Asn Asn Arg Gln Phe
```

```
                    180                 185                 190
Gly Phe Phe Arg Leu Asp Pro Arg Leu Ile Thr Met Ile Ser Ser Pro
            195                 200                 205

Asn Gly Glu Gln Arg Leu Phe Val Pro Arg Ser Gly Phe Pro Asp Leu
    210                 215                 220

Leu Val Asp Thr Leu Leu Ala Thr Glu Asp Arg His Phe Tyr Glu His
225                 230                 235                 240

Asp Gly Ile Ser Leu Tyr Ser Ile Gly Arg Ala Val Leu Ala Asn Leu
                245                 250                 255

Thr Ala Gly Arg Thr Val Gln Leu Val Lys Asn Leu Phe Leu Ser Ser
            260                 265                 270

Glu Arg Ser Tyr Trp Arg Lys Ala Asn Glu Ala Tyr Met Ala Leu Ile
    275                 280                 285

Met Asp Ala Arg Tyr Ser Lys Asp Arg Ile Leu Glu Leu Tyr Met Asn
290                 295                 300

Glu Val Tyr Leu Gly Gln Ser Gly Asp Asn Glu Ile Arg Gly Phe Pro
305                 310                 315                 320

Leu Ala Ser Leu Tyr Tyr Phe Gly Arg Pro Val Glu Glu Leu Ser Leu
                325                 330                 335

Asp Gln Gln Ala Leu Leu Val Gly Met Val Lys Gly Ala Ser Ile Tyr
            340                 345                 350

Asn Pro Trp Arg Asn Pro Lys Leu Ala Leu Glu Arg Arg Asn Leu Val
    355                 360                 365

Leu Arg Leu Leu Gln Gln Gln Ile Ile Asp Gln Glu Leu Tyr Asp
370                 375                 380

Met Leu Ser Ala Arg Pro Leu Gly Val Gln Pro Arg Gly Gly Val Ile
385                 390                 395                 400

Ser Pro Gln Pro Ala Phe Met Gln Leu Val Arg Gln Glu Leu Gln Ala
                405                 410                 415

Lys Leu Gly Asp Lys Val Lys Asp Leu Ser Gly Val Lys Ile Phe Thr
            420                 425                 430

Thr Phe Asp Ser Val Ala Gln Asp Ala Ala Glu Lys Ala Ala Val Glu
    435                 440                 445

Gly Ile Pro Ala Leu Lys Lys Gln Arg Lys Leu Ser Asp Leu Glu Thr
450                 455                 460

Ala Ile Val Val Asp Arg Phe Ser Gly Glu Val Arg Ala Met Val
465                 470                 475                 480

Gly Gly Ser Glu Pro Gln Phe Ala Gly Tyr Asn Arg Ala Met Gln Ala
                485                 490                 495

Arg Arg Ser Ile Gly Ser Leu Ala Lys Pro Ala Thr Tyr Leu Thr Ala
            500                 505                 510

Leu Ser Gln Pro Lys Ile Tyr Arg Leu Asn Thr Trp Ile Ala Asp Ala
    515                 520                 525

Pro Ile Ala Leu Arg Gln Pro Asn Gly Gln Val Trp Ser Pro Gln Asn
530                 535                 540

Asp Asp Arg Arg Tyr Ser Glu Ser Gly Arg Val Met Leu Val Asp Ala
545                 550                 555                 560

Leu Thr Arg Ser Met Asn Val Pro Thr Val Asn Leu Gly Met Ala Leu
                565                 570                 575

Gly Leu Pro Ala Val Thr Glu Thr Trp Ile Lys Leu Gly Val Pro Lys
            580                 585                 590

Asp Gln Leu His Pro Val Pro Ala Met Leu Leu Gly Ala Leu Asn Leu
    595                 600                 605
```

-continued

```
Thr Pro Ile Glu Val Ala Gln Ala Phe Gln Thr Ile Ala Ser Gly Gly
    610                 615                 620
Asn Arg Ala Pro Leu Ser Ala Leu Arg Ser Val Ile Ala Glu Asp Gly
625                 630                 635                 640
Lys Val Leu Tyr Gln Ser Phe Pro Gln Ala Glu Arg Ala Val Pro Ala
                645                 650                 655
Gln Ala Ala Tyr Leu Thr Leu Trp Thr Met Gln Gln Val Val Gln Arg
                660                 665                 670
Gly Thr Gly Arg Gln Leu Gly Ala Lys Tyr Pro Asn Leu His Leu Ala
            675                 680                 685
Gly Lys Thr Gly Thr Thr Asn Asn Asn Val Asp Thr Trp Phe Ala Gly
        690                 695                 700
Ile Asp Gly Ser Thr Val Thr Ile Thr Trp Val Gly Arg Asp Asn Asn
705                 710                 715                 720
Gln Pro Thr Lys Leu Tyr Gly Ala Ser Gly Ala Met Ser Ile Tyr Gln
                725                 730                 735
Arg Tyr Leu Ala Asn Gln Thr Pro Thr Pro Leu Asn Leu Val Pro Pro
                740                 745                 750
Glu Asp Ile Ala Asp Met Gly Val Asp Tyr Asp Gly Asn Phe Val Cys
            755                 760                 765
Ser Gly Gly Met Arg Ile Leu Pro Val Trp Thr Ser Asp Pro Gln Ser
        770                 775                 780
Leu Cys Gln Gln Ser Glu Met Gln Gln Pro Ser Gly Asn Pro Phe
785                 790                 795                 800
Asp Gln Ser Ser Gln Pro Gln Gln Pro Gln Gln Pro Ala Gln
                805                 810                 815
Gln Glu Gln Lys Asp Ser Asp Gly Val Ala Gly Trp Ile Lys Asp Met
            820                 825                 830
Phe Gly Ser Asn
        835
```

(2) INFORMATION FOR SEQ ID NO:10:

(i) SEQUENCE CHARACTERISTICS:
        (A) LENGTH: 850 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Escherichia coli (vii) IMMEDIATE SOURCE:
        (B) CLONE: pARC0571 PBP 1A QQAA (xi) SEQUENCE DESCRIPTION: SEQ ID NO:10:

```
Met Lys Phe Val Lys Tyr Phe Leu Ile Leu Ala Val Cys Cys Ile Leu
1               5                   10                  15
Leu Gly Ala Gly Ser Ile Tyr Gly Leu Tyr Arg Tyr Ile Glu Pro Gln
            20                  25                  30
Leu Pro Asp Val Ala Thr Leu Lys Asp Val Arg Leu Gln Ile Pro Met
        35                  40                  45
Gln Ile Tyr Ser Ala Asp Gly Glu Leu Ile Ala Gln Tyr Gly Glu Lys
    50                  55                  60
Arg Arg Ile Pro Val Thr Leu Asp Gln Ile Pro Pro Glu Met Val Lys
65                  70                  75                  80
Ala Phe Ile Ala Thr Glu Asp Ser Arg Phe Tyr Glu His His Gly Val
```

```
                    85                  90                  95
Asp Pro Val Gly Ile Phe Arg Ala Ala Ser Val Ala Leu Phe Ser Gly
                100                 105                 110

His Ala Ser Gln Gly Ala Ser Thr Ile Thr Ala Ala Leu Ala Arg Asn
                115                 120                 125

Phe Phe Leu Ser Pro Glu Arg Thr Leu Met Arg Lys Ile Lys Glu Val
            130                 135                 140

Phe Leu Ala Ile Arg Ile Glu Gln Leu Leu Thr Lys Asp Glu Ile Leu
145                 150                 155                 160

Glu Leu Tyr Leu Asn Lys Ile Tyr Leu Gly Tyr Arg Ala Tyr Gly Val
                165                 170                 175

Gly Ala Ala Ala Gln Val Tyr Phe Gly Lys Thr Val Asp Gln Leu Thr
                180                 185                 190

Leu Asn Glu Met Ala Val Ile Ala Gly Leu Pro Lys Ala Pro Ser Thr
            195                 200                 205

Phe Asn Pro Leu Tyr Ser Met Asp Arg Ala Val Ala Arg Arg Asn Val
        210                 215                 220

Val Leu Ser Arg Met Leu Asp Glu Gly Tyr Ile Thr Gln Gln Gln Phe
225                 230                 235                 240

Asp Gln Thr Arg Thr Glu Ala Ile Asn Ala Asn Tyr His Ala Pro Glu
                245                 250                 255

Ile Ala Phe Ser Ala Pro Tyr Leu Ser Glu Met Val Arg Gln Glu Met
                260                 265                 270

Tyr Asn Arg Tyr Gly Glu Ser Ala Tyr Glu Asp Gly Tyr Arg Ile Tyr
            275                 280                 285

Thr Thr Ile Thr Arg Lys Val Gln Gln Ala Ala Gln Ala Val Arg
            290                 295                 300

Asn Asn Val Leu Asp Tyr Asp Met Arg His Gly Tyr Arg Gly Pro Ala
305                 310                 315                 320

Asn Val Leu Trp Lys Val Gly Glu Ser Ala Trp Asp Asn Asn Lys Ile
                325                 330                 335

Thr Asp Thr Leu Lys Ala Leu Pro Thr Tyr Gly Pro Leu Leu Pro Ala
                340                 345                 350

Ala Val Thr Ser Ala Asn Pro Gln Gln Ala Thr Ala Met Leu Ala Asp
            355                 360                 365

Gly Ser Thr Val Ala Leu Ser Met Glu Gly Val Arg Trp Ala Arg Pro
        370                 375                 380

Tyr Arg Ser Asp Thr Gln Gln Gly Pro Thr Pro Arg Lys Val Thr Asp
385                 390                 395                 400

Val Leu Gln Thr Gly Gln Gln Ile Trp Val Arg Gln Val Gly Asp Ala
                405                 410                 415

Trp Trp Leu Ala Gln Val Pro Glu Val Asn Ser Ala Leu Val Ser Ile
                420                 425                 430

Asn Pro Gln Asn Gly Ala Val Met Ala Leu Val Gly Gly Phe Asp Phe
            435                 440                 445

Asn Gln Ser Lys Phe Asn Arg Ala Thr Gln Ala Leu Arg Gln Val Gly
        450                 455                 460

Ser Asn Ile Lys Pro Phe Leu Tyr Thr Ala Ala Met Asp Lys Gly Leu
465                 470                 475                 480

Thr Leu Ala Ser Met Leu Asn Asp Val Pro Ile Ser Arg Trp Asp Ala
                485                 490                 495

Ser Ala Gly Ser Asp Trp Gln Pro Lys Asn Ser Pro Pro Gln Tyr Ala
            500                 505                 510
```

```
Gly Pro Ile Arg Leu Arg Gln Gly Leu Gly Gln Ser Lys Asn Val Val
            515                 520                 525

Met Val Arg Ala Met Arg Ala Met Gly Val Asp Tyr Ala Ala Glu Tyr
        530                 535                 540

Leu Gln Arg Phe Gly Phe Pro Ala Gln Asn Ile Val His Thr Glu Ser
545                 550                 555                 560

Leu Ala Leu Gly Ser Ala Ser Phe Thr Pro Met Gln Val Ala Arg Gly
                565                 570                 575

Tyr Ala Val Met Ala Asn Gly Gly Phe Leu Val Asp Pro Trp Phe Ile
            580                 585                 590

Ser Lys Ile Glu Asn Asp Gln Gly Gly Val Ile Phe Glu Ala Lys Pro
        595                 600                 605

Lys Val Ala Cys Pro Glu Cys Asp Ile Pro Val Ile Tyr Gly Asp Thr
            610                 615                 620

Gln Lys Ser Asn Val Leu Glu Asn Asn Asp Val Glu Asp Val Ala Ile
625                 630                 635                 640

Ser Arg Glu Gln Gln Asn Val Ser Val Pro Met Pro Gln Leu Glu Gln
                645                 650                 655

Ala Asn Gln Ala Leu Val Ala Lys Thr Gly Ala Gln Glu Tyr Ala Pro
            660                 665                 670

His Val Ile Asn Thr Pro Leu Ala Phe Leu Ile Lys Ser Ala Leu Asn
        675                 680                 685

Thr Asn Ile Phe Gly Glu Pro Gly Trp Gln Gly Thr Gly Trp Arg Ala
        690                 695                 700

Gly Arg Asp Leu Gln Arg Arg Asp Ile Gly Gly Lys Thr Gly Thr Thr
705                 710                 715                 720

Asn Ser Ser Lys Asp Ala Trp Phe Ser Gly Tyr Gly Pro Gly Val Val
                725                 730                 735

Thr Ser Val Trp Ile Gly Phe Asp Asp His Arg Arg Asn Leu Gly His
            740                 745                 750

Thr Thr Ala Ser Gly Ala Ile Lys Asp Gln Ile Ser Gly Tyr Glu Gly
        755                 760                 765

Gly Ala Lys Ser Ala Gln Pro Ala Trp Asp Ala Tyr Met Lys Ala Val
        770                 775                 780

Leu Glu Gly Val Pro Glu Gln Pro Leu Thr Pro Pro Gly Ile Val
785                 790                 795                 800

Thr Val Asn Ile Asp Arg Ser Thr Gly Gln Leu Ala Asn Gly Gly Asn
                805                 810                 815

Ser Arg Glu Glu Tyr Phe Ile Glu Gly Thr Gln Pro Thr Gln Gln Ala
            820                 825                 830

Val His Glu Val Gly Thr Thr Ile Ile Asp Asn Gly Glu Ala Gln Glu
        835                 840                 845

Leu Phe
    850

(2) INFORMATION FOR SEQ ID NO:11:

(i) SEQUENCE CHARACTERISTICS:
        (A) LENGTH: 553 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Escherichia coli
```

(vii) IMMEDIATE SOURCE:
       (B) CLONE: pARC 0592 truncated PBP 1B (xi) SEQUENCE DESCRIPTION: SEQ ID NO:11:

| | | | | | | | | | | | | | | |
|---|---|---|---|---|---|---|---|---|---|---|---|---|---|---|
| Met | Ala | Gly | Asn | Asp | Arg | Glu | Pro | Ile | Gly | Arg | Lys | Gly | Lys | Pro | Thr |
| 1 | | | | 5 | | | | | 10 | | | | | 15 |

Arg Pro Val Lys Gln Lys Val Ser Arg Arg Tyr Glu Asp Asp
            20                  25                  30

Asp Tyr Asp Asp Tyr Asp Asp Tyr Glu Asp Glu Glu Pro Met Pro Arg
                35                  40                      45

Lys Gly Lys Gly Lys Gly Lys Gly Arg Lys Pro Arg Gly Lys Arg Gly
        50                      55                  60

Trp Leu Trp Leu Leu Lys Leu Ala Ile Val Phe Ala Val Leu Ile
65                      70                  75                      80

Ala Ile Tyr Gly Val Tyr Leu Asp Gln Lys Ile Arg Ser Arg Ile Asp
                85                  90                      95

Gly Lys Val Trp Gln Leu Ala Ala Val Tyr Gly Arg Met Val Asn
                100                 105                 110

Leu Glu Pro Asp Met Thr Ile Ser Lys Asn Glu Met Val Lys Leu Leu
            115                 120                 125

Glu Ala Thr Gln Tyr Arg Gln Val Ser Lys Met Thr Arg Pro Gly Glu
        130                 135                 140

Phe Thr Val Gln Ala Asn Ser Ile Glu Met Ile Arg Arg Pro Phe Asp
145                 150                 155                 160

Phe Pro Asp Ser Lys Glu Gly Gln Val Arg Ala Arg Leu Thr Phe Asp
                165                 170                 175

Gly Asp His Leu Ala Thr Ile Val Asn Met Glu Asn Asn Arg Gln Phe
            180                 185                 190

Gly Phe Phe Arg Leu Asp Pro Arg Leu Ile Thr Met Ile Ser Ser Pro
        195                 200                 205

Asn Gly Glu Gln Arg Leu Phe Val Pro Arg Ser Gly Phe Pro Asp Leu
210                 215                 220

Leu Val Asp Thr Leu Leu Ala Thr Glu Asp Arg His Phe Tyr Glu His
225                 230                 235                 240

Asp Gly Ile Ser Leu Tyr Ser Ile Gly Arg Ala Val Leu Ala Asn Leu
            245                 250                 255

Thr Ala Gly Arg Thr Val Gln Gly Ala Ser Thr Leu Thr Gln Gln Leu
        260                 265                 270

Val Lys Asn Leu Phe Leu Ser Ser Glu Arg Ser Tyr Trp Arg Lys Ala
            275                 280                 285

Asn Glu Ala Tyr Met Ala Leu Ile Met Asp Ala Arg Tyr Ser Lys Asp
290                 295                 300

Arg Ile Leu Glu Leu Tyr Met Asn Glu Val Tyr Leu Gly Gln Ser Gly
305                 310                 315                 320

Asp Asn Glu Ile Arg Gly Phe Pro Leu Ala Ser Leu Tyr Tyr Phe Gly
                325                 330                 335

Arg Pro Val Glu Glu Leu Ser Leu Asp Gln Gln Ala Leu Leu Val Gly
            340                 345                 350

Met Val Lys Gly Ala Ser Ile Tyr Asn Pro Trp Arg Asn Pro Lys Leu
        355                 360                 365

Ala Leu Glu Arg Arg Asn Leu Val Leu Arg Leu Gln Gln Gln Gln
370                 375                 380

Ile Ile Asp Gln Glu Leu Tyr Asp Met Leu Ser Ala Arg Pro Leu Gly
385                 390                 395                 400

-continued

```
Val Gln Pro Arg Gly Gly Val Ile Ser Pro Gln Pro Ala Phe Met Gln
                405                 410                 415

Leu Val Arg Gln Glu Leu Gln Ala Lys Leu Gly Asp Lys Val Lys Asp
            420                 425                 430

Leu Ser Gly Val Lys Ile Phe Thr Thr Phe Asp Ser Val Ala Gln Asp
        435                 440                 445

Ala Ala Glu Lys Ala Ala Val Glu Gly Ile Pro Ala Leu Lys Lys Gln
    450                 455                 460

Arg Lys Leu Ser Asp Leu Glu Thr Ala Ile Val Val Asp Arg Phe
465                 470                 475                 480

Ser Gly Glu Val Arg Ala Met Val Gly Ser Glu Pro Gln Phe Ala
                485                 490                 495

Gly Tyr Asn Arg Ala Met Gln Ala Arg Arg Ser Ile Gly Ser Leu Ala
            500                 505                 510

Lys Pro Ala Thr Tyr Leu Thr Ala Leu Ser Gln Pro Lys Ile Tyr Arg
        515                 520                 525

Leu Asn Thr Trp Ile Ala Asp Ala Pro Ile Ala Leu Arg Gln Pro Asn
    530                 535                 540

Gly Gln Val Trp Ser Pro Gln Asn Asp
545                 550
```

(2) INFORMATION FOR SEQ ID NO:12:

(i) SEQUENCE CHARACTERISTICS:
        (A) LENGTH: 532 amino acids
        (B) TYPE: amino acid
        (C) STRANDEDNESS:
        (D) TOPOLOGY: linear (ii) MOLECULE TYPE: peptide (vi) ORIGINAL SOURCE:
        (A) ORGANISM: Escherichia coli (vii) IMMEDIATE SOURCE:
        (B) CLONE: pARC 0593   truncated soluble PBP 1B (xi) SEQUENCE DESCRIPTION: SEQ ID NO:12:

```
Met Ala Gly Asn Asp Arg Glu Pro Ile Gly Arg Lys Gly Lys Pro Thr
1               5                   10                  15

Arg Pro Val Lys Gln Lys Val Ser Arg Arg Tyr Glu Asp Asp Asp
            20                  25                  30

Asp Tyr Asp Asp Tyr Asp Asp Tyr Glu Asp Glu Glu Pro Met Pro Arg
        35                  40                  45

Lys Gly Lys Gly Lys Gly Lys Gly Arg Lys Pro Arg Gly Lys Arg Gly
    50                  55                  60

Ser Ile Asp Gln Lys Ile Arg Ser Arg Ile Asp Gly Lys Val Trp Gln
65                  70                  75                  80

Leu Ala Ala Ala Val Tyr Gly Arg Met Val Asn Leu Glu Pro Asp Met
                85                  90                  95

Thr Ile Ser Lys Asn Glu Met Val Lys Leu Leu Glu Ala Thr Gln Tyr
            100                 105                 110

Arg Gln Val Ser Lys Met Thr Arg Pro Gly Glu Phe Thr Val Gln Ala
        115                 120                 125

Asn Ser Ile Glu Met Ile Arg Arg Pro Phe Asp Phe Pro Asp Ser Lys
    130                 135                 140

Glu Gly Gln Val Arg Ala Arg Leu Thr Phe Asp Gly Asp His Leu Ala
145                 150                 155                 160

Thr Ile Val Asn Met Glu Asn Asn Arg Gln Phe Gly Phe Phe Arg Leu
```

```
                165                 170                 175
Asp Pro Arg Leu Ile Thr Met Ile Ser Ser Pro Asn Gly Glu Gln Arg
            180                 185                 190

Leu Phe Val Pro Arg Ser Gly Phe Pro Asp Leu Leu Val Asp Thr Leu
            195                 200                 205

Leu Ala Thr Glu Asp Arg His Phe Tyr Glu His Asp Gly Ile Ser Leu
            210                 215                 220

Tyr Ser Ile Gly Arg Ala Val Leu Ala Asn Leu Thr Ala Gly Arg Thr
225                 230                 235                 240

Val Gln Gly Ala Ser Thr Leu Thr Gln Gln Leu Val Lys Asn Leu Phe
            245                 250                 255

Leu Ser Ser Glu Arg Ser Tyr Trp Arg Lys Ala Asn Glu Ala Tyr Met
            260                 265                 270

Ala Leu Ile Met Asp Ala Arg Tyr Ser Lys Asp Arg Ile Leu Glu Leu
            275                 280                 285

Tyr Met Asn Glu Val Tyr Leu Gly Gln Ser Gly Asp Asn Glu Ile Arg
            290                 295                 300

Gly Phe Pro Leu Ala Ser Leu Tyr Tyr Phe Gly Arg Pro Val Glu Glu
305                 310                 315                 320

Leu Ser Leu Asp Gln Gln Ala Leu Leu Val Gly Met Val Lys Gly Ala
            325                 330                 335

Ser Ile Tyr Asn Pro Trp Arg Asn Pro Lys Leu Ala Leu Glu Arg Arg
            340                 345                 350

Asn Leu Val Leu Arg Leu Leu Gln Gln Gln Ile Ile Asp Gln Glu
            355                 360                 365

Leu Tyr Asp Met Leu Ser Ala Arg Pro Leu Gly Val Gln Pro Arg Gly
            370                 375                 380

Gly Val Ile Ser Pro Gln Pro Ala Phe Met Gln Leu Val Arg Gln Glu
385                 390                 395                 400

Leu Gln Ala Lys Leu Gly Asp Lys Val Lys Asp Leu Ser Gly Val Lys
            405                 410                 415

Ile Phe Thr Thr Phe Asp Ser Val Ala Gln Asp Ala Ala Glu Lys Ala
            420                 425                 430

Ala Val Glu Gly Ile Pro Ala Leu Lys Lys Gln Arg Lys Leu Ser Asp
            435                 440                 445

Leu Glu Thr Ala Ile Val Val Val Asp Arg Phe Ser Gly Glu Val Arg
450                 455                 460

Ala Met Val Gly Gly Ser Glu Pro Gln Phe Ala Gly Tyr Asn Arg Ala
465                 470                 475                 480

Met Gln Ala Arg Arg Ser Ile Gly Ser Leu Ala Lys Pro Ala Thr Tyr
            485                 490                 495

Leu Thr Ala Leu Ser Gln Pro Lys Ile Tyr Arg Leu Asn Thr Trp Ile
            500                 505                 510

Ala Asp Ala Pro Ile Ala Leu Arg Gln Pro Asn Gly Gln Val Trp Ser
            515                 520                 525

Pro Gln Asn Asp
    530

(2) INFORMATION FOR SEQ ID NO:13:

(i) SEQUENCE CHARACTERISTICS:
        (A) LENGTH: 159 amino acids
        (B) TYPE: amino acid
        (C) STRANDEDNESS: single
        (D) TOPOLOGY: linear
```

(ii) MOLECULE TYPE: peptide (vi) ORIGINAL SOURCE:
            (A) ORGANISM: Escherichia coli (vii) IMMEDIATE SOURCE:
            (B) CLONE: pARC 0392

(xi) SEQUENCE DESCRIPTION: SEQ ID NO:13:

Gly Glu Gln Arg Leu Phe Val Pro Arg Ser Gly Phe Pro Asp Leu Leu
1               5                  10                  15

Val Asp Thr Leu Leu Ala Thr Glu Asp Arg His Phe Tyr Glu His Asp
                20                  25                  30

Gly Ile Ser Leu Tyr Ser Ile Gly Arg Ala Val Leu Ala Asn Leu Thr
            35                  40                  45

Ala Gly Arg Thr Val Gln Gly Ala Ser Thr Leu Thr Gln Gln Leu Val
        50                  55                  60

Lys Asn Leu Phe Leu Ser Ser Glu Arg Ser Tyr Trp Arg Lys Ala Asn
65                  70                  75                  80

Glu Ala Tyr Met Ala Leu Ile Met Asp Ala Arg Tyr Ser Lys Asp Arg
                85                  90                  95

Ile Leu Glu Leu Tyr Met Asn Glu Val Tyr Leu Gly Gln Ser Gly Asp
            100                 105                 110

Asn Glu Ile Arg Gly Phe Pro Leu Ala Ser Leu Tyr Tyr Phe Gly Arg
            115                 120                 125

Pro Val Glu Glu Leu Ser Leu Asp Gln Gln Ala Leu Leu Val Gly Met
        130                 135                 140

Val Lys Gly Ala Ser Ile Tyr Asn Pro Trp Arg Asn Pro Lys Leu
145                 150                 155

(2) INFORMATION FOR SEQ ID NO:14:

(i) SEQUENCE CHARACTERISTICS:
            (A) LENGTH: 28 bases
            (B) TYPE: nucleic acid
            (C) STRANDEDNESS: single
            (D) TOPOLOGY: linear (ii) MOLECULE TYPE: Other nucleic acid (synthethic DNA primer)

(xi) SEQUENCE DESCRIPTION: SEQ ID NO:14:

TCGACCATGG GCCTATACCG CTACATCG                                           28

(2) INFORMATION FOR SEQ ID NO:15:

(i) SEQUENCE CHARACTERISTICS:
            (A) LENGTH: 7 amino acids
            (B) TYPE: amino acids
            (C) STRANDEDNESS: single
            (D) TOPOLOGY: linear (ii) MOLECULE TYPE: peptide (xi) SEQUENCE DESCRIPTION: SEQ ID NO:15:

Met Gly Leu Tyr Arg Tyr Ile
                5

(2) INFORMATION FOR SEQ ID NO:16:

(i) SEQUENCE CHARACTERISTICS:
            (A) LENGTH: 30 bases
            (B) TYPE: nucleic acid
            (C) STRANDEDNESS: single
            (D) TOPOLOGY: linear (ii) MOLECULE TYPE: Other nucleic acid (synthethic DNA primer)

(xi) SEQUENCE DESCRIPTION: SEQ ID NO:16:

CGCGGATCCG AATCACAACA ATTCCTGTGC                                              30

(2) INFORMATION FOR SEQ ID NO:17:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:17:

GAAAAACCAT GGCCGGGAAT GACC                                                   24

(2) INFORMATION FOR SEQ ID NO:18:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:18:

AAGTCGCGAG CCGCGTTTGC CAC                                                    23

(2) INFORMATION FOR SEQ ID NO:19:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:19:

CGGATATCGA TCAAAAAATT CGTAGCCG                                               28

(2) INFORMATION FOR SEQ ID NO:20:

(i) SEQUENCE CHARACTERISTICS:
        (A) LENGTH: 31 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:20:

GCGGATCCTT AGTCGACGAC CACAATCGCA G                                           31

(2) INFORMATION FOR SEQ ID NO:21:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:21:

TACGTTACCA TGGCTCCTAG CCTATCC                                                27

(2) INFORMATION FOR SEQ ID NO:22:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:22:

GACAGGATCC TGAGAAGATG TCTTCTCA                      28

(2) INFORMATION FOR SEQ ID NO:23:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:23:

ACGCTGACGG CCGCTCTGGT GAAA                          24

(2) INFORMATION FOR SEQ ID NO:24:

(i) SEQUENCE CHARACTERISTICS:
        (A) LENGTH: 8 amino acids
        (B) TYPE: amino acids
        (C) STRANDEDNESS: single
        (D) TOPOLOGY: linear (ii) MOLECULE TYPE: peptide (xi) SEQUENCE DESCRIPTION: SEQ ID NO:24:

Thr Leu Thr Ala Ala Leu Val Lys
               5

(2) INFORMATION FOR SEQ ID NO:25:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:25:

ACGCTGACGC TATTGCTGGT GAAA                          24

(2) INFORMATION FOR SEQ ID NO:26:

(i) SEQUENCE CHARACTERISTICS:
        (A) LENGTH: 8 amino acids
        (B) TYPE: amino acids
        (C) STRANDEDNESS: single
        (D) TOPOLOGY: linear (ii) MOLECULE TYPE: peptide (xi) SEQUENCE DESCRIPTION: SEQ ID NO:26:

Thr Leu Thr Leu Leu Leu Val Lys
               5

(2) INFORMATION FOR SEQ ID NO:27:

(i) SEQUENCE CHARACTERISTICS:
    (A) LENGTH: 24 bases
    (B) TYPE: nucleic acid
    (C) STRANDEDNESS: single
    (D) TOPOLOGY: linear (ii) MOLECULE TYPE: Other nucleic acid (synthethic DNA primer)

(xi) SEQUENCE DESCRIPTION: SEQ ID NO:27:

CGCACGGTAC AGCTGGTGAA AAAC                                      24

(2) INFORMATION FOR SEQ ID NO:28:

(i) SEQUENCE CHARACTERISTICS:
        (A) LENGTH: 7 amino acids
        (B) TYPE: amino acids
        (C) STRANDEDNESS: single
        (D) TOPOLOGY: linear (ii) MOLECULE TYPE: peptide (xi) SEQUENCE DESCRIPTION: SEQ ID NO:28:

Arg Thr Val Gln Leu Val Lys
                5

(2) INFORMATION FOR SEQ ID NO:29:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:29:

GCGCGGACCA TGGTGAAGTT CGTAAAGTAT                                30

(2) INFORMATION FOR SEQ ID NO:30:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:30:

CAGTGCTGCA GTAATGGTAC TTGCCCCTTG                                30

(2) INFORMATION FOR SEQ ID NO:31:

(i) SEQUENCE CHARACTERISTICS:
        (A) LENGTH: 30 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:31:

ATTACTGCAG CACTGGCGAG AAACTTCTTC                                30

(2) INFORMATION FOR SEQ ID NO:32:

(i) SEQUENCE CHARACTERISTICS:
        (A) LENGTH: 30 bases
        (B) TYPE: nucleic acid

```
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:32:

TCGCGAGATA TCTGGCGGAT TGATCGACAC                                          30

(2) INFORMATION FOR SEQ ID NO:33:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:33:

GAAAAACCAT GGCCGGGAA TGACC                                                24

(2) INFORMATION FOR SEQ ID NO:34:

(i) SEQUENCE CHARACTERISTICS:
        (A) LENGTH: 27 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:34:

ATGGGATCCT TAATCATTCT GCGGTGA                                             27

(2) INFORMATION FOR SEQ ID NO:35:

(i) SEQUENCE CHARACTERISTICS:
        (A) LENGTH: 28 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:35:

CAATCCATGG GTGAGCAGCG TCTGTTTG                                            28

(2) INFORMATION FOR SEQ ID NO:36:

(i) SEQUENCE CHARACTERISTICS:
        (A) LENGTH: 25 bases
        (B) TYPE: nucleic acid
        (C) STRANDEDNESS: single
        (D) TOPOLOGY: linear (ii) MOLECULE TYPE: Other nucleic acid (synthethic DNA primer)

(xi) SEQUENCE DESCRIPTION: SEQ ID NO:36:

TCCAGAATTC CAGTTTTGGG TTACG                                               25

(2) INFORMATION FOR SEQ ID NO:37:

(i) SEQUENCE CHARACTERISTICS:
        (A) LENGTH: 34 bases
        (B) TYPE: nucleic acid
        (C) STRANDEDNESS: single
        (D) TOPOLOGY: linear (ii) MOLECULE TYPE: Other nucleic acid (synthethic DNA primer)
```

(xi) SEQUENCE DESCRIPTION: SEQ ID NO:37:

TCGAGGATCC CCATGGGCCT ATACCGCTAC ATCG                                34

(2) INFORMATION FOR SEQ ID NO:38:

(i) SEQUENCE CHARACTERISTICS:
            (A) LENGTH: 24 bases
            (B) TYPE: nucleic acid
            (C) STRANDEDNESS: single
            (D) TOPOLOGY: linear (ii) MOLECULE TYPE: Other nucleic acid (synthethic DNA primer)

(xi) SEQUENCE DESCRIPTION: SEQ ID NO:38:

GTTAGAATTC GAACAATTCC TGTG                                          24

(2) INFORMATION FOR SEQ ID NO:39:

(i) SEQUENCE CHARACTERISTICS:
            (A) LENGTH: 45 bases
            (B) TYPE: nucleic acid
            (C) STRANDEDNESS: single
            (D) TOPOLOGY: linear (ii) MOLECULE TYPE: Other nucleic acid (synthethic DNA primer)

(xi) SEQUENCE DESCRIPTION: SEQ ID NO:39:

AATTCGACGA CGACGACAAG CACCACCACC ACCACCACTG ATAAG                   45

(2) INFORMATION FOR SEQ ID NO:40:

(i) SEQUENCE CHARACTERISTICS:
            (A) LENGTH: 45 bases
            (B) TYPE: nucleic acid
            (C) STRANDEDNESS: single
            (D) TOPOLOGY: linear (ii) MOLECULE TYPE: Other nucleic acid (synthethic DNA primer)

(xi) SEQUENCE DESCRIPTION: SEQ ID NO:40:

GATCCTTATC AGTGGTGGTG GTGGTGGTGC TTGTCGTCGT CGTCG                   45

(2) INFORMATION FOR SEQ ID NO:41:

(i) SEQUENCE CHARACTERISTICS:
            (A) LENGTH: 5 amino acids
            (B) TYPE: amino acids
            (C) STRANDEDNESS: single
            (D) TOPOLOGY: linear (ii) MOLECULE TYPE: peptide (xi) SEQUENCE DESCRIPTION: SEQ ID NO:41:

Asp Asp Asp Asp Lys
                  5

(2) INFORMATION FOR SEQ ID NO:42:

(i) SEQUENCE CHARACTERISTICS:
            (A) LENGTH: 6 amino acids
            (B) TYPE: amino acids
            (C) STRANDEDNESS: single
            (D) TOPOLOGY: linear (ii) MOLECULE TYPE: peptide (xi) SEQUENCE DESCRIPTION: SEQ ID NO:42:

His His His His His His

We claim:

1. A polypeptide which is a water-soluble active derivative of a bacterial bifunctional penicillin binding protein, said penicillin binding protein being bound to the cell membrane when expressed in a bacterial cell and being capable of exhibiting both transglycosylase and transpeptidase activities and said polypeptide derivative thereof lacking a membrane anchoring sequence but retaining the capability to exhibit one or both of said enzymic activities, wherein the derivative comprises an amino acid sequence identical to SEQ ID NO: 2, 4, 6, 12 or 13 in the Sequence Listing.

2. An isolated and purified DNA molecule which has a nucleotide sequence coding for a polypeptide derivative according to claim 1.

3. A DNA molecule according to claim 2, which comprises a nucleotide sequence identical to SEQ ID NO: 1, 3 or 5 in the Sequence Listing.

4. A process for the production of a water soluble polypeptide derivative according to claim 1 which comprises culturing *Escherichia coli* cells harbouring an expression vector wherein a DNA coding sequence for said polypeptide derivative is under the control of an isopropyl thiogalactoside (IPTG)-inducible promoter, said culturing being carried out in the presence of a sub-optimal concentration of IPTG for induction of said promoter and at a temperature in the range of 20 to 24° C.

5. A polypeptide which is a transglycosylase deficient derivative of a bacterial bifunctional penicillin binding protein, said penicillin binding protein being bound to the cell membrane when expressed in a bacterial cell and being capable of exhibiting both transglycosylase and transpeptidase activities and said polypeptide derivative thereof lacking the capability to exhibit transglycosylase activity but retaining the capability to exhibit transpeptidase activity, wherein the derivative comprises an amino acid sequence identical to SEQ ID NO: 7, 8, 9 or 10 in the Sequence Listing.

6. A polypeptide derivative according to claim 5 which is lacking transglycosylase activity because of a mutation or deletion in the portion of the gene coding for the second conserved region of said polypeptide derivative.

7. An isolated and purified DNA molecule which comprises a nucleotide sequence coding for a polypeptide derivative according to claim 5.

8. A polypeptide derivative according to claim 1 or 5 wherein the bacterial cell is an *Escherichia coli* cell or a *Streptococcus pneumoniae* cell.

9. A method of identifying antibodies capable of binding a bacterial bifunctional penicillin binding protein, which comprises the steps of (a) contacting a polypeptide derivative according to claim 1 or 5 with antibodies to be investigated in an antibody binding assays; and (b) selecting antibodies that bind to the polypeptide derivative.

10. A method of assaying for compounds which bind to a penicillin binding protein, which comprises (a) contacting a polypeptide derivative according to claim 1 or 5 with a compound to be investigated; and (b) detecting whether said compound binds to the polypeptide derivative.

11. A method according to claim 10 wherein the compound to be investigated is a monoclonal antibody or a labelled antibiotic compound.

12. A method of assaying for compounds which bind to a penicillin binding protein, which comprises (a) exposing a polypeptide derivative according to claim 1 or 5, immobilised on a solid support, to a potential inhibitor of a penicillin binding protein; (b) exposing an agent, known to bind a penicillin binding protein, to the immobilised polypeptide derivative; (c) removing the unbound fraction of said agent; and (d) assaying for said agent bound to the immobilised polypeptide derivative, the deficiency of agent bound to the immobilised polypeptide derivative indicating the ability of the potential inhibitor to bind to the penicillin binding protein.

13. A method according to claim 12 wherein the agent known to bind a penicillin binding protein is a monoclonal antibody or a labelled antibiotic compound.

14. A method of assaying for compounds which bind to a penicillin binding protein, which comprises (a) exposing a polypeptide derivative according to claim 1 or 5 to a potential inhibitor of a penicillin binding protein; (b) exposing said polypeptide derivative to an agent, known to bind a penicillin binding protein, which agent is immobilised on a solid support; and (c) assaying for said polypeptide derivative bound to the immobilised agent, the deficiency of polypeptide derivative bound to the immobilised agent indicating the ability of the potential inhibitor to bind to the penicillin binding protein.

15. A method according to claim 14 wherein the agent known to bind a penicillin binding protein is a monoclonal antibody or a labelled antibiotic compound.

16. A fusion protein comprising (a) a first polypeptide according to claim 1 operably linked to (b) an additional polypeptide which allows binding to an affinity matrix, there being a cleavage site between said polypeptides.

17. An isolated and purified DNA molecule which comprises a nucleotide sequence coding for a fusion protein according to claim 16.

18. A fusion protein comprising (a) a first polypeptide according to claim 5 operably linked to (b) an additional polypeptide which allows binding to an affinity matrix, there being a cleavage site between said polypeptides.

19. An isolated and purified DNA molecule which comprises a nucleotide sequence coding for a fusion protein according to claim 18.

20. A fusion protein according to claim 16 or 18 wherein the additional polypeptide is gluthathione-S-transferase.

21. A fusion protein according to claim 16 or 18 wherein the additional polypeptide is a polypeptide rich in histidine residues such that it is capable of binding to an Ni affinity column.

22. A replicable expression vector which carries, and is capable of mediating the expression of, a DNA molecule according to any one of claims 2, 3, 7, 17, and 19.

23. An isolated cell harbouring a vector according to claim 22.

24. A process for production of a polypeptide which is a derivative of a penicillin binding protein, comprising growing a cell according to claim 23 in or on a culture medium for expression of the polypeptide and optionally recovering the polypeptide.

25. A method of assaying for compounds which bind to a penicillin binding protein, which comprises (a) culturing cells according to claim 23; (b) lysing said cells and isolating the crude cell extract; (c) exposing said cell extract to a potential inhibitor of a penicillin binding protein; (d) introducing an agent, known to bind a penicillin binding protein, to said cell extract; (e) removing the unbound fraction of said agent; and (f) assaying for said agent in the cell extract, the deficiency of said agent in the extract indicating the ability of the potential inhibitor to bind to the penicillin binding protein.

26. A method according to claim 25 wherein the agent known to bind a penicillin binding protein is a monoclonal antibody or a labelled antibiotic compound.

27. A method of assaying for compounds which bind to a penicillin binding protein, which comprises (a) contacting a fusion protein according to claim 16 or 18 with a compound to be investigated; and (b) detecting whether said compound binds to the fusion protein.

28. A method according to claim 27 wherein the compound to be investigated is a monoclonal antibody or a labelled antibiotic compound.

29. A method of assaying for compounds which bind to a penicillin binding protein, which comprises (a) exposing a fusion protein according to claim 16 or 18, immobilised on a solid support, to a potential inhibitor of a penicillin binding protein; (b) exposing an agent, known to bind a penicillin binding protein, to the immobilised fusion protein; (c) removing the unbound fraction of said agent; and (d) assaying for said agent bound to the immobilised fusion protein, the deficiency of agent bound to the immobilised fusion protein indicating the ability of the potential inhibitor to bind to the penicillin binding protein.

30. A method according to claim 29 wherein the agent known to bind a penicillin binding protein is a monoclonal antibody or a labelled antibiotic compound.

31. A method of assaying for compounds which bind to a penicillin binding protein, which comprises (a) exposing a fusion protein according to claim 16 or 18 to a potential inhibitor of a penicillin binding protein; (b) exposing said fusion protein to an agent, known to bind a penicillin binding protein, which agent is immobilised on a solid support; and (c) assaying for said fusion protein bound to the immobilised agent, the deficiency of fusion protein bound to the immobilised agent indicating the ability of the potential inhibitor to bind to the penicillin binding protein.

32. A method according to claim 31 wherein the agent known to bind a penicillin binding protein is a monoclonal antibody or a labelled antibiotic compound.

33. A replicable expression vector which is pARC0558 (NCIMB No. 40666), pARC0559 (NCIMB No. 40667), pARC0512 (NCIMB No. 40665), pARC0438 (NCIMB No. 40661), pARC0468 (NCIMB No. 40662), pARC0469 (NCIMB No. 40663), pARC0571 (NCIMB No. 40668), pARC0593 (NCIMB No. 40670), pARC0392 (NCIMB No. 40659), pARC0499 (NCIMB No. 40664), or pARC0400 (NCIMB No. 40660).

\* \* \* \* \*